United States Patent [19]
Naruo et al.

[11] Patent Number: 5,622,928
[45] Date of Patent: Apr. 22, 1997

[54] GLIA ACTIVATION FACTOR AND ITS PRODUCTION

[75] Inventors: Ken-ichi Naruo, Hyogo; Chisako Seko, Osaka; Tsutomu Kurokawa, Hyogo; Tatsuya Kondo, Tokyo, all of Japan

[73] Assignee: Takeda Chemical Industries, Ltd., Osaka, Japan

[21] Appl. No.: 593,535

[22] Filed: Jan. 24, 1996

Related U.S. Application Data

[62] Division of Ser. No. 340,820, Nov. 17, 1994, Pat. No. 5,512,460, which is a continuation of Ser. No. 835,713, Feb. 12, 1992, abandoned.

[30] Foreign Application Priority Data

Feb. 14, 1991 [JP] Japan .................................. 3-20860
Apr. 9, 1991 [JP] Japan ................................ 3-224454
Jan. 10, 1992 [JP] Japan ..................................... 4-3399

[51] Int. Cl.$^6$ .................................................. A61K 38/18
[52] U.S. Cl. ......................... 514/2; 424/185.1; 435/69.1; 435/71.1; 435/172.1; 435/252.3; 435/254.11; 530/350
[58] Field of Search ............................... 514/2; 424/185.1; 435/69.1, 71.1, 172.1, 240.1, 252.3, 254.11; 530/350

[56] References Cited

PUBLICATIONS

Kimura et al. letter "Structure, expression and function of a schwannoma–derived growth factor", *Nature*, vol. 348, pp. 257–260 (1990).

Guenther et al. article "A glia–derived neurite–promoting factor with protease inhibitory activity", *The EMBO Journal*. vol. 4, No. 8, pp. 1963–1966 (1985).

Giulian et al., article "Brain peptides and Glial Growth: II. Identification of Cells that Secrete Glial–Promoting Factors", *The Journal of Cell Biology*, vol. 102, pp. 812–829, March 1986.

Giulian et al., article "Brain peptides and Glial Growth: I. Glia–Promoting Factors as Regulators of Gligoeneis in Developing and Injured Nervous System", *The Journal of Cell Biology*, vol. 102, pp. 803–811, Mar. 1986.

Chemical Abstracts, vol. 98, No. 15, Apr. 11, 1983, Columbus, Ohio, US; Abstract No. 123664a, Nister M. et al: "A platelet–derived growth factor analog produced by a human clonal glioma cell line", p. 445; column L.

Chemical Abstracts, vol. 96, No. 1, Jan. 4, 1982, Columbus, Ohio, US; Abstract No. 4542H, Kato, Taiji et al: "Glial cell growth–promoting factor in astrocytoma C6 cell extracts", p. 421; column L.

Chemical Abstracts, vol. 110, No. 11, Mar. 13, 1989, Columbus, Ohio, US; Abstract No. 89388T, Guilan, Dana et al: "Secreted peptides as regulators of neuron–glia and glia interactions in the developing nervous system " p.162; column L.

The Journal of Neuroscience, vol. 4, No. 1, Jan. 1984, Washington, D.C.; USA pp. 75–83; Greg Erwin Lemke et al: "Identification and purification of glial growth factor.".

*Primary Examiner*—Christine M. Nucker
*Assistant Examiner*—Laurie Scheiner
*Attorney, Agent, or Firm*—David G. Conlin; George W. Neuner; Cara Z. Lowen

[57] ABSTRACT

Disclosed are (1) a novel glia activating factor which has glial cell growth promoting activity; (2) a glia activating factor containing a polypeptide; (3) a DNA coding for a glia activating factor; (4) a host transformed with a vector containing the DNA and (5) a method for producing the above glia activating factor which comprises cultivating the transformant described in a medium, accumulating the glia activating factor in a culture broth, and collecting the resulting glia activating factor.

12 Claims, 33 Drawing Sheets

1,6: Molecular weight 25,000 GAF
2,7: Molecular weight 29,000 GAF
3,8: Molecular weight 30,000 GAF
4,9: acidicFGF
5,10: basicFGF
1~5: Rabbit anti-acidic FGF polyclonal anti-serum
6~10: Rabbit anti-basic FGF polyclonal anti-serum
M: Colored standard protein 1. Colored standard protein (Amersham, England)

2. 25kDa GAF 3. 29kDa GAF 4. 30kDa GAF

1. Standard protein

2. N-glycanase alone 3. 30 kDa GAF 4. 30 kDA GAF + N-glycanase 5. 29 kDa GAF 6. 29 kDa GAF + N-glycanase 7. 25 kDa GAF 8. 25 kDa GAF + N-glycanase

```
        10          20          30          40          50          60
TGAAACAGCAGATTACTTTTATTTATGCATTTAATGGATTGAAGAAAAGAACCTTTTTT 70          80          90         100         110         120
TTCTCTCTCTCTCTGCAACTGCAGTAAGGGAGGGGAGTTGGATATACCTCGCCTAATATC 130         140         150         160         170         180
TCCTGGGTTGACACCATCATTATTGTTTATTCTTGTGCTCCAAAAGCCGAGTCCTCTGAT
                                                              Me
       190         200         210         220         230         240
GGCTCCCTTAGGTGAAGTTGGGAACTATTTCGGTGTGCAGGATGCGGTACCGTTTGGGAA
tAlaProLeuGlyGluValGlyAsnTyrPheGlyValGlnAspAlaValProPheGlyAs 250         260         270         280         290         300
TGTGCCCGTGTTGCCGGTGGACAGCCCGGTTTTGTTAAGTGACCACCTGGGTCAGTCCGA
nValProValLeuProValAspSerProValLeuLeuSerAspHisLeuGlyGlnSerGl 310         320         330         340         350         360
AGCAGGGGGGCTCCCCAGGGGACCCGCAGTCACGGACTTGGATCATTTAAAGGGGATTCT
uAlaGlyGlyLeuProArgGlyProAlaValThrAspLeuAspHisLeuLysGlyIleLe 370         380         390         400         410         420
CAGGCGGAGGCAGCTATACTGCAGGACTGGATTTCACTTAGAAATCTTCCCCAATGGTAC
uArgArgArgGlnLeuTyrCysArgThrGlyPheHisLeuGluIlePheProAsnGlyTh 430         440         450         460         470         480
TATCCAGGGAACCAGGAAAGACCACAGCCGATTTGGCATTCTGGAATTTATCAGTATAGC
rIleGlnGlyThrArgLysAspHisSerArgPheGlyIleLeuGluPheIleSerIleAl 490         500         510         520         530         540
AGTGGGCCTGGTCAGCATTCGAGGCGTGGACAGTGGACTCTACCTCGGGATGAATGAGAA
aValGlyLeuValSerIleArgGlyValAspSerGlyLeuTyrLeuGlyMetAsnGluLy 550         560         570         580         590         600
GGGGGAGCTGTATGGATCAGAAAAACTAACCCAAGAGTGTGTATTCAGAGAACAGTTCGA
sGlyGluLeuTyrGlySerGluLysLeuThrGlnGluCysValPheArgGluGlnPheGl 610         620         630         640         650         660
AGAAAACTGGTATAATACGTACTCGTCAAACCTATATAAGCACGTGGACACTGGAAGGCG
uGluAsnTrpTyrAsnThrTyrSerSerAsnLeuTyrLysHisValAspThrGlyArgAr 670         680         690         700         710         720
ATACTATGTTGCATTAAATAAAGATGGGACCCCGAGAGAAGGGACTAGGACTAAACGGCA
gTyrTyrValAlaLeuAsnLysAspGlyThrProArgGluGlyThrArgThrLysArgHi 730         740         750         760         770         780
CCAGAAATTCACACATTTTTTACCTAGACCAGTGGACCCCGACAAAGTACCTGAACTGTA
sGlnLysPheThrHisPheLeuProArgProValAspProAspLysValProGluLeuTy 790         800         810         820         830         840
TAAGGATATTCTAAGCCAAAGTTGACAAAGACAATTTCTTCACTTGAGCCCTTAAAAAAG
rLysAspIleLeuSerGlnSerEnd 850         860         870         880         890         900
TAACCACTATAAAGGTTTCACGCGGTGGGTTCTTATTGATTCGCTGTGTCATCACATCAG
```

FIG. 19A

```
          910       920       930       940       950       960
CTCCACTGTTGCCAAACTTTGTCGCATGCATAATGTATGATGGAGGCTTGGATGGGAATA 970       980       990      1000      1010      1020
TGCTGATTTTGTTCTGCACTTAAAGGCTTCTCCTCCTGGAGGGCTGCCTAGGGCCACTTG 1030      1040      1050      1060      1070      1080
CTTGATTTATCATGAGAGAAGAGGAGAGAGAGAGACTGAGCGCTAGGAGTGTGTGTAT 1090      1100      1110      1120      1130      1140
GTGTGTGTGTGTGTGTGTGTGTGTGTGTATGTGTGTAGCGGGAGATGTGGGCGGAGCG 1150      1160      1170      1180      1190      1200
AGAGCAAAAGGACTGCGGCCTGATGCATGCTGGAAAAAGACACGCTTTTCATTTCTGATC 1210      1220      1230      1240      1250      1260
AGTTGTACTTCATCCTATATCAGCACAGCTGCCATACTTCGACTTATCAGGATTCTGGCT 1270      1280      1290      1300      1310      1320
GGTGGCCTGCGCGAGGGTGCAGTCTTACTTAAAAGACTTTCAGTTAATTCTCACTGGTAT 1330      1340      1350      1360      1370      1380
CATCGCAGTGAACTTAAAGCAAAGACCTCTTAGTAAAAAATAAAAAAAAATAAAAAATAA 1390      1400      1410      1420      1430      1440
AAATAAAAAAAGTTAAATTTATTTATAGAAATTCCAAAAAAAAAAAAAAAAAAAAAAAA 1450      1460      1470      1480      1490
AAAAAAAAAAAAAAAAAAAAAAAAAAAAAAAAAAAAAAAAAAAAAAAAAAAAA
```

FIG. 19B

1. Colored standard protein (Amersham, England)

2. Extract of MM294(DE3)/pLys,pET3C

3. Extract of MM294(DE3)/pLys,pETGAF1

E1: 20 mM Tris-HCl BUFFER (pH 7.6) SUPPLEMENTED WITH
12.5% SATURATED AMMONIUM SULFATE AND 2mMa PMSF E2: 20 mM Tris-HCl BUFFER (pH 7.6) SUPLEMENTED WITH
15% GLYCERIN, 0.1% CHAPS AND 2 mMa PMSF 1. Colored standard protein (Amersham, England)
2. Purified rhGAF

GLIA ACTIVATION FACTOR AND ITS PRODUCTION

This is a divisional of application Ser. No. 08/340,820 filed on Nov. 17,1994 now U.S. Pat. No. 5,512,460, which is a FWC of Ser. No. 07/835,713 filed on Feb. 12, 1992 now abandoned.

BACKGROUND OF THE INVENTION

The present invention relates to a glia activating factor, a novel polypeptide, which is obtained from glioma cell culture solution and exhibits growth promoting activity against glial cells, fibroblasts and the like, a DNA coding for the glia activating factor, and a recombinant DNA for the preparation of the glia activating factor.

Various growth factors have been discovered, studied and utilized [*Cellular & Molecular Biology*, edited by The Japanese Tissue Culture Association, Asakura Shoten (1987)]. Such cell growth factors include epidermal growth factor (EGF), platelet-derived growth factor (PDGF), acidic fibroblast growth factor (aFGF) and basic fibroblast growth factor (bFGF). All of these factors have been isolated based upon growth promotion of fibroblast cells. However, these factors have also been found to display widely ranging activity and poor specificity. Accordingly, recent attempts have been made to search for growth factors specifically acting on functionally differentiated cells. As a result, growth factors such as keratinocyte growth factor (KGF) and hepatocyte growth factor (HGF) have been isolated, thus creating the possibility that these factors could be used to treat diseases vulnerable to their specific action spectra.

Encephalopathy of old age, particularly dementia, has been found to result from known disorders, such as injury-provoked cerebral nerve cell death, and from unknown disorders. Because cerebral nerve cells cease to proliferate immediately after birth and thereafter gradually decrease in number, there is no natural mechanism by which to repair damaged cerebral nerve cell or add new cerebral nerve cells at any significant rate. Thus, restoration of cerebral nerve cell activity requires artificial stimuli.

Glial cells, classified according to their form and function as either Type I or II astrocyte, or oligodendrocyte, surround and support the survival of cerebral nerve cells. The activation of these glial cells results in the activation and retention of the cerebral nerve cells. Such activation and retention is an important measure for improvement in an encephalopathologic condition. Despite extensive research into the identification of the neurotrophic factor released by glial cells, no decisive factor has been discovered as yet. Accordingly, research has focused upon the activation of the glial cells and the growth factors acting on those glial cells.

As described above, the identification and isolation of growth factors acting on the glial cells have been researched, in order to exploit their ability to activate cerebral nerve cells, and PDGF and FGF have been known to exhibit growth promoting activity also against the glial cells. However, the specificity of these factors is so poor that they exhibit strong strong growth promoting activity against other types of cells. Accordingly, they have not been able to be satisfactorily used as drugs. In sum, the prior art had not successfully identified a factor which strongly and specifically activated glial cells, and thus did not provide a drug capable of treating encephalopathy.

SUMMARY OF THE INVENTION

In the course of their research, the present inventors discovered a growth promoting factor which not only activates glial cells but is also produced by glial cells. However, large scale production of this factor has been hindered for two reasons. First, their inability to proliferate renders impossible the large scale collection of glial cells from humans. Second, there is no known technique by which a few glial cells can be retained and cultivated. Therefore, a substitute substrate for the glial cell was required.

Faced with these problems, the present inventors began work with glioma cells. Because glioma cell lines have the characteristics of normal glial cells, they were believed to be an adequate substitute substrate. Using the glioma cells, the present inventors were able to isolate and purify the above cited glial activating factor (hereinafter, "GAF").

Although use of glioma cells is suitable for the isolation and purification of GAF, their use for the large scale production of GAF is not. The present inventors found that the amount of GAF obtained from the human glioma cells is very slight. Therefore, prohibitive amounts of time and labor are required for cultivation of a large amount of glioma cells to obtain the GAF in amounts sufficient to use as a drug or a material for research. To increase production of GAF, the present inventors examined a method comprising cloning a polynucleotide coding for the GAF and applying the cloned polynucleotide to a recombinant DNA technique recently developed using the polynucleotide.

In furtherance of this proposed method, the amino acid sequence of the N-terminal side of GAF was analyzed, and oligonucleotide probes based on this sequence were synthesized. Screening was performed for cDNA libraries prepared from mRNA of human glioma cell NMC-G1 or of human foreskin-derived primary culture cells, using the above-mentioned probe, and human GAF CDNA was cloned. Finally, human GAF was produced by constructing an expression plasmid containing this cDNA and cultivating transformants transformed with this plasmid.

In accordance with the present invention, there are provided (1) a glia activating factor which is a protein obtained from a glioma cell culture solution and having glial cell growth promoting activity; (2) the above-mentioned glia activating factor in which the glioma cell is a human glioma cell; (3) a glia activating factor containing a polypeptide represented by the following amino acid sequence (SEQ ID NO:1):

|     |     |     |     |     | Leu | Asp | His | Leu | Lys | Gly | Ile | Leu | Arg | Arg | Arg |
| --- | --- | --- | --- | --- | --- | --- | --- | --- | --- | --- | --- | --- | --- | --- | --- |
| Gln | Leu | Tyr | Cys | Arg | Thr | Gly | Phe | His | Leu | Glu | Ile | Phe | Pro | Asn |
| Gly | Thr | Ile | Gln | Gly | Thr | Arg | Lys | Asp | His | Ser | Arg | Phe | Gly | Ile |
| Leu | Glu | Phe | Ile | Ser | Ile | Ala | Val | Gly | Leu | Val | Ser | Ile | Arg | Gly |
| Val | Asp | Ser | Gly | Leu | Tyr | Leu | Gly | Met | Asn | Glu | Lys | Gly | Glu | Leu |
| Tyr | Gly | Ser | Glu | Lys | Leu | Thr | Gln | Glu | Cys | Val | Phe | Arg | Glu | Gln |
| Phe | Glu | Glu | Asn | Trp | Tyr | Asn | Thr | Tyr | Ser | Ser | Asn | Leu | Tyr | Lys |
| His | Val | Asp | Thr | Gly | Arg | Arg | Tyr | Tyr | Val | Ala | Leu | Asn | Lys | Asp |
| Gly | Thr | Pro | Arg | Glu | Gly | Thr | Arg | Thr | Lys | Arg | His | Gln | Lys | Phe |
| Thr | His | Phe | Leu | Pro | Arg | Pro | Val | Asp | Pro | Asp |     |     |     |     | or a mutein thereof having activity of the factor;

(4) The glia activating factor according to the above (3) in which said polypeptide is represented by the following amino acid sequence (SEQ ID NO:2(n=0), SEQ ID NO:3(n=1)):

wherein $X_1'$ represents Met; or Met Ala Pro; and X represents Leu Gly Glu Val Gly Asn Tyr Phe Gly Val Gln Asp Ala Val Pro Phe Gly Ash Val Pro Val Leu Pro Val Asp Ser Pro Val Leu Leu or a fragment thereof,

| (Met)n—$X_1$—Leu Asp His Leu Lys Gly Ile Leu Arg Arg Arg Gln | | | | | | | | | | | | | | | |
|---|---|---|---|---|---|---|---|---|---|---|---|---|---|---|---|
| Leu | Tyr | Cys | Arg | Thr | Gly | Phe | His | Leu | Glu | Ile | Phe | Pro | Asn | Gly |
| Thr | Ile | Gln | Gly | Thr | Arg | Lys | Asp | His | Ser | Arg | Phe | Gly | Ile | Leu |
| Glu | Phe | Ile | Ser | Ile | Ala | Val | Gly | Leu | Val | Ser | Ile | Arg | Gly | Val |
| Asp | Ser | Gly | Leu | Tyr | Leu | Gly | Met | Asn | Glu | Lys | Gly | Glu | Leu | Tyr |
| Gly | Ser | Glu | Lys | Leu | Thr | Gln | Glu | Cys | Val | Phe | Arg | Glu | Gln | Phe |
| Glu | Glu | Asn | Trp | Tyr | Asn | Thr | Tyr | Ser | Ser | Asn | Leu | Tyr | Lys | His |
| Val | Asp | Thr | Gly | Arg | Arg | Tyr | Tyr | Val | Ala | Leu | Asn | Lys | Asp | Gly |
| Thr | Pro | Arg | Glu | Gly | Thr | Arg | Thr | Lys | Arg | His | Gln | Lys | Phe | Thr |
| His | Phe | Leu | Pro | Arg | Pro | Val | Asp | Pro | Asp—$X_2$ | | | | | | wherein n is 0 or 1; $X_1$ represents Ala Pro Leu Gly Glu Val Gly Asn Tyr Phe Gly Val Gln Asp Ala Val Pro Phe Gly Asn Val Pro Val Leu Pro Val Asp Ser Pro Val Leu Leu Ser Asp His Leu Gly Gln Ser Glu Ala Gly Gly Leu Pro Arg Gly Pro Ala Val Thr Asp or a fragment thereof; and $X_2$ represents Lys Val Pro Glu Leu Tyr Lys Asp Ile Leu Ser Gln Ser or a fragment thereof.

(5) The glia activating factor according to the above (3) in which said polypeptide is represented by the following amino acid sequence (SEQ ID NO:4(n=0, X3=Ala Pro); SEQ ID NO:5(n=0, X3=Leu Gly . . . Leu Leu); SEQ ID NO:6(n=1, $X_3$=Ala Pro); SEQ ID Pro); SEQ ID NO:7 (n=1, $X_3$=Leu Gly . . . Leu Leu):

(7) a DNA containing a polynucleotide coding for a glial activating factor;

(8) the DNA described in (7) in which the polynucleotide contains the following nucleotide sequence (SEQ ID NO:10):

| (Met)n $X_3$ Ser Asp His Leu Gly Gln Ser Glu Ala Gly Gly Leu | | | | | | | | | | | | | | | |
|---|---|---|---|---|---|---|---|---|---|---|---|---|---|---|---|
| Pro | Arg | Gly | Pro | Ala | Val | Thr | Asp | Leu | Asp | His | Leu | Lys | Gly | Ile |
| Leu | Arg | Arg | Arg | Gln | Leu | Tyr | Cys | Arg | Thr | Gly | Phe | His | Leu | Glu |
| Ile | Phe | Pro | Asn | Gly | Thr | Ile | Gln | Gly | Thr | Arg | Lys | Asp | His | Ser |
| Arg | Phe | Gly | Ile | Leu | Glu | Phe | Ile | Ser | Ile | Ala | Val | Gly | Leu | Val |
| Ser | Ile | Arg | Gly | Val | Asp | Ser | Gly | Leu | Tyr | Leu | Gly | Met | Asn | Glu |
| Lys | Gly | Glu | Leu | Tyr | Gly | Ser | Glu | Lys | Leu | Thr | Gln | Glu | Cys | Val |
| Phe | Arg | Glu | Gln | Phe | Glu | Glu | Asn | Trp | Tyr | Asn | Thr | Tyr | Ser | Ser |
| Asn | Leu | Tyr | Lys | His | Val | Asp | Thr | Gly | Arg | Arg | Tyr | Tyr | Val | Ala |
| Leu | Asn | Lys | Asp | Gly | Thr | Pro | Arg | Glu | Gly | Thr | Arg | Thr | Lys | Arg |
| His | Gln | Lys | Phe | Thr | His | Phe | Leu | Pro | Arg | Pro | Val | Asp | Pro | Asp |
| Lys | Val | Pro | Glu | Leu | Tyr | Lys | Asp | Ile | Leu | Ser | Gln | Ser | | | wherein n is 0 or 1; and $X_3$ represents Ala Pro; or Leu Gly Glu Val Gly Asn Tyr Phe Gly Val Gln Asp Ala Val Pro Phe Gly Asn Val Pro Val Leu Pro Val Asp Ser Pro Val Leu Leu or a fragment thereof.

(6) The glial activating factor according to the above (5) in which said polypeptide is represented by the following amino acid sequence (SEQ ID NO: 8($X_1'$=Met); SEQ ID NO: 9($X_1'$=Met Ala Pro)):

| $X_1'$ | $X_2'$ | Ser | Asp | His | Leu | Gly | Gln | Ser | Glu | Ala | Gly | Gly | Leu | Pro |
|---|---|---|---|---|---|---|---|---|---|---|---|---|---|---|
| Arg | Gly | Pro | Ala | Val | Thr | Asp | Leu | Asp | His | Leu | Lys | Gly | Ile | Leu |
| Arg | Arg | Arg | Gln | Leu | Tyr | Cys | Arg | Thr | Gly | Phe | His | Leu | Glu | Ile |
| Phe | Pro | Asn | Gly | Thr | Ile | Gln | Gly | Thr | Arg | Lys | Asp | His | Ser | Arg |
| Phe | Gly | Ile | Leu | Glu | Phe | Ile | Ser | Ile | Ala | Val | Gly | Leu | Val | Ser |
| Ile | Arg | Gly | Val | Asp | Ser | Gly | Leu | Tyr | Leu | Gly | Met | Asn | Glu | Lys |
| Gly | Glu | Leu | Tyr | Gly | Ser | Glu | Lys | Leu | Thr | Gln | Glu | Cys | Val | Phe |
| Arg | Glu | Gln | Phe | Glu | Glu | Asn | Trp | Tyr | Asn | Thr | Tyr | Ser | Ser | Asn |
| Leu | Tyr | Lys | His | Val | Asp | Thr | Gly | Arg | Arg | Tyr | Tyr | Val | Ala | Leu |
| Asn | Lys | Asp | Gly | Thr | Pro | Arg | Glu | Gly | Thr | Arg | Thr | Lys | Arg | His |
| Gln | Lys | Phe | Thr | His | Phe | Leu | Pro | Arg | Pro | Val | Asp | Pro | Asp | Lys |
| Val | Pro | Glu | Leu | Tyr | Lys | Asp | Ile | Leu | Ser | Gln | Ser | | | |

| | | TTG | GATCATTTAA | AGGGGATTCT |
|---|---|---|---|---|
| CAGGCGGAGG | CAGCTATACT | GCAGGACTGG | ATTTCACTTA | GAAATCTTCC |
| CCAATGGTAC | TATCCAGGGA | ACCAGGAAAG | ACCACAGCCG | ATTTGGCATT |
| CTGGAATTTA | TCAGTATAGC | AGTGGGCCTG | GTCAGCATTC | GAGGCGTGGA |
| CAGTGGACTC | TACCTCGGGA | TGAATGAGAA | GGGGGAGCTG | TATGGATCAG |
| AAAAACTAAC | CCAAGAGTGT | GTATTCAGAG | AACAGTTCGA | AGAAAACTGG |
| TATAATACGT | ACTCGTCAAA | CCTATATAAG | CACGTGGACA | CTGGAAGGCG |
| ATACTATGTT | GCATTAAATA | AAGATGGGAC | CCCGAGAGAA | GGGACTAGGA |
| CTAAACGGCA | CCAGAAATTC | ACACATTTTT | TACCTAGACC | AGTGGACCCC | GAC |

(9) The DNA described in (7) in which the polynucleotide is represented by the following nucleotide sequence (SEQ ID NO:11):

| | | $Y_1$—TTG | GATCATTTAA | AGGGGATTCT |
|---|---|---|---|---|
| CAGGCGGAGG | CAGCTATACT | GCAGGACTGG | ATTTCACTTA | GAAATCTTCC |
| CCAATGGTAC | TATCCAGGGA | ACCAGGAAAG | ACCACAGCCG | ATTTGGCATT |
| CTGGAATTTA | TCAGTATAGC | AGTGGGCCTG | GTCAGCATTC | GAGGCGTGGA |
| CAGTGGACTC | TACCTCGGGA | TGAATGAGAA | GGGGGAGCTG | TATGGATCAG |
| AAAAACTAAC | CCAAGAGTGT | GTATTCAGAG | AACAGTTCGA | AGAAAACTGG |
| TATAATACGT | ACTCGTCAAA | CCTATATAAG | CACGTGGACA · | CTGGAAGGCG |
| ATACTATGTT | GCATTAAATA | AAGATGGGAC | CCCGAGAGAA | GGGACTAGGA |
| CTAAACGGCA | CCAGAAATTC | ACACATTTTT | TACCTAGACC | AGTGGACCCC |
| GAC—$Y_2$ | | | | | wherein $Y_1$ represents GCTCCCTTA GGTGAAGTTG GGAACTATTT CGGTGTGCAG GATGCGGTAC CGTTTGGGAA TGTGCCCGTG TTGCCGGTGG ACAGCCCGGT TTTGTTAAGT GACCACCTGG GTCAGTCCGA AGCAGGGGGG CTCCCCAGGG GAC-CCGCAGT CACGGAC or a fragment thereof; and Y2 represents AAAGTAC CTGAACTGTA TAAGGATATT CTAAGCCAAA GT or a fragment thereof, or a nucleotide sequence (SEQ ID NO:12) having an initiation codon ATG at the 5'-terminus thereof;

(10) The DNA described in (7) in which the polynucleotide is represented by the following nucleotide sequence (SEQ ID NO: 13):

| | | $Y_3$—AGT | GACCACCTGG | GTCAGTCCGA |
|---|---|---|---|---|
| AGCAGGGGGG | CTCCCCAGGG | GACCCGCAGT | CACGGACTTG | GATCATTTAA |
| AGGGGATTCT | CAGGCGGAGG | CAGCTATACT | GCAGGACTGG | ATTTCACTTA |
| GAAATCTTCC | CCAATGGTAC | TATCCAGGGA | ACCAGGAAAG | ACCACAGCCG |
| ATTTGGCATT | CTGGAATTTA | TCAGTATAGC | AGTGGGCCTG | GTCAGCATTC |
| GAGGCGTGGA | CAGTGGACTC | TACCTCGGGA | TGAATGAGAA | GGGGGAGCTG |
| TATGGATCAG | AAAAACTAAC | CCAAGAGTGT | GTATTCAGAG | AACAGTTCGA |
| AGAAAACTGG | TATAATACGT | ACTCGTCAAA | CCTATATAAG | CACGTGGACA |
| CTGGAAGGCG | ATACTATGTT | GCATTAAATA | AAGATGGGAC | CCCGAGAGAA |
| GGGACTAGGA | CTAAACGGCA | CCAGAAATTC | ACACATTTTT | TACCTAGACC |
| AGTGGACCCC | GACAAAGTAC | CTGAACTGTA | TAAGGATATT | CTAAGCCAAA | GT |
| wherein $Y_3$ | represents | GCTCCCTTA | GGTGAAGTTG | GGAACTATTT |
| CGGTGTGCAG | GATGCGGTAC | CGTTTGGGAA | TGTGCCCGTG | TTGCCGGTGG |
| ACAGCCCGGT | TTTGTTA | | | | or a fragment thereof, or a nucleotide sequence (SEQ ID NO:14) having an initiation codon ATG at the 5'-terminus thereof;

| Y'-AGT GACCACCTGG | GTCAGTCCGA | AGCAGGGGGG | CTCCCCAGGG | |
|---|---|---|---|---|
| GACCCGCAGT | CACGGACTTG | GATCATTTAA | AGGGGATTCT | CAGGCGGAGG |
| CAGCTATACT | GCAGGACTGG | ATTTCACTTA | GAAATCTTCC | CCAATGGTAC |
| TATCCAGGGA | ACCAGGAAAG | ACCACAGCCG | ATTTGGCATT | CTGGAATTTA |

| | | | | |
|---|---|---|---|---|
| TCAGTATAGC | AGTGGGCCTG | GTCAGCATTC | GAGGCGTGGA | CAGTGGACTC |
| TACCTCGGGA | TGAATGAGAA | GGGGGAGCTG | TATGGATCAG | AAAAACTAAC |
| CCAAGAGTGT | GTATTCAGAG | AACAGTTCGA | AGAAAACTGG | TATAATACGT |
| ACTCGTCAAA | CCTATATAAG | CACGTGGACA | CTGGAAGGCG | ATACTATGTT |
| GCATTAAATA | AAGATGGGAC | CCCGAGAGAA | GGGACTAGGA | CTAAACGGCA |
| CCAGAAATTC | ACACATTTTT | TACCTAGACC | AGTGGACCCC | GACAAAGTAC |
| CTGAACTGTA | TAAGGATATT | CTAAGCCAAA | | | wherein Y' represents AT GGCTCCCTTA GGTGAAGTTG GGAACTATTT CGGTGTGCAG GATGCGGTAC CGTTTGGGAA TGTGCCCGTG TTGCCGGTGG ACAGCCCGGT TTTGTTA or a fragment thereof.

(12) a transformant transformed with a vector containing the DNA described in (7); and

(13) a method for preparing the above glia activating factor comprising cultivating the transformant described in (12) in a medium, accumulating the glia activating factor in a culture product to form an accumulated product, and collecting the resulting accumulated glia activating factor.

BRIEF DESCRIPTION OF THE DRAWINGS

FIG. 19 shows a nucleotide sequence of GAF cDNA and an amino acid sequence deduced therefrom;

DESCRIPTION OF THE PREFERRED EMBODIMENTS

Figure 1:
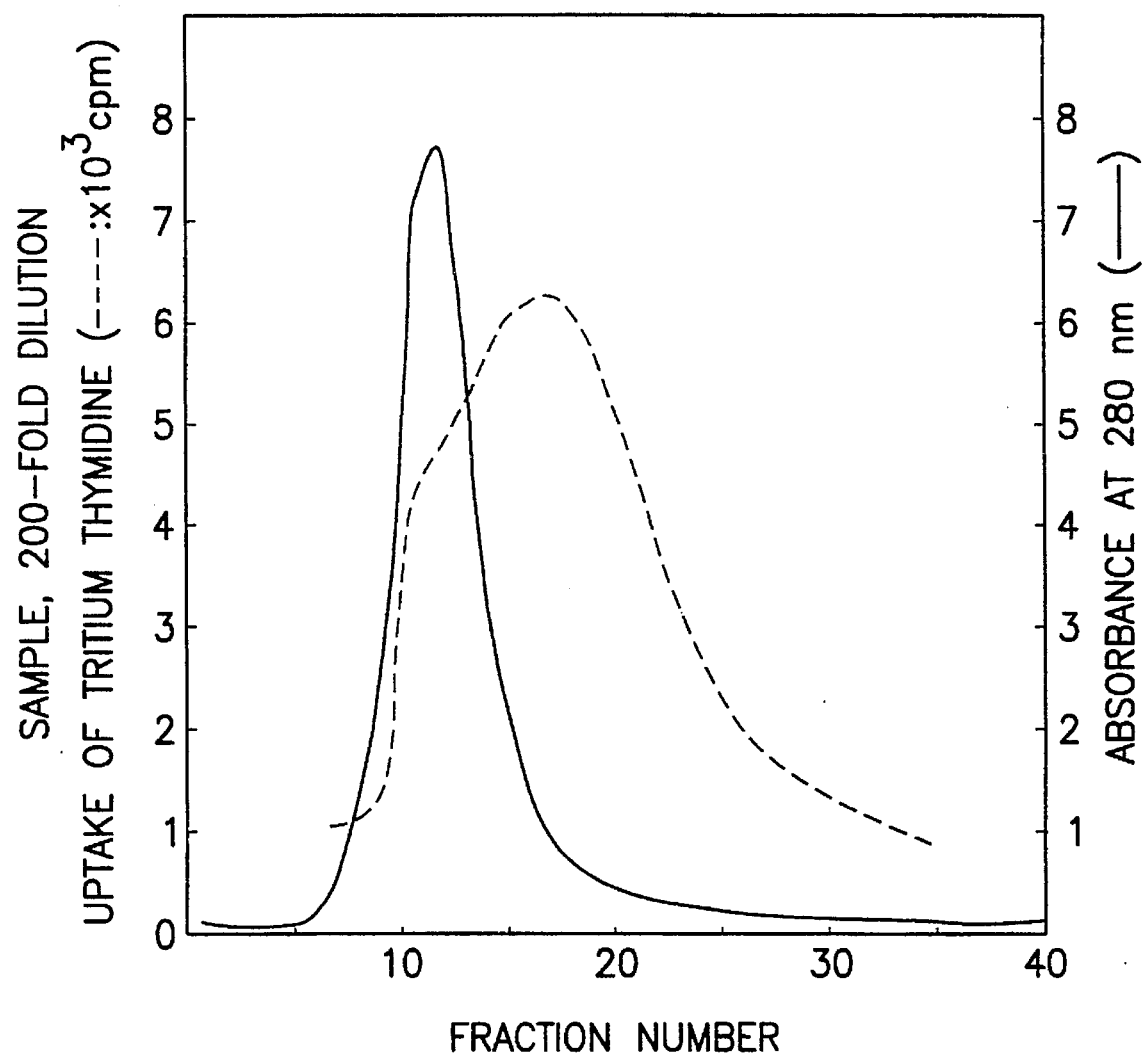
FIG. 1 shows elution patterns of protein and activity on heparin-Sepharose (registered trade mark) CL-6B column (Example 1-(2), step 1)

In accordance with the present invention, there is provided GAF, which is a protein isolated from a culture supernatant obtained by culturing the human-derived glioma cells or the transformant having GAF coding DNA and having the growth promoting activity to glial cells and fibroblasts.

GAF obtainable from glioma cells further has the following characteristics:

(a) Heparin affinity (it is eluted from a heparin-Sepharose column at a saline concentration of 0.4 to 0.9 M).

(b) Molecular weight: this factor includes three kinds of molecular species having molecular weights of about 25,000, about 29,000 and about 30,000, as measured by SDS polyacrylamide gel electrophoresis.

(c) Activity stability: the activity is lost by heat treatment at 100° C. for 5 minutes, and partially lost by treatment at pH 2 for 30 minutes.

(d) Antigenicity: this factor does not exhibit the any immunological cross reaction with platelet-derived growth factor (PDGF), acidic fibroblast growth factor (aFGF) and basic fibroblast growth factor (bFGF).

(e) Biological activity: This factor displays growth promoting activity upon glial cells, fibroblasts and rat phenochromocytoma PC-12 cells.

GAF obtained from glioma cell includes three kinds of molecular species having molecular weights of about 25,000, about 29,000 and about 30,000, repectively with each species being derived from the same gene. It is found that each has equivalent biological activity.

According to the present invention, there is further provided a method for preparing the GAF comprising culturing the human-derived glioma cells or the transformant described above, collecting the GAF from a culture supernatant thereof, and purifying the collected GAF.

The cell culture supernatant for obtaining GAF can be prepared by culture of glioma cells, for example, human glioma cell NMC-G1. Any method of culture such as stationary culture, roller bottle culture, cell factory or suspension culture may be used for culture of glioma cells. In preferred embodiments of the present invention, roller bottle culture is the preferred method. In this manner, media for culture of animal cells such as MEM medium [*Science*, 122, 501 (1952)], DMEM medium [*Virology*, 8, 396 (1959)], RPMI1640 medium [*Journal of the American Medical Association*, 199, 519 (1967)] and 199 medium [*Proceeding of the Society for the Biological Medicine*, 73, 1 (1950)] is used for cultivation. Preferably, DMEM medium is used. These media may be supplemented with up to about 20%, preferably about 5 to 20%, fetal calf serum. The pH is preferably about 6 to 8. The culture is carried out at 30° to 40° C., preferably at 37° C., for about 24 to 100 hours, with medium exchange if necessary.

The separation and purification of GAF protein from the above-mentioned culture supernatant can be carried out by appropriate combinations of well-known separating and purifying methods. These known separating and purifying methods include methods utilizing a difference in solubility such as salting-out and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography and isoelectro-focussing electrophoresis, methods utilizing a difference in specific affinity such as affinity chromatography, and methods utilizing a difference in hydrophobicity such as reverse phase high performance liquid chromatography.

Preferred methods of separation of GAF protein utilize chromatographic techaniques whereby after removal of precipitated impurities by centrifugation, the above-mentioned culture solution is subjected to heparin-Sepharose chromatography to adsorb and elute GAF protein so that the protein can be efficiently concentrated and purified.

Gel filtration using Sephacryl S-200 or the like is also effective for purification of GAF protein. In preferred embodiments, an eluate containing GAF protein concentrated by a heparin-Sepharose column is further concentrated by use of ultrafiltration or the like, and subjected to chromatography using a Sephacryl S-200 column to elute GAF protein with a buffer solution.

Column chromatography with an acidic resin such as CM cellulose is also effective seperation and purification technique. In preferred ambodiments, a sample dialyzed against a weak acidic buffer is loaded onto a column chromatography equilibrated with the same buffer, and linear gradient elution can be accomplished by use of a salt such as NaCl.

Affinity chromatography via heparin-Sepharose is very effective. For example, a GAF protein-containing solution is loaded onto a heparin-Sepharose column equilibrated with a nearly neutral buffer such as Tris hydrochloric acid or Tris phosphoric acid, and the column is thoroughly washed. Then, linear gradient elution is accomplished by use of a salt such as NaCl, whereby GAF protein can be eluted.

In particular, heparin columns for high performance liquid chromatography (for example, Shodex AF pak HR-894, Showa Denko K. K., Japan) are effective, and can be utilized in a manner similar to the above-mentioned heparin-Sepharose column.

GAF protein can also be purified by the reverse phase high performance liquid chromatography which gives excellent results on purification of many proteins. For example, a sample solution containing 0.1% trifluoroacetic acid is loaded onto the column, and elution can be made by a gradient of acetonitrile added to 0.1% trifluoroacetic acid.

GAF protein can be obtained as a homogeneous sample by appropriate combinations of the procedures described above.

The use of a trace amount of detergent in the purification process or the storage process is suitable for preventing a sample from being adsorbed to a chromatography resin or a vessel. Preferred detergents include 3-[(3-chloramidopropyl)dimethylammonio]-1-propanesulfonate (CHAPS), NP-40 and Triton X100. In certain embodiments of the present invention, CHAPS is preferred.

GAF protein in the culture supernatant and in the solutions of the purification process can be assayed for growth promoting activity based upon the uptake of $^3$H-thymidine by primary culture glial cells isolated from the brain of a rat fetus (19 days after fertilization) or by BALB/c3T3 cells.

The resulting purified sample may also be dialyzed and lyophilized to form a dried powder. Further, serum albumin is also suitably added thereto to assist in the sample's storage.

Using the purified sample, the sugar chain structure of GAF protein can be examined. For this purpose, blotting experiments using lectin as a probe or digestion experiments with sugar chain degrading enzymes can be utilized.

Upon obtaining a purified sample, the N-terminal side amino acid sequence can be examined directly with an amino acid sequencer. Furthermore, after degradation of the purified sample with proteinases such as trypsin, lysyl-end peptidase and V8 protease, the resulting peptide fragments are separated using reverse phase high performance liquid chromatography, and the amino acid sequence for each sequence can be examined to get information of the amino acid sequences in the inner part of the protein.

The use of an automatic amino acid sequencer (for example, Model 470A, Applied Biosystems, U.S.A.) is particularly effective for determination of the amino acid sequence.

The nucleotide sequence is deduced based on the resulting amino acid sequence, and the oligonucleotide which can be used for cloning of cDNA coding for GAF protein, is synthesized.

The cDNA thus obtained is expressed in organisms such as *Escherichia coli, Bacillus subtilis* and yeast, wherein the GAF protein can be obtained more easily. Animal culture cells are also used as expression hosts and are very suitable hosts when activity or stability requirements dictate that a sugar moiety of the GAF protein be used.

Use of the above described genetic engineering techniques provides for the easy mass production of GAF proteins.

When GAF is obtained by such genetic engineering techniques, amino acid sequences thereof sometimes differ from each other, such as a lack or substitution of amino acid(s), due to a difference in hosts or due to a mutation. Such proteins which have different amino acid sequences are contemplated as being within the scope of the present invention as long as they have GAF-activity.

Furthermore, because molecular species having slightly different N-terminal amino acid sequences as nonetheless found to coexist in GAF preparation purified from a culture supernatant of glioma cells and their specific activities are nearly the same, it is possible to delete part of the amino acid sequence of GAF, add another sequence thereto, or substitute within the sequence without the loss of biological activity. Thus, the present invention also provids mutant proteins which are more stable to heat or acid and can be easily prepared by these genetic engineering techniques.

In accordance with the present invention, an expression vector containing the DNA having the nucleotide sequence coding for GAF polypeptide can be prepared, for example, by the following process:

(a) GAF is isolated and purified from a culture supernatant, and the amino acid sequence on the N-terminal side is analyzed, (b) Based on the resulting amino acid sequence, an oligonucleotide probe coding for it is synthesized, (c) RNA coding for the GAF is extracted from the cells, (d) Single stranded complementary DNA (cDNA) is synthesized from the mRNA, followed by synthesis of double stranded complementary DNA, (e) The complementary DNA is introduced into a phage vector or a plasmid, (f) The recombinant phage or plasmid thus obtained is introduced into an appropriate host cell to produce a transformant, (g) After cultivation of the transformant thus obtained, the plasmid or the phage containing the desired DNA is isolated from the transformant by an appropriate method such as hybridization using the DNA probe, (h) The desired cloned DNA is cut out from the recombinant DNA, and (i) The cloned DNA or a portion thereof is ligated downstream from a promoter in a vector suitable for expression.

The mRNA coding for the human GAF can be obtained from various GAF-producing cells such as human glioma cells and human fibroblasts. The human glioma cells include NMC-G1, and the human fibroblasts include WI-38 (ATCC No.: CCL-75).

The above-mentioned cell NMC-G1 was deposited with the Institute for Fermentation, Osaka, Japan (IFO) under the accession number IFO 50281 on Oct. 31, 1990, and with the Fermentation Research Institute (FRI), Agency of Industrial Science and Technology, the Ministry of International Trade and Industry, 1–3, Higashi 1-chome, Tsukuba-shi Ibaraki-Ken Japan under the accession number FERM BP-3294 on Feb. 21, 1991. WI-38 is cited in *Catalogue of Cell Lines & Hybridomas,* 5th edition, published by the American Type Culture Collection (1985).

Methods for preparing the RNA from the GAF-producing cells include the guanidine thiocyanate method [J. M. Chirgwin et al., *Biochemistry,* 18, 5294 (1979)] and the like.

Using the mRNA thus obtained as a template, cDNA is synthesized and then introduced into the plasmid or the phage by use of reverse transcriptase, for example, in accordance with the method of H. Okayama et al. [*Molecular and Cellular Biology,* 2, 161 (1982) and ibid. 3, 280 (1983)].

The plasmids into which the cDNA is introduced include, for example, pBR322 [Gene, 2, 95 (1977)], pBR325 [*Gene* 4, 121 (1978)], pUC12 [*Gene,* 19, 259 (1982)], pUC13 [*Gene,* 19, 259 (1982)], pUC118 and pUC119, each derived from *E. coli,* and pUB110 derived from *Bacillus subtilis* [*Biochemical and Biophysical Research Communication,* 112, 678 (1983)]. However, any other plasmid can be used as long as it is replicable and viable in the host.

Methods for introducing the cDNA into the plasmid include, for example, the method described in T. Maniatis et al., *Molecular Cloning,* p.239, Cold Spring Laboratory, (1982). Methods for introducing the cDNA into the phage vector include, for example, the method of T. V. Hyunh et al. [*DNA Cloning, A Practical Approach,* 1, 49 (1985)].

The plasmids into which the above-mentioned cDNA is introduced may be obtained by introducing the cDNA prepared from human normal diploid cell mRNA into a vector such as pCD vector [see Okayama et al., *Molecular Cell Biology,* 3, 280 (1983)].

The plasmid into which cDNA has been introduced is introduced into appropriate host cells such as cells belong to Escherichia and Bacillus.

Examples of the cells belong to Escherichia described above include *E. coli* K12DH1 [*Proc. Natl. Acad. Sci. U.S.A.,* 60, 160 (1968)], M103 [*Nucleic Acids Research,* 9, 309 (1981)], JA221 [*Journal of Molecular Biology,* 120, 517, (1978)], HB101 [*Journal of Molecular Biology,* 41, 459 (1969)] and C600 [*Genetics,* 39, 440 (1954)].

Examples of the cells belong to Bacillus described above include *Bacillus subtilis* MI114 [*Gene,* 24, 255 (1983)] and 207–21 [*Journal of Biochemistry,* 95, 87 (1984)].

Methods for transforming the host with the plasmid include, for example, the calcium chloride method and the calcium chloride/rubidium chloride method described in T. Maniatis et al., *Molecular Cloning,* p.249, Cold Spring Harbor Laboratory, (1982).

Desired clones are selected from the transformants thus obtained by using methods known per se in the art such as the colony hybridization method [*Gene,* 10, 63 (1980)], and the DNA nucleotide sequence determination methods [*Proc. Natl. Acad. Sci. U.S.A.,* 74, 560 (1977); *Nucleic Acids Research,* 9, 309 (1981)].

Thus, a cloned microorganism is obtained which contains the vector having the DNA containing the nucleotide sequence coding for GAF.

The plasmid having the cDNA coding for the above-mentioned GAF can be used as is or after digestion with a restriction enzyme if desired, depending on the intended purpose.

The region intended to be expressed is cut out from the cloned cDNA and ligated downstream from a promoter in a vehicle (vector) suitable for expression, whereby the expression vector can be obtained.

The vectors include the above plasmids derived from *E. coli* such as pBR322, pBR325, pUC12 and pUC13, plasmids derived from *Bacillus subtilis* such as pUB110, pTP5 and pC194, plasmids derived from yeast such as pSH19 and pSH15, bacteriophages such as λ phage, and animal viruses such as retroviruses and vaccinia viruses.

The cDNA may have ATG as a translation initiating codon at the 5'-terminus thereof, and TAA, TGA or TAG as a translation terminating codon at the 3'-terminus thereof. These codons may be added by use of an appropriate synthetic DNA adaptor. A promoter is further ligated upstream therefrom to express the DNA.

In accordance with the present invention, any promoter may be used as long as it is suitable for expression in the host cell selected for the gene expression.

When the host cell used for transformation is Escherichia, it is preferable that a T7 promoter, a trp promoter, a lac promoter, a recA promoter, a λPL promoter, or an lpp promoter is used. When the host cell is Bacillus, it is preferable that an SPO1 promoter, an SPO2 promoter, or a penP promoter is used. When the host cell is yeast, it is preferable that a PHO5 promoter, a PGK promoter, a GAP promoter or an ADH promoter is used. In preferred embodiments of the present invention, the host cell is Escherichia and the promoter is the T7 promoter or the trp promoter.

When the host cell is an animal cell, a SV40-derived promoter, a retrovirus promoter or the like can be used. The SV40-derived promoter is preferred.

By using a vector containing the DNA coding for GAF thus constructed, the transformant is prepared.

Examples of the host cells include Escherichia, Bacillus, yeast and animal cells.

Examples of the above-mentioned Escherichia and Bacillus include strains similar to those described above.

Examples of the above-mentioned yeast include *Saccharomyces cerevisiae* AH22R⁻, NA87-11A and DKD-5D.

Specific examples of the above-mentioned animal cells include monkey cell COS-7, Vero, Chinese hamster cell (CHO), mouse L cell and human FL cell.

The transformation of Escherichia described above is conducted, for example, according to the method described in *Proc. Natl. Acad. Sci. U.S.A.*, 69, 2110 (1972), *Gene*, 17, 107 (1982) or the like.

The transformation of Bacillus is carried out, for example, according to the method described in *Molecular & General Genetics*, 168, 111 (1979) or the like.

The transformation of yeast is performed, for example, according to the method described in *Proc. Natl, Acad. Sci. U.S.A.*, 75, 1929 (1978).

The transformation of animal cells is carried out, for example, according to the method described in *Virology*, 52, 456 (1973).

Thus, the transformant transformed with the expression vector containing the cDNA coding for GAF is obtained.

Examples thereof include *E. coli* K12 DH1/pGAF1 obtained in Example 5 described below. This organism was deposited with the IFO under the accession number IFO 15217 on Aug. 28, 1991, and with the FRI under the accession number FERM BP-3547 on Sep. 2, 1991.

Further, *E. coli* MM294(DE3)/pLysS,pETGAF1 obtained in Example 8 was deposited with the IFO under the accession number IFO 15248 on Dec. 3, 1991, and with the FRI under the accession number FERM BP-3689 on Dec. 24, 1991. When bacterial transformants are cultivated, a liquid medium is typically used for cultivation. Carbon sources, nitrogen sources, inorganic compounds and other nutrients necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins and growth promoting factors may be further added.

The pH of the medium is preferably about 5 to about 8.

When the Escherichia transformants are cultivated, M9 medium containing glucose and Casamino Acids [Miller, *Journal of Experiments in Molecular Genetics*, 431–433, Cold Spring Harbor Laboratory, New York (1972)] is preferably used to cultivate the transformants. In order to allow the promoters to act more efficiently, for example, drugs such as 3β-indolyl acrylic acid may be added thereto if necessary.

The Escherichia transformants are usually cultivated at about 15° to 43° C. for about 3 to 24 hours with aeration or agitation if necessary.

The Bacillus transformants are usually cultivated at about 30° to 40° C. for about 6 to 24 hours with aeration or agitation if necessary.

When the yeast transformants are cultivated, the preferred media is Burkholder minimum medium [K. L. Bostian, *Proc. Natl. Acad. Sci. U.S.A.*, 77, 4505 (1980)]. The pH of the medium is preferably adjusted to about 5 to 8. The cultivation is usually carried out at about 20° to 35° C. for about 24 to 72 hours with aeration or agitation if necessary.

When the animal cell transformants are cultured, examples of media which can be used include MEM medium containing about 0 to 20% fetal calf serum [*Science*, 122, 501 (1952)], DMEM medium [*Virology*, 8, 396 (1959)], RPMI1640 medium [*Journal of the American Medical Association*, 199, 519 (1967)] and 199 medium [*Proceeding of the Society for the Biological Medicine*, 73, 1 (1950)]. The pH is preferably about 6 to 8. The cell culture is usually carried out at about 30° to 40° C. for about 15 to 60 hours, with aeration or agitation if necessary.

The isolation and purification of GAF from the above-mentioned culture products are carried out according to the following method.

First, the cells are collected by methods known in the art after cultivation. Then, the collected cells are suspended in a buffer solution or a solution containing a protein denaturant such as guanidine hydrochloride, and disrupted by ultrasonic treatment, lysozyme treatment and/or freeze-thawing thereby releasing GAF, followed by centrifugation to obtain GAF.

GAF can be purified from the extracts by methods known in the art. For example, methods such as fractionation using ammonium sulfate, ion-exchange chromatography, hydrophobic chromatography, affinity chromatography and gel filtration may be used. The column used for purification of naturally occurring GAF has been found to purify the GAF of the present invention very effectively. The homogeneous GAF protein can be obtained by combinations thereof. Further, a protease inhibitor may be added to the purification process when the protein must be obtained without degradation. Additionally, a mild detergent may be added to the purification process to increase the protein yield. In preferred embodiments of the present invention, CHAPS is preferred.

As explained above, GAF produced in accordance with the present invention has cell growth promoting activity to glial cells, so that it can be used as a therapeutic accelerant for cerebral lesion. GAF can also be used in therapy for diseases due to cerebral nerve cell lesion, cerebral edema, Alzheimer's disease, senile dementia and further diabetic neuropathies. Since GAF displays a stronger activity to glial cells than to other cells, it is expected to activate glial cells specifically. Moreover, because of growth promoting activity upon the fibroblasts, the GAF can be used as therapeutic accelerants for burns, wounds, postoperative tissue ulcers and gastrointestinal ulcers.

Also, it has been found that GAF acts on megakaryocytes to proliferate and differentiate these cells and to promote an increase in the number of platelets. GAF is also believed to promote the proliferation of other hematopoietic or immunocompetent cells. In particular, GAF is believed to take part in the activation of microglial cells which exist in the brain as immunocompetent cells. From this point, GAF will be able to be used for the treatment and improvement of cerebral lesion.

GAF scarcely acts on human umbilical vascular endothelial cells, but exhibits growth promoting activity to vascular smooth muscle cells. Accordingly, GAF will be useful in the treatment of damaged vascular smooth muscle.

As with other growth promoting factors such as aFGF, bFGF and IGF, GAF is also expected to have osteogenesis promoting activity, and application of GAF to fracture and osteoporosis is also expected.

As with the cDNA of bFGF, TGF-α, and PDGF, the cDNA of GAF can transform fibroblasts. Because of this transforming ability, an increase in the GAF expression is considered to be one of causes of malignancy in glioma cells. It is therefore conceivable that the production of GAF is heightened in cases displaying cerebral tumor. Therefore, tracking the level of GAF, using antibodies thereof and GAF cDNA will be a useful method for diagnosis of cerebral tumor. Moreover, antibodies to GAF can be used for anti brain tumor agent. Further, GAF can be utilized for the studies of culture of glial cells as an effective growth factor.

When GAF of the present invention is used as a drug, it can be safely given parenterally or orally to mammals (such as humans, mice, rats, hamsters, rabbits, dogs and cats), in a powder form as is or in a pharmaceutical composition (such as injections, tablets, capsules, solutions and ointments) with pharmaceutically acceptable carriers, excipients and diluents.

The injections of the GAF of the present invention is prepared by conventional methods using, for example, physiological saline or aqueous solutions containing glucose or other auxiliary agents. The pharmaceutical compositions such as tablets and capsules can also be prepared in accordance with conventional methods. The injections, solutions, tablets and capsules as the pharmaceutical compositions are prepared under aseptic conditions.

When the GAF of the present invention is used as a drug as described above, it is given, for example, to the above-mentioned animals in appropriate doses of about 0.5 ng to about 50 μg/kg once and about 1 ng to about 100 μg/kg daily, taking into account the routes of administration, symptoms, etc.

Further, when the GAF of the present invention is used as a reagent for promoting cell culture, it is added to a medium preferably in an amount of about 0.01 to about 10 μg per liter of medium, and more preferably in an amount of about 0.1 to about 10 μg per liter of medium.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine
Gln or Q: Glutamine

EXAMPLES

The present invention will be described in more detail through following Examples. It is understood of course that these Examples are not intended to limit the scope of the invention.

Reference Example 1

Assay of Growth Promoting Activity to Glial Cells

Primary culture glial cells prepared from the fetal rat brain were suspended in DMEM medium supplemented with 10% inactivated fetal calf serum at $3 \times 10^4$ cells/ml. 100 μl of the resulting cell suspension was poured into each well of a 96-well flat-bottomed microtiter plate (A/N Nunc, Roskilde, Denmark), and cultured for 2 to 3 days. Then, 75 µl of the medium was discarded from each well, and 175 µl of serum-free DMEM medium was added to each well. After additional culturing for 2 to 3 days, 20 µl of the medium was discarded from each well. Then, 20 µl of a test sample appropriately diluted with DMEM medium supplemented with 1.25% inactivated fetal calf serum was added to each well, followed by culturing overnight. The next morning, 1 µCi tritium thymidine (5 Ci/mmol, 1 mCi/ml, RCC Amersham) was added to each well, and culturing was further conducted for 5 to 7 hours. After culturing, the medium was discarded from each well, and 100 µl of PBS containing 0.5% trypsin and 0.01% EDTA was added to each well, followed by standing at room temperature for several minutes. After detachment of the glial cells was confirmed under a microscope, the detached cells were collected on a glass fiber filter (Dainippon Pharmaceutical Co., Ltd., Japan) using a Titertek Cell Harvester-(Flow Laboratories, Virginia, U.S.A.), and washed with water. Then, the amount of tritium thymidine taken into the cells was measured by a liquid scintillation counter.

Example 1

(1) Collection of Culture Supernatant of Glioma Cell NMC-G1

Human glioma NMC-G1 cells were cultured in DMEM medium supplemented with 10% fetal calf serum at 37° C. using a plastic roller bottle (Corning Iwaki Glass, Japan) with rotation (0.2 rpm). After the NMC-G1 cells became confluent on the surface of the roller bottle, the medium was changed to DMEM medium supplemented with 0.5% fetal calf serum. The cell culture supernatant was collected every 3 to 4 days, and the medium was changed with fresh DMEM medium supplemented with 0.5% fetal calf serum. The collected cell culture supernatant was then subjected to centrifugation (Model J-6B, Beckman, 4,000 rpm, 15 minutes) to obtain a centrifuged supernatant, which was used as a starting material.

(2) Purification of GAF

Step 1: Heparin affinity column chromatography

1/50 volume (360 ml) of a 5M NaCl solution and 1/1000 volume (18 ml) of 10% NaN$_3$ were added to an 18 liter volume of the NMC-G1 cell culture supernatant obtained by the method described in (1). The NMC-G1 cell culture supernatant thus prepared was passed through a heparin-Sepharose (registered trade mark) CL-6B column (bed volume: 80 ml, Pharmacia LKB Biotechnology, Uppsala, Sweden) pre-equilibrated with 20 mM Tris-HCl buffer (pH 7.6) containing 0.2 M NaCl, at a flow rate of 150 ml/hour at 4° C. by using a peristaltic pump. The resin was washed with 450 ml of 20 mM Tris-HCl buffer (pH 7.6) containing 0.2M NaCl, at a flow rate of 150 ml/hour at 4° C., and then, the adsorbed protein was eluted with 400 ml of 20 mM Tris-HCl buffer (pH 7.6) containing 2M NaCl (60 ml/hour, 8 ml/fraction, 4° C.) (FIG. 1). The growth promoting activity of each eluted GAF fraction upon glial cells was assayed by the method described in Reference Example 1, and fractions having the activity (fractions 11 to 23) were collected for future use.

Step 2: Concentration

In all, 32 liters of the culture supernatant was subjected to the heparin affinity chromatography of step 1, and active fractions were pooled (192 ml). This solution was concentrated to about 35 ml by use of a Diaflow YM-10 membrane (fractional molecular weight: 10,000, Amicon Corp., Massachusetts, U.S.A.) in an atmosphere of a nitrogen gas under pressure.

Step 3: Gel filtration chromatography

Figure 2:
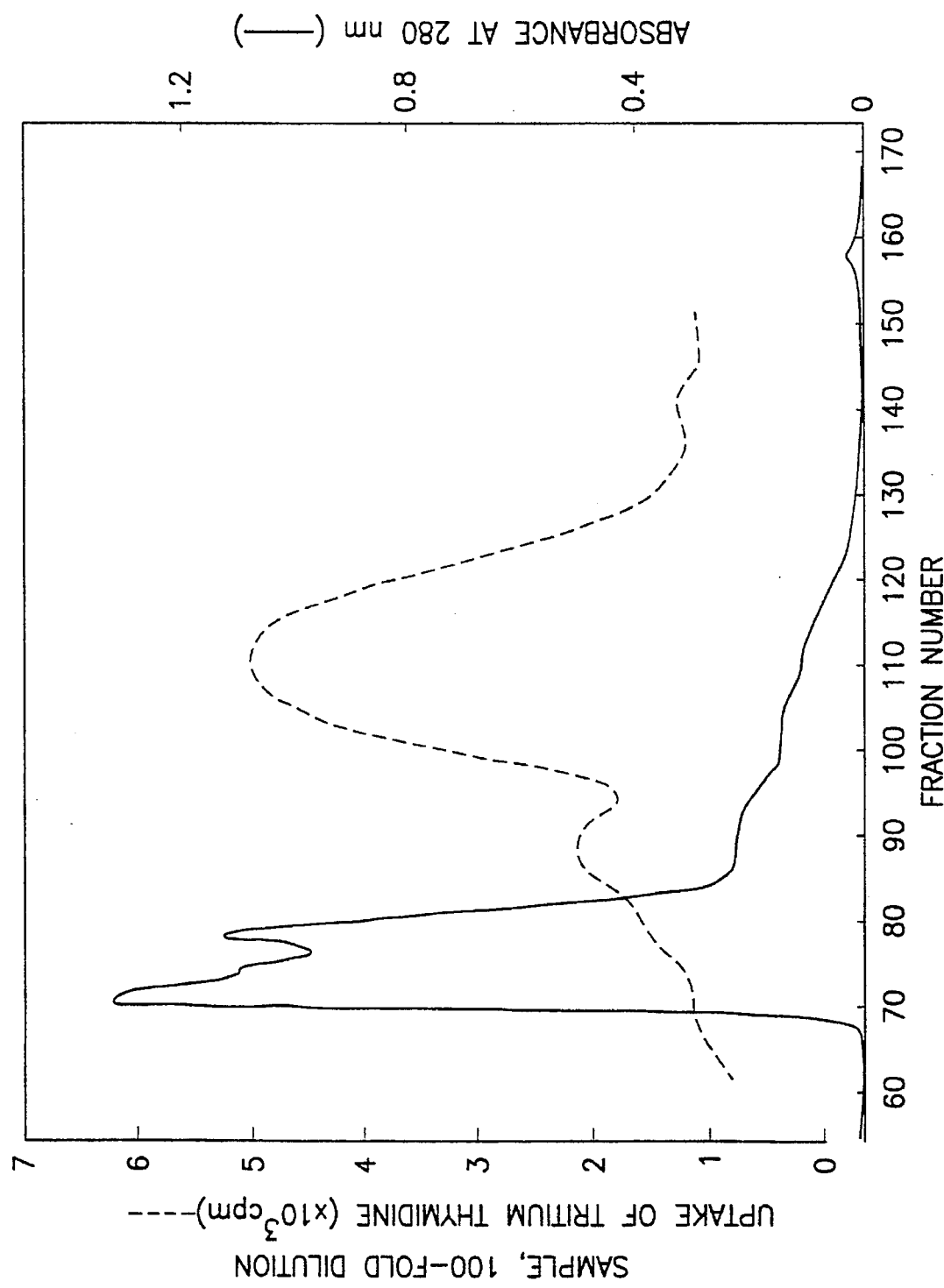
FIG. 2 shows elution patterns of protein and activity on Sephacryl S-200 HR column (Example 1-(2), step 3)

About 35 ml of the solution concentrated in step 2 was placed on a Sephacryl S-200HR column (bed volume: 1787 ml, 5 cm in internal diameter×91 cm in length, Pharmacia LKB Biotechnology), and eluted and fractionated with 20 mM Tris-HCl buffer supplemented with 0.5M NaCl and 0.1% CHAPS (85 ml/hour, 10 ml/fraction, 4° C.) (FIG. 2). For each fraction, the growth promoting activity to glial cells was assayed by the method described in Reference Example 1, and fractions exhibiting the activity (fractions 105 to 117) were pooled. To acquire a greater amount of GAF protein, further, 55 liter of the NMC-G1 culture supernatant was divided into two parts, and steps 1 to 3 were each conducted for each part and combined sample was used for following purification steps.

Step 4: Heparin affinity column chromatography

Figure 3:
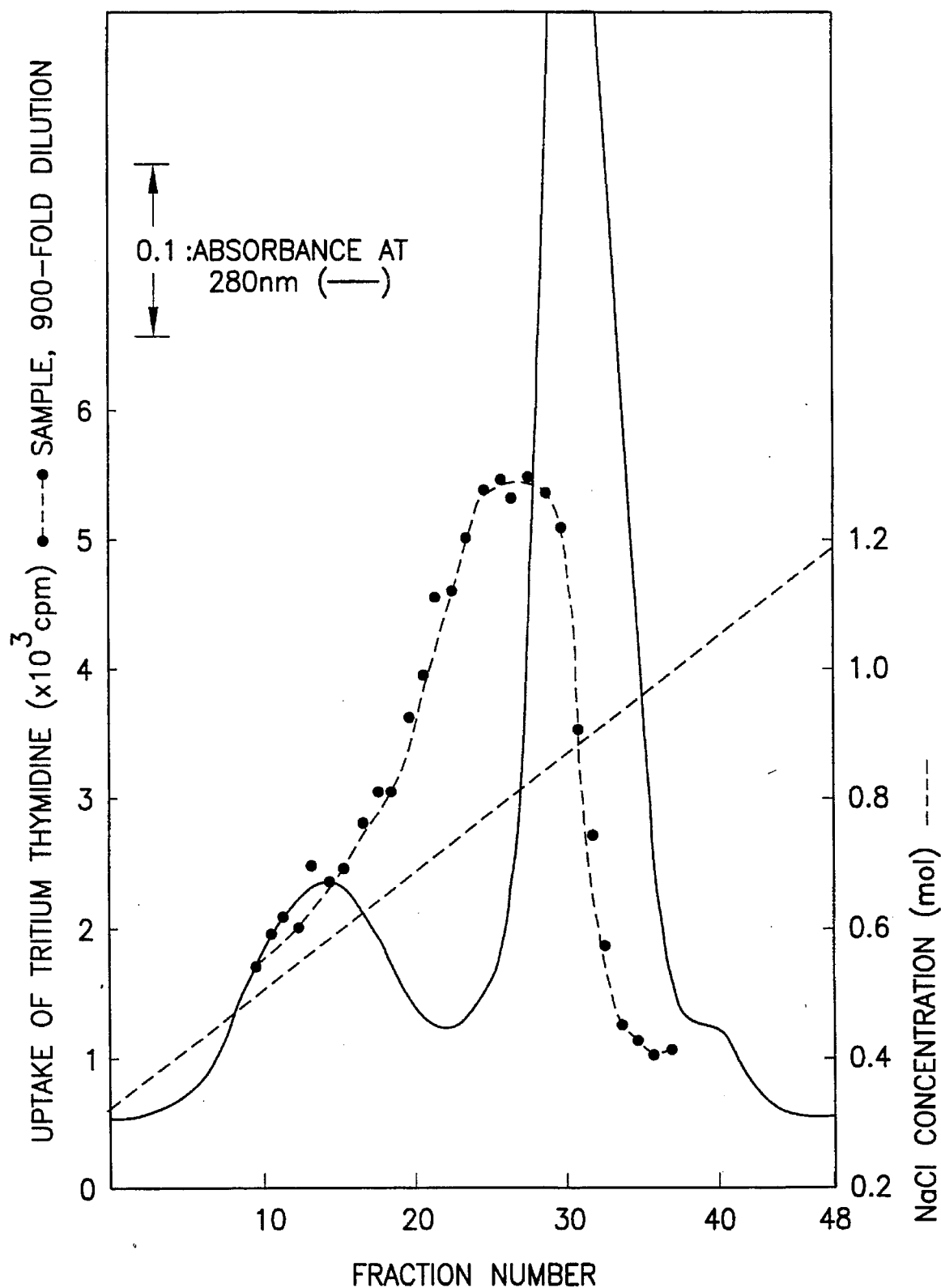
FIG. 3 shows elution patterns of protein and activity on heparin-Sepharose (registered trade mark) CL-6B column (Example 1-(2), step 4)

The active fractions obtained by three operations of gel filtration chromatography in step 3 were pooled (390 ml). To the solution thus pooled were added 99 ml of 100% glycerin, 2.61 ml of 10% CHAPS, 5.22 ml of 1M Tris-HCl buffer (pH 7.6) and 154 ml of water (651 ml in total). This solution was loaded onto a heparin-Sepharose (registered trade mark) CL-6B column (bed volume: 5.8 ml) pre-equilibrated with 20 mM Tris-HCl buffer (pH 7.6) containing 0.3M NaCl, 0.1% CHAPS and 15% glycerin, at a flow rate of 25 ml/hour at 4° C. The column was washed with 80 ml of 20 mM Tris-HCl buffer (pH 7.6) containing 0.3M NaCl, 0.1% CHAPS and 15% glycerin, at a flow rate of 25 ml/hour at 4° C., and then, the adsorbed protein was eluted and fractionated by linearly increasing the concentration of NaCl. The salt concentration gradient was produced by gradually adding 50 ml of 20 mM Tris-HCl buffer (pH 7.6) containing 1.2M NaCl, 0.1% CHAPS and 15% glycerin to 50 ml of 20 mM Tris-HCl buffer (pH 7.6) containing 0.3M NaCl, 0.1% CHAPS and 15% glycerin (25 ml/hour, 2 ml/fraction, 4° C.) so that the salt concentration gradually rose from 0.3M to 1.2M over the course of the elution (FIG. 3).

Step 5: Heparin affinity high performance liquid column chromatography

Figure 4:
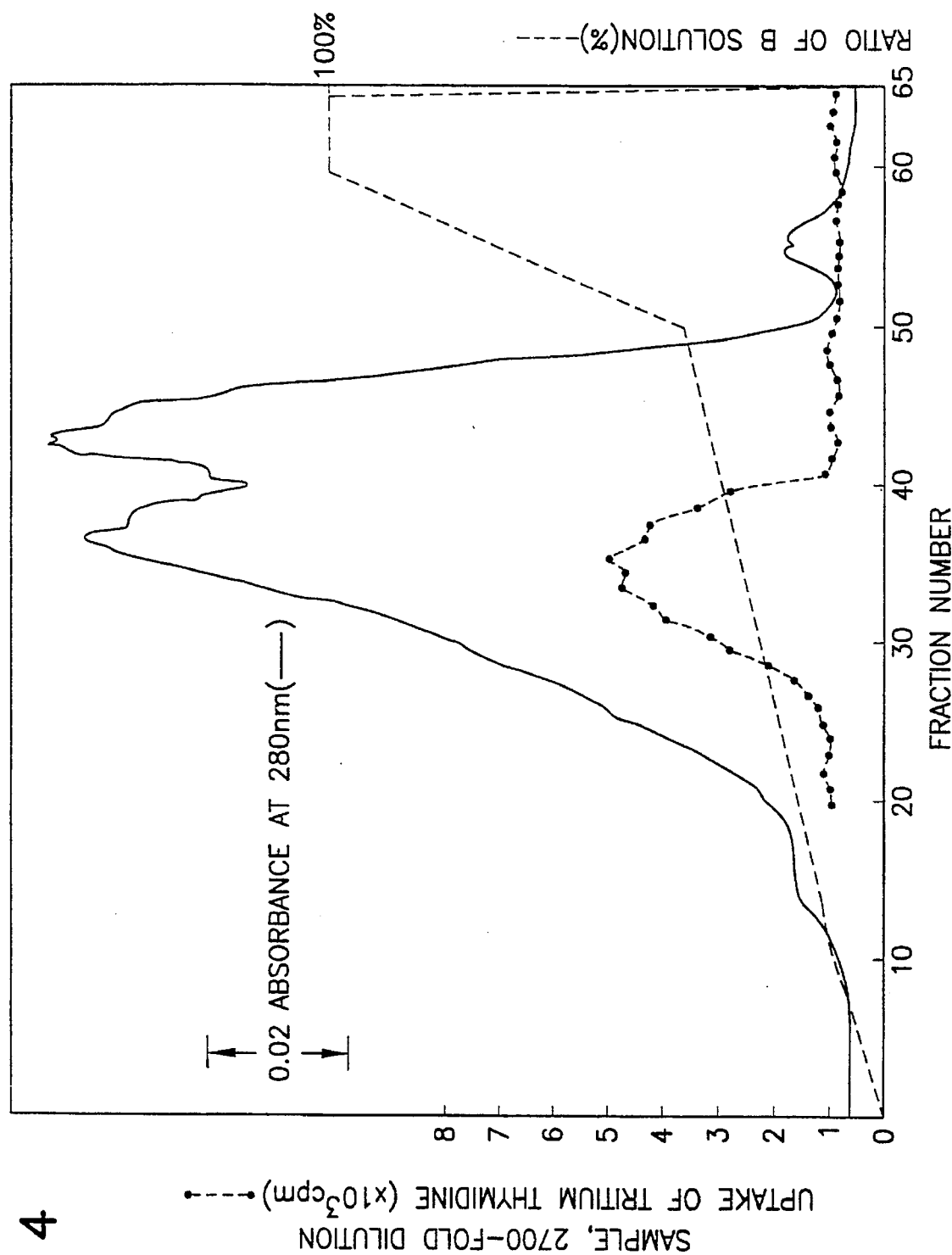
FIG. 4 shows elution patterns of protein and activity on HR-894 heparin affinity high performance liquid (Example 1-(2), step 5)

The active fractions having growth promoting activity to glial cells obtained in step 4 (fractions 23 to 30) were pooled, and 32 ml of 20 mM Tris-HCl buffer (pH 7.6) containing 0.1% CHAPS and 15% glycerin was added to 16 ml of the pooled solution. Of the 48 ml of this solution, 46 ml was subjected to high performance liquid chromatography (Varian model 5040 system, Varian Associates, California, U.S.A.) equipped with an HR-894 column (8 mm in diameter×50 mm in length, Showa Denko K. K., Japan). The protein adsorbed to the resin was eluted at a flow rate of 1 ml/minute by linearly increasing the concentration of NaCl and fractionated (1 ml/fraction). Buffer A used was 20 mM Tris-HCl buffer (pH 7.6) containing 0.2M NaCl, 0.1% CHAPS and 15% glycerin, and buffer B was 20 mM Tris-HCl buffer (pH 7.6) containing 2M NaCl, 0.1% CHAPS and 15% glycerin. The program of elution was as follows:

0 minute (100% A) - 10 minutes (90% A+10% B) - 15 minutes (90% A+10% B) - 50 minutes (65% A+35% B) - 60 minutes (100% B) - 64 minutes (100% B) - 65 minutes (100% A). The concentration gradient produced by this program is depicted in FIG. 4. The column temperature was room temperature.

Step 6:-Reverse phase high performance liquid column chromatography

Figure 5:
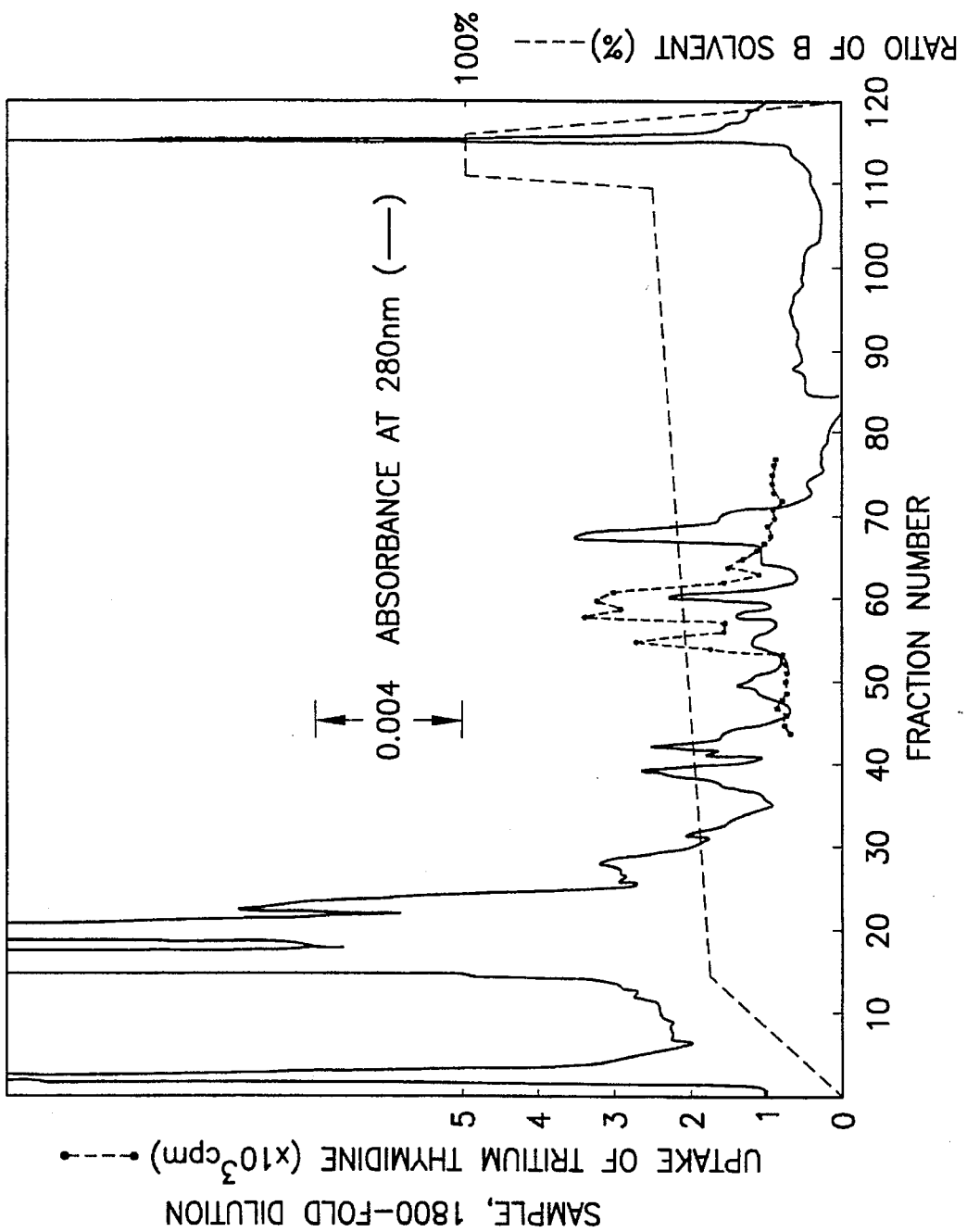
FIG. 5 shows protein and activity elution patterns by Vydac C4 high performance liquid (Example 1-(2), step 6)

The active fractions obtained in step 5 (fractions 32 to 38) were pooled, and 1.75 ml of 0.5M phosphate buffer (pH 6.0) was added to 7 ml of the pooled solution. Of 8.75 ml of this solution, 8 ml was applied to high performance liquid chromatography (Varian model 5040 system) equipped with a Vydac C4 column (0.46 cm in diameter×25 cm in length, Vydac, California, U.S.A.). The adsorbed protein was eluted at a flow rate of 0.8 ml/minute by linearly increasing the concentration of acetonitrile to fractionate (0.8 ml/fraction). Solvent A used was 0.1% trifluoroacetic acid (TFA)-99.9% water, and solvent B was 0.1% TFA-90% acetonitrile. The program of elution was as follows:

0 minute (100% A) - 15 minutes (65% A+35% B) - 110 minutes (50% A+50% B) - 112 minutes (100% B) - 117 minutes (100% B) - 120 minutes (100% A). The concentration gradient produced by this program is depicted in FIG. 5. The column temperature was room temperature.

After fractionation, acetonitrile was evaporated by a Speedback concentrator (Model A290, Servant, U.S.A.). Then, distilled water was added thereto to adjust all fractions to a volume of 0.5 ml.

Figure 6:
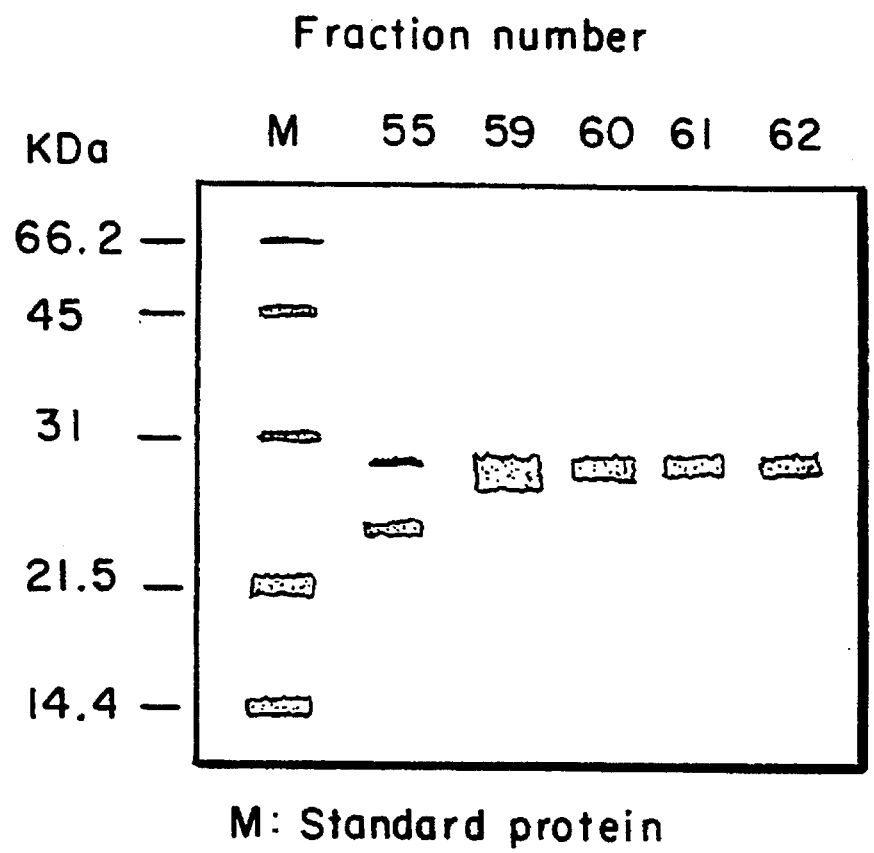
FIG. 6 is an SDS polyacrylamide gel electrophoresis diagram of a purified glia activating factor (derived from NMC-G1)

The active fractions (fractions 55, 59, 60, 61 and 62) were subjected to SDS-polyacrylamide gel electrophoresis in the presence of 2-mercaptoethanol, followed by silver staining. Results thereof are shown in FIG. 6. Each fraction gives a single band at 25 kDa (fraction 55), 29 kDa (fractions 59 and 60) or 30 kDa (fractions 61 and 62). These three bands correspond to GAF proteins having molecular weights of about 25,000, about 29,000 and about 30,000, respectively.

(3) Summary of Purification

The summary of purification of 33 liters of the NMC-G1 culture supernatant is shown in Table 1.

Example 2

Activity of GAF to Various Culture Cells (1)

(1) GAF's Growth Promoting Activity upon Glial Cells

Figure 7:
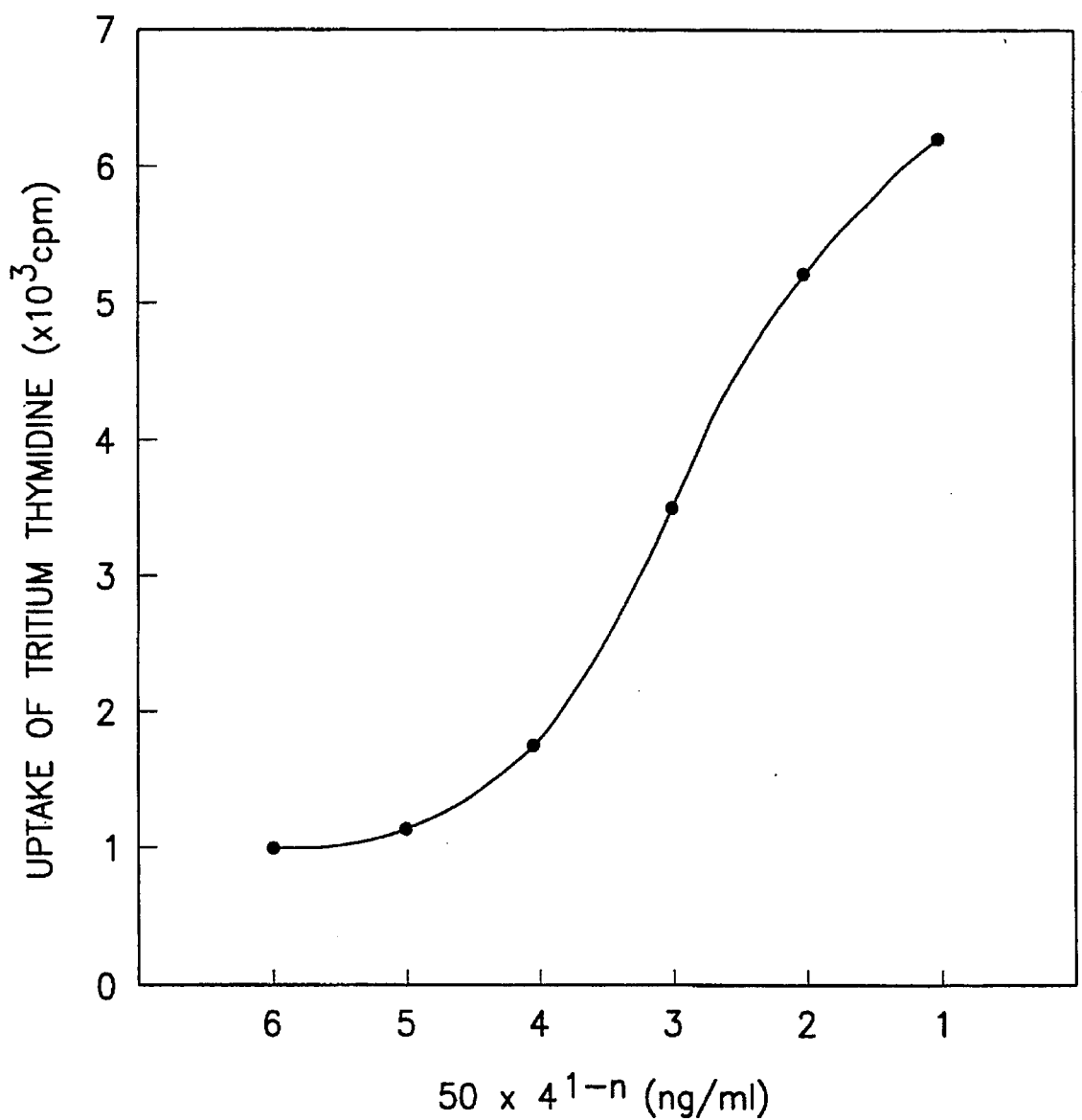
FIG. 7 is a graph showing growth promoting activity of the purified glia activating factor to glial cells.

The purified GAF obtained by the method described in Example 1, Steps 1–6, displays growth promoting activity upon glial cells as shown in FIG. 7. In FIG. 7, the values on the abscissa indicate GAF concentration, wherein the concentration designated by the value "6" is $50 \times 4^{1-6}$ ng/ml. The growth promoting activity upon glial cells was assayed according to the method described in Reference Example 1.

Figure 8:
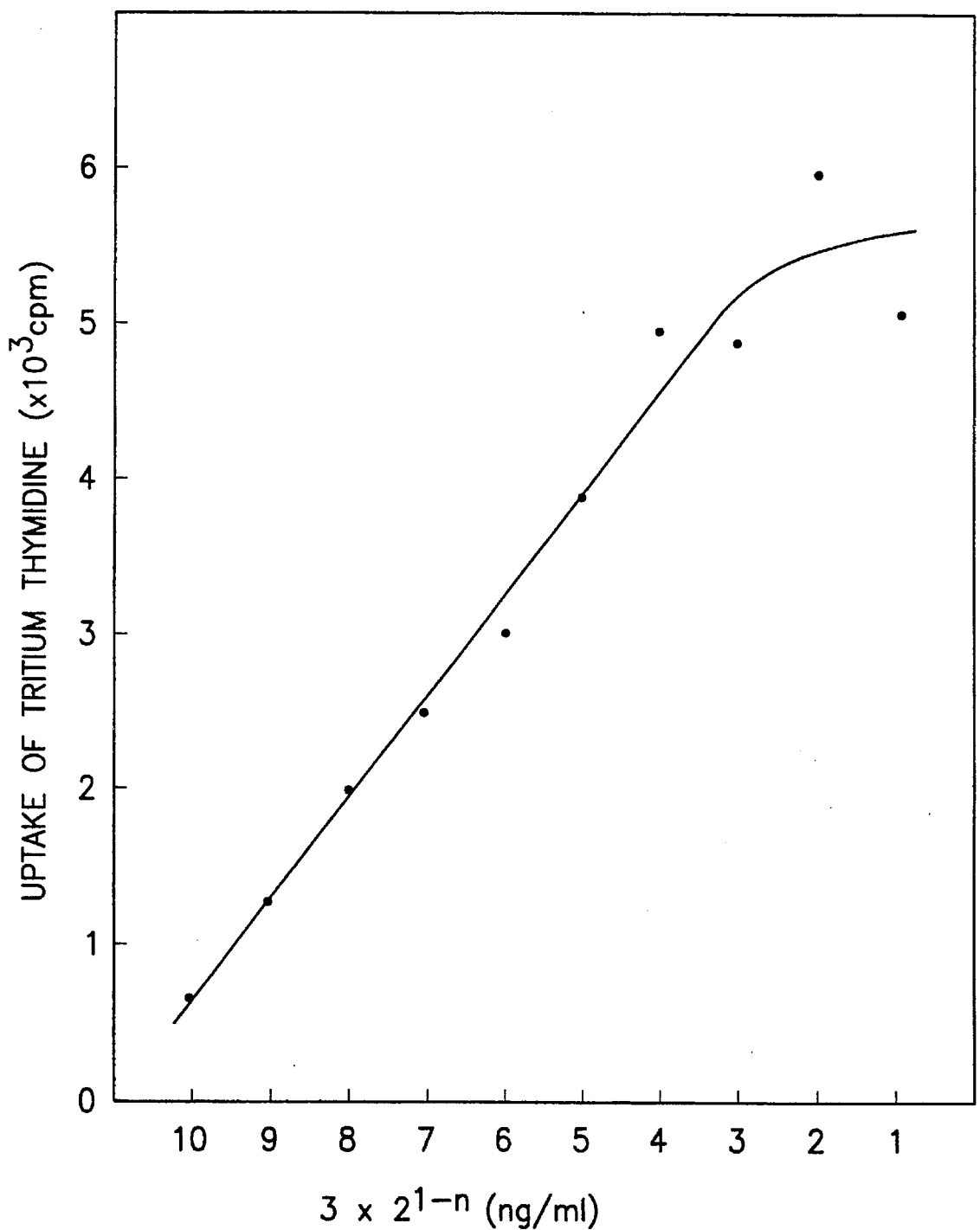
FIG. 8 is a graph showing growth promoting activity of the NMC-G1-derived purified glia growth activating factor to the glial cells, which is assayed again after purification using reversed phase high performance liquid chromatography.

To avoid inactivation caused by storage, the growth promoting activity to glial cells was assayed using the purified sample immediately after the operations of reverse phase high performance liquid column chromatography and the removal of acetonitrile, the final step of the purification process. Results thereof are shown in FIG. 8. In this figure, the values on the abscissa indicate GAF concentration.

The results shown in FIGS. 7 and 8 report slightly different values for the GAF concentration giving a 50% uptake of tritium thymidine. This discrepancy is believed to be due to partial inactivation of one of the samples. Namely, FIG. 7 shows the results obtained when the sample stored at

TABLE 1

| Sample | Total protein amount (mg) | Total activity (U) | Specific activity (U/mg) | Activity Recovery (%) | Purification |
|---|---|---|---|---|---|
| Heparin 2M NaCl eluent | 221 | $177 \times 10^3$ | $8.0 \times 10^2$ | 100 | 1 |
| Concentrated (YM-10) | 217 | $216 \times 10^3$ | $1.0 \times 10^3$ | 122 | 1.3 |
| Sephacryl S-200HR | 17.3 | $126 \times 10^3$ | $7.3 \times 10^3$ | 71 | 9.1 |
| Heparin column (second) | 2.12 | $60.6 \times 10^3$ | $2.9 \times 10^4$ | 34 | 36 |
| Heparin HPLC Reverse phase HPLC | 0.453 | $34.5 \times 10^3$ | $7.6 \times 10^4$ | 20 | 95 |
| M.W. 25,000 | 0.0003* | $1.84 \times 10^3$ | $6.1 \times 10^6$ | 1.1 | 7,600 |
| M.W. 29,000 | 0.0002* | $1.26 \times 10^3$ | $6.3 \times 10^6$ | 0.7 | 7,900 |
| M.W. 30,000 | 0.0011* | $4.85 \times 10^3$ | $4.4 \times 10^6$ | 2.8 | 5,500 |

The biological activity was assayed by the method described in Reference Example 1. Total activity (U) is expressed as the reciprocal of the dilution ratio of the sample having a 50% uptake value of tritium thymidine, wherein a 100% uptake value of tritium thymidine is defined as the uptake of tritium thymidine in a medium of 10% fetal calf serum. Total protein amount in mg was calculated using a standarized absorbance of 1.0 at 280 nm for a solution having a protein concentration of 1 mg/ml. Where the total protein amount is shown with a "*", this amount was determined based on the stain density of the silver-stained band on the polyacrylamide gel compared with that of standard protein.

−80° C. after purification was used. It is therefore presumed that the GAF protein in this sample was degeneratedly inactivated by the freeze-thawing operation of the low concentration protein solution, or adsorbed by the vessel.

(2) Glial Cell Growth Promoting Activity

After addition of GAF, glial cell growth was examined according to the following method.

The glial cells were suspended in DMEM medium supplemented with 10% inactivated fetal calf serum at $3 \times 10^4$ cells/ml, and 500 μl thereof was poured into each well of a 24-well culturing plate (Linbro, U.S.A.). Cell culture was conducted for 3 days. Then, 440 μl of the medium was discarded from each well, and 340 μl of fresh DMEM medium was added to each well. Subsequently, the following wells were prepared: wells in which 50 μl of a 50-fold diluted GAF active fraction obtained by the heparin affinity column chromatography described in Example 1-(2), step 4 in DMEM medium supplemented with 1.25% inactivated fetal calf serum was added, wells in which 50 µl of a 500 µg/ml solution of heparin in the same medium was added, wells in which both were added, and wells in which none was added as a control group.

Figure 9:
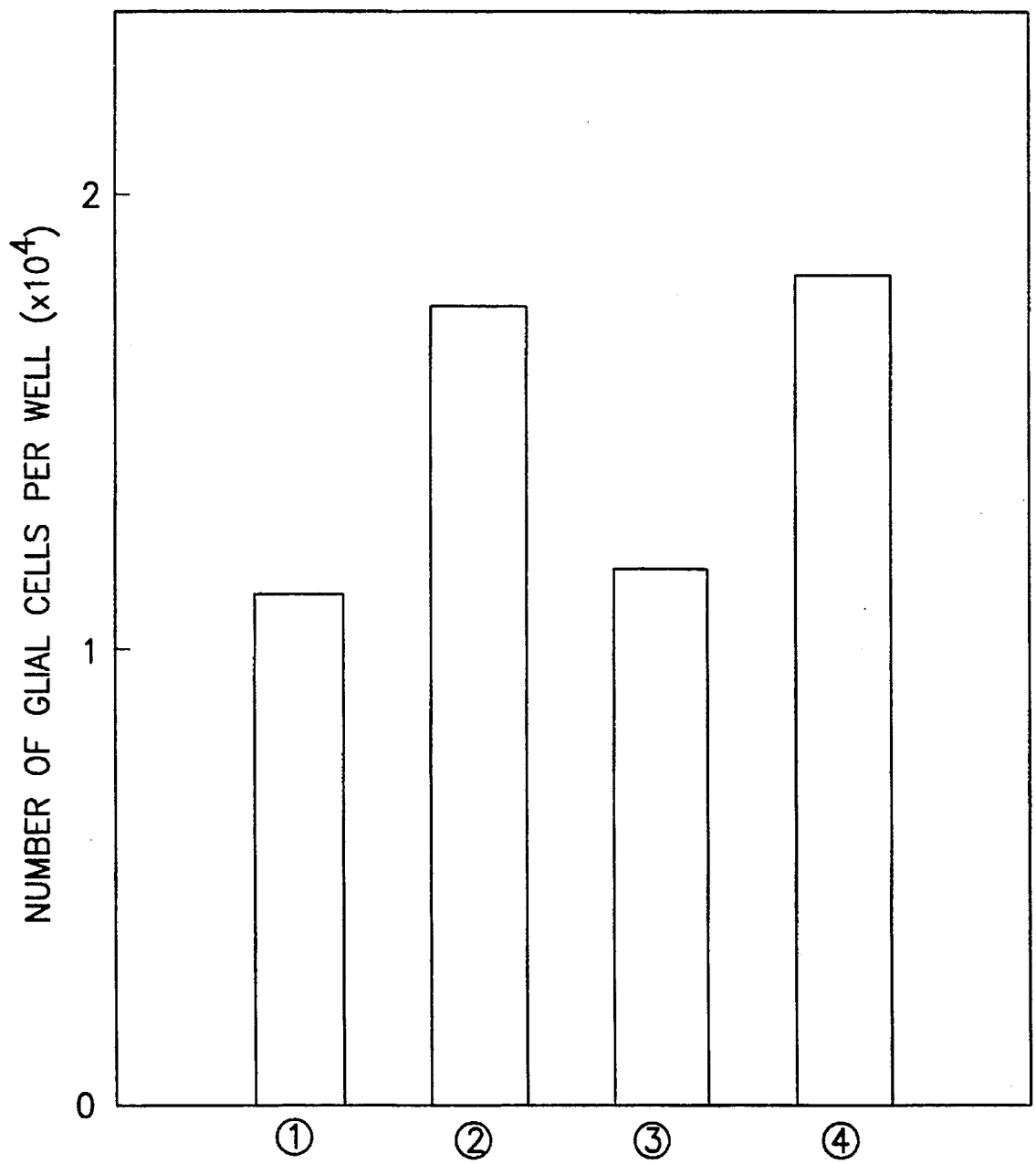
FIG. 9 is a graph showing increases in glial cell number by the glia activating factor (derived from NMC-G1)

All of the above mentioned wells were adjusted with DMEM medium supplemented with 1.25% inactivated fetal calf serum to give a final volume of 500 µl, followed by further culturing for 2 days. After culturing, each well was washed twice with 3 ml of DMEM medium, and then 0.5 ml of PBS containing 0.2% trypsin and 0.01% EDTA was added thereto to detach the cells. The number of cells of each well was counted using a Coulter Cell Counter (Type ZM, Coulter). Results are shown in FIG. 9. The number of the glial cells was increased 1.6 times by the addition of GAF, as compared to the groups containing no GAF. However, it appears that the addition of heparin to the wells did not affect glial cell growth.

(3) Time Course of Glial Cell Growth Promoting Activity

Figure 10:
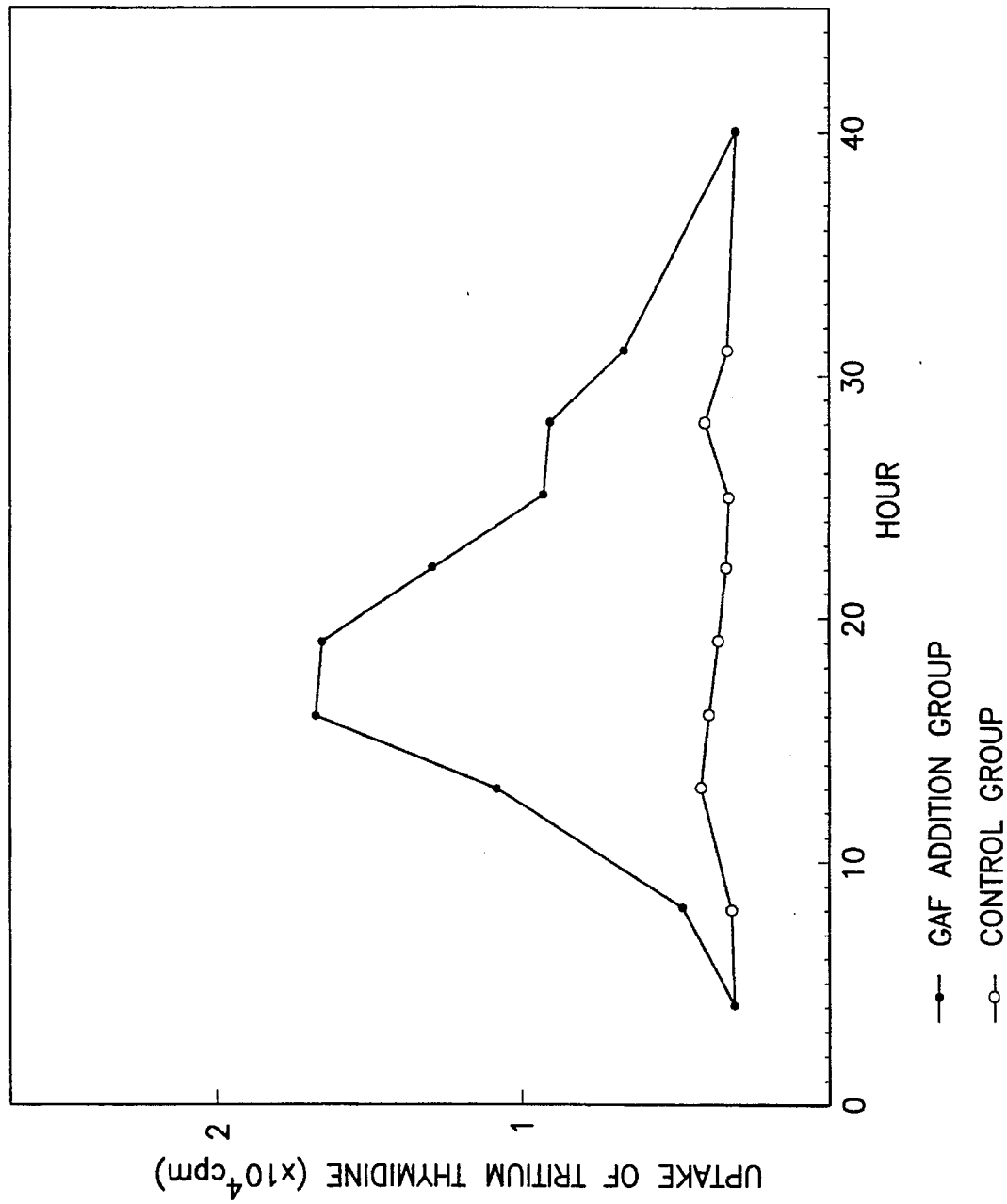
FIG. 10 is a graph showing time course of tritium thymidine incorporation into the glial cells by the glia activating factor (derived from NMC-G1), wherein —●— indicates a group to which GAF is added and —O— indicates a control group to which GAF is not added.

The time course of glial cell growth promoting activity were examined according to the method described in Reference Example 1, except for the following. Namely, GAF active fractions obtained by the heparin affinity high performance liquid column chromatography described in Example 1-(2), step 5 was diluted 800 times with DMEM medium supplemented with 1.25% inactivated fetal calf serum, and 20 µl of the resulting sample was added to each well. Then, 1 µCi of tritium thymidine was added to each well after 4, 8, 13, 16, 19, 22, 25, 28, 31 and 40 hours, respectively. The cells were harvested after 3 hours, and the amount of tritium thymidine taken into the cells was measured with a liquid scintillation counter. The same procedure was repeated for a control well. Results are shown in FIG. 10. The uptake of tritium thymidine reached a peak 16 to 19 hours after addition of the GAF.

(4) Growth Promoting Activity to Fibroblasts

Figure 11:
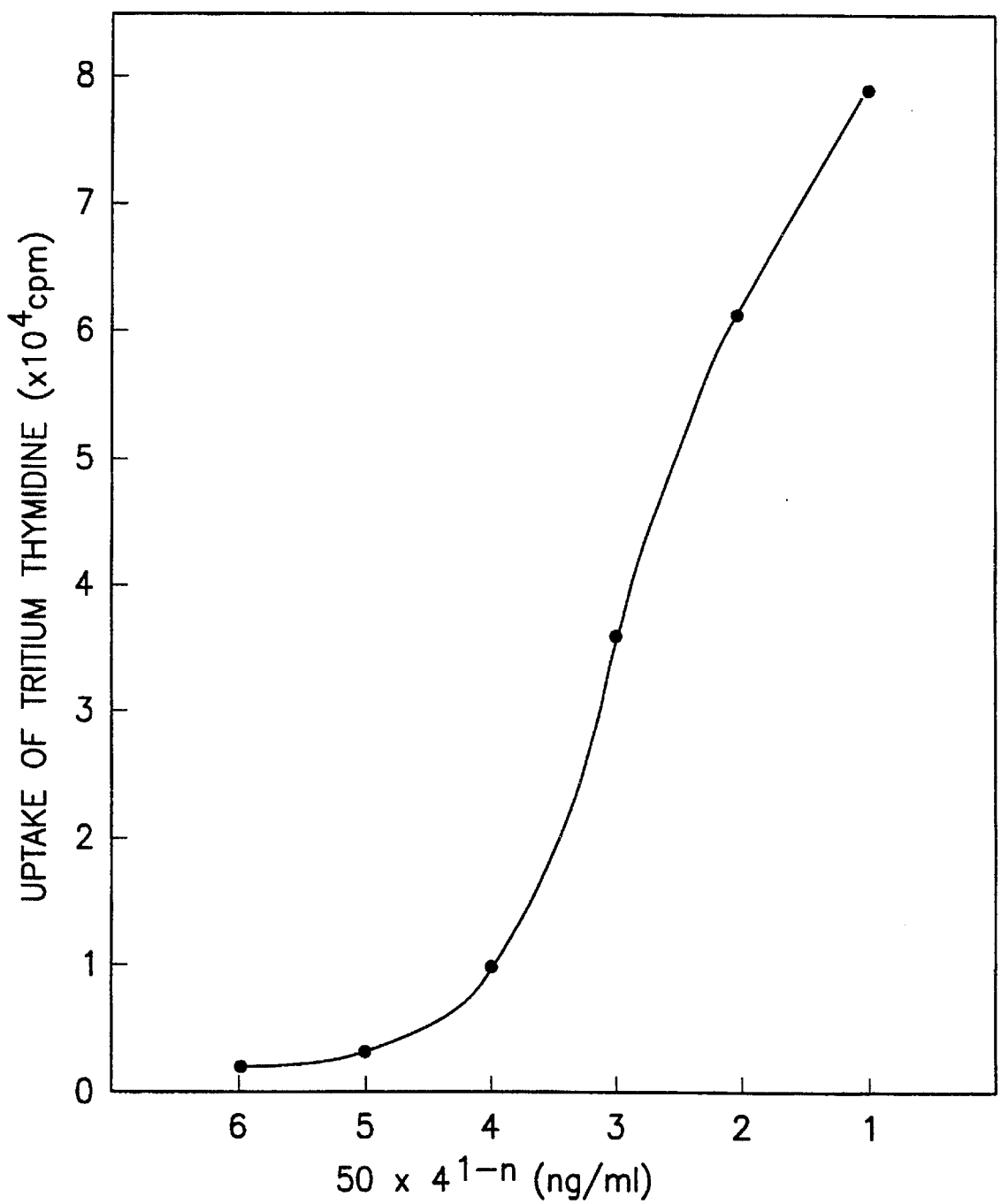
FIG. 11 is a graph showing growth promoting activity of the purified glia activating factor (derived from NMC-G1) upon fibroblast mouse BALB/3T3 clone A31 cells.

As shown in FIG. 11, the purified GAF obtained by the method described in Example 1, Steps 1–6 imparts growth promoting activity upon fibroblast mouse BALB/3T3 clone A31 cells. In the figure, the values on the abscissa indicate GAF concentration. The growth promoting activity of GAF upon A31 cells was assayed according to the following method.

$2 \times 10^3$ mouse BALB/3T3 clone A31 cells were added along with 75 µl of DMEM medium supplemented with 5% calf serum into each well of a Nunc 96-well microtiter plate (flat-bottomed), and cultured. The next day, 50 µl of the medium was discarded from each well, and 175 µl of serum-free DMEM medium was added to each well. After cultivation for 3 to 4 days, 20 µl of the medium was discarded from each well. Then, 20 µl of the test sample appropriately diluted with DMEM medium supplemented with 1.25% inactivated fetal calf serum was added to each well, followed by culturing overnight. The next morning, 1 µCi of tritium thymidine (5 Ci/mmol, 1 mCi/ml, RCC Amersham) was added to each well, followed by further culturing for 5 to 7 hours. After culture, each well was washed with 1 ml of PBS, and then 100 µl of 5% SDS solution was added thereto, followed by standing overnight at 37° C. A cell extract of each well was collected in a tube, and the amount of tritium thymidine taken into the cells was measured with a scintillation counter.

Figure 12:
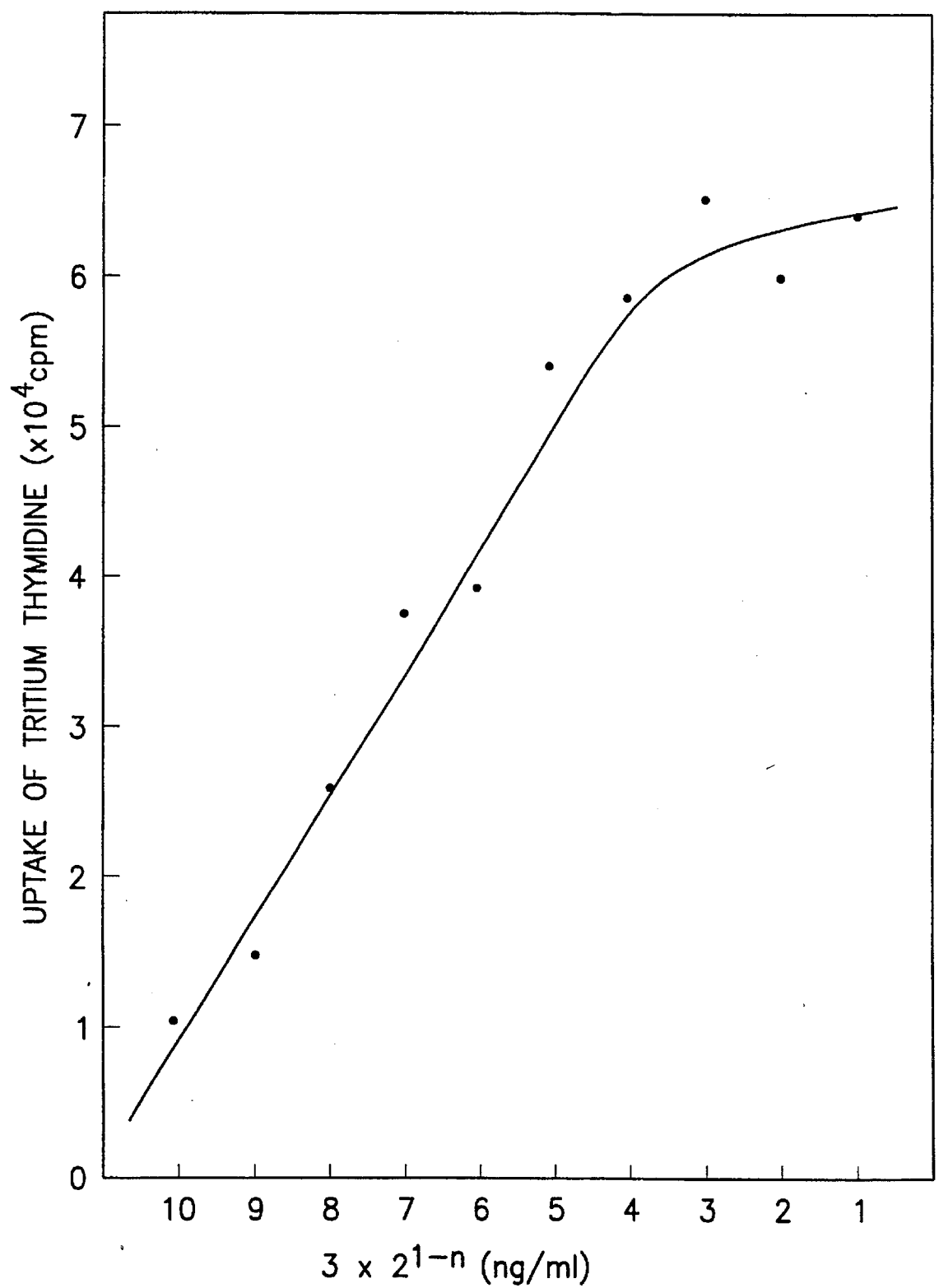
FIG. 12 is a graph showing growth promoting activity of the purified glia-activating factor (derived-from NMC-G1) upon mouse BALB/3T3 clone A31 cells, which is assayed again after purification using reversed phase high performance liquid chromatography.

To avoid inactivation by the storage, GAF's growth promoting activity upon A31 cells was assayed using the purified sample immediately after the operations of reverse phase high performance liquid column chromatography and the removal of acetonitrile, the final step of the purification process. Results thereof are shown in FIG. 12. In the figure, the values on the abscissa indicate GAF concentration.

The results shown in FIGS. 11 and 12 report slightly different values for the GAF concentration giving a 50% uptake of tritium thymidine. This discrepancy is believed to be due to partial inactivation of one of the samples. Namely, FIG. 11 shows the results obtained when the sample stored at −80° C. after purification was used. It is therefore presumed that the GAF protein was degeneratedly inactivated by the freeze-thawing operation of the protein solution, or adsorbed by the vessel.

(5) Activity to Human Umbilical Vascular Endothelial Cells

Figure 13:
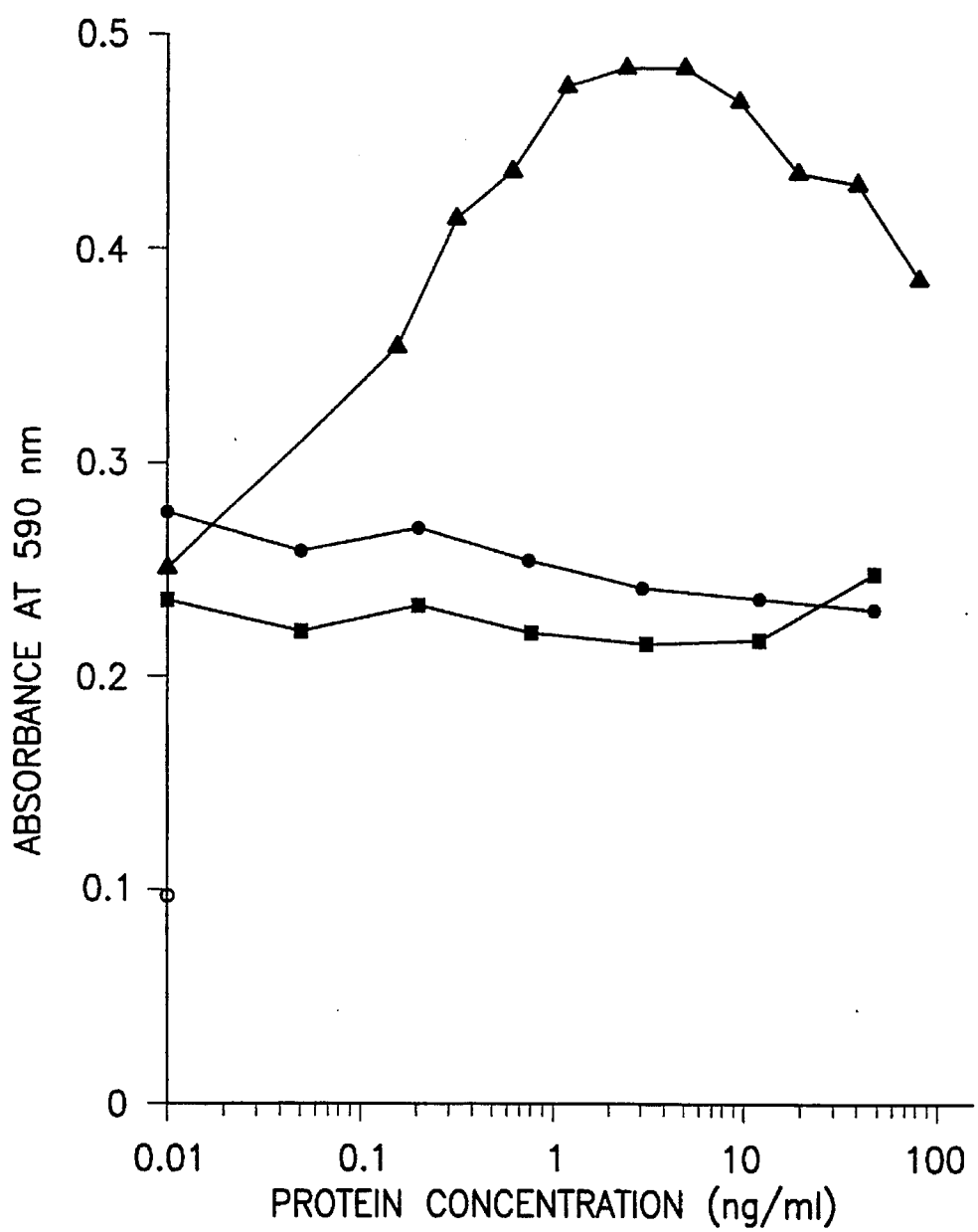
FIG. 13 is a graph showing growth promoting activity of the purified glia activating factor (derived from NMC-G1) upon human umbilical vascular endothelial cells.

The growth promoting activity of GAF upon human umbilical vascular endothelial cells was determined by comparing it to that of bFGF. This comparison indicated that the purified GAF obtained by the method described in Example 1, Steps 1–6 does not display growth promoting activity upon human umbilical vascular endothelial cells as shown in FIG. 13. In the figure, the values on the abscissa indicate the protein concentration of GAF or bFGF.

The growth promoting activity to human umbilical vascular endothelial cells was assayed according to the following method. Human venous vascular endothelial cells (hereinafter referred to as HUVE cells) isolated from the human umbilical cords were used for this assay. Further, the well known MTT assay was used for measurement of the cell proliferation degree. However, this assay method was modified in accordance with Tada et al. [*J. Immunol. Methods*, 93, 157 (1986)]. Namely, the HUVE cells maintained under the passage were dissociated into single cells by the use of a 0.125% trypsin solution (Boehringer Mannhaim) containing 0.002% EDTA (345-01882, Dotite), and the resulting cells were suspended in medium comprising GIT medium (398-00515, Nippon Seiyaku) supplemented with 2.5% fetal calf serum (Whittakar Bioproduct). The number of the cells contained in this cell suspension was counted using a Coulter Cell Counter (Type ZM, Coulter), and the suspension was subjected to the following cell culture: 100 µl of the suspension containing $2 \times 10^3$ HUVE cells was added to each well of a 96-well culture dish (F96, Nunc), followed by culturing at 37° C. (Hitachi $CO_2$-$N_2$ control incubator, CH-16 type, $CO_2$: 5%, $O_2$: 7%).-The day after culturing, test samples (FIG. 13) were added to the HUVE cell culture. Heparin (Sigma, U.S.A.) was further added to produce a final concentration of 5.0 ug/ml to 20 µg/ml. After addition of the sample, culturing was conducted for further 3 days. The medium was removed from the culture well, and 100 µl of HUVE medium supplemented with 1.0 mg/ml MTT reagent (34101823, Dotite) was added to the well, followed by maintenance at 37° C. for 4 hours. Then, 100 ul of a 10% SDS (Wako Pure Chemical Industries) solution was added thereto, and maintained for 4 hours at constant temperature of 37° C. After termination of reaction, the 96-well culture dish containing the reaction solution was shaken, and its absorbance at 590 nm was measured by use of a microtiter plate absorbance measuring instrument (MCC 341, Titertek).

(6) Activity to Rat Pheochromocytoma PC-12 Cells

Figure 14:
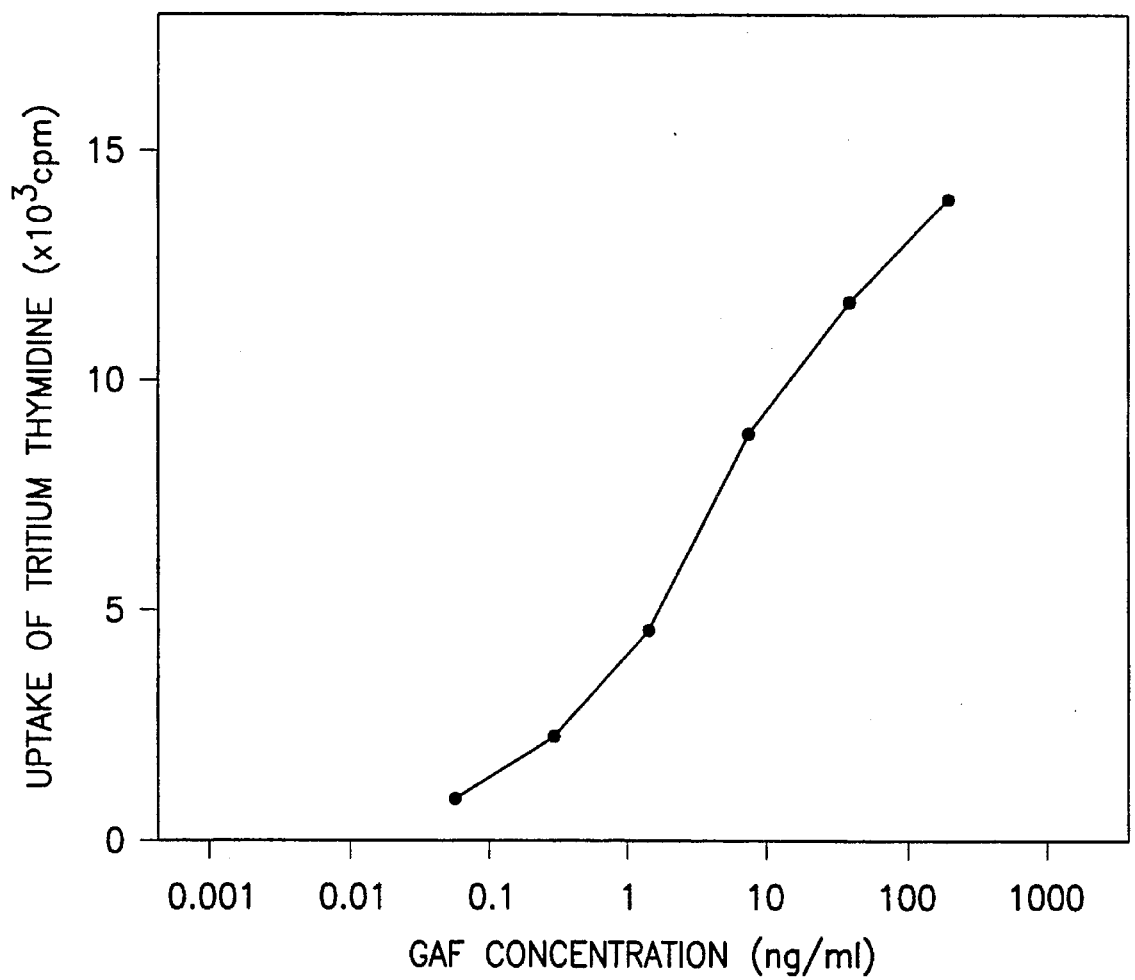
FIG. 14 is a graph showing tritium thymidine incorporation promoting activity of the purified glia activating factor (derived from NMC-G1) upon rat adrenal melanocytoma-derived PC-12 cells.

As shown in FIG. 14, the purified GAF obtained by the method described in Example 1, Steps 1–6 has growth promoting activity upon rat pheochromocytoma PC12 cells. In the figure, the values on the abscissa indicate the GAF concentration.

The growth promoting activity to PC-12 cells was assayed according to the following method. GAF was appropriately diluted with RPMI-1640 medium supplemented with 1% inactivated horse serum, and 50 μl of the resulting solution was poured into each well of a 96-well microtiter plate. Next, PC-12 cells were suspended in RPMI-1640 medium supplemented with 1% inactivated horse serum to give $10^6$ cells/ml, and 50 μl of the cell suspension was poured into each well of a 96-well flat-bottomed microtiter plate (A/N Nunc, Roskilde, Denmark), followed by further culturing for 2 days. After culturing, 5 μCi of tritium thymidine (5 Ci/mmol, 1 mCi/ml, RCC Amersham) was added to each well, followed by culturing for further 5 hours. After culturing, the cells were collected on a glass fiber filter using a Titertek Cell Harvester, and washed with water. Then, the the amount of tritium thymidine taken into the cells was measured by a liquid scintillation counter.

(7) Stability of Activity

Figure 15:
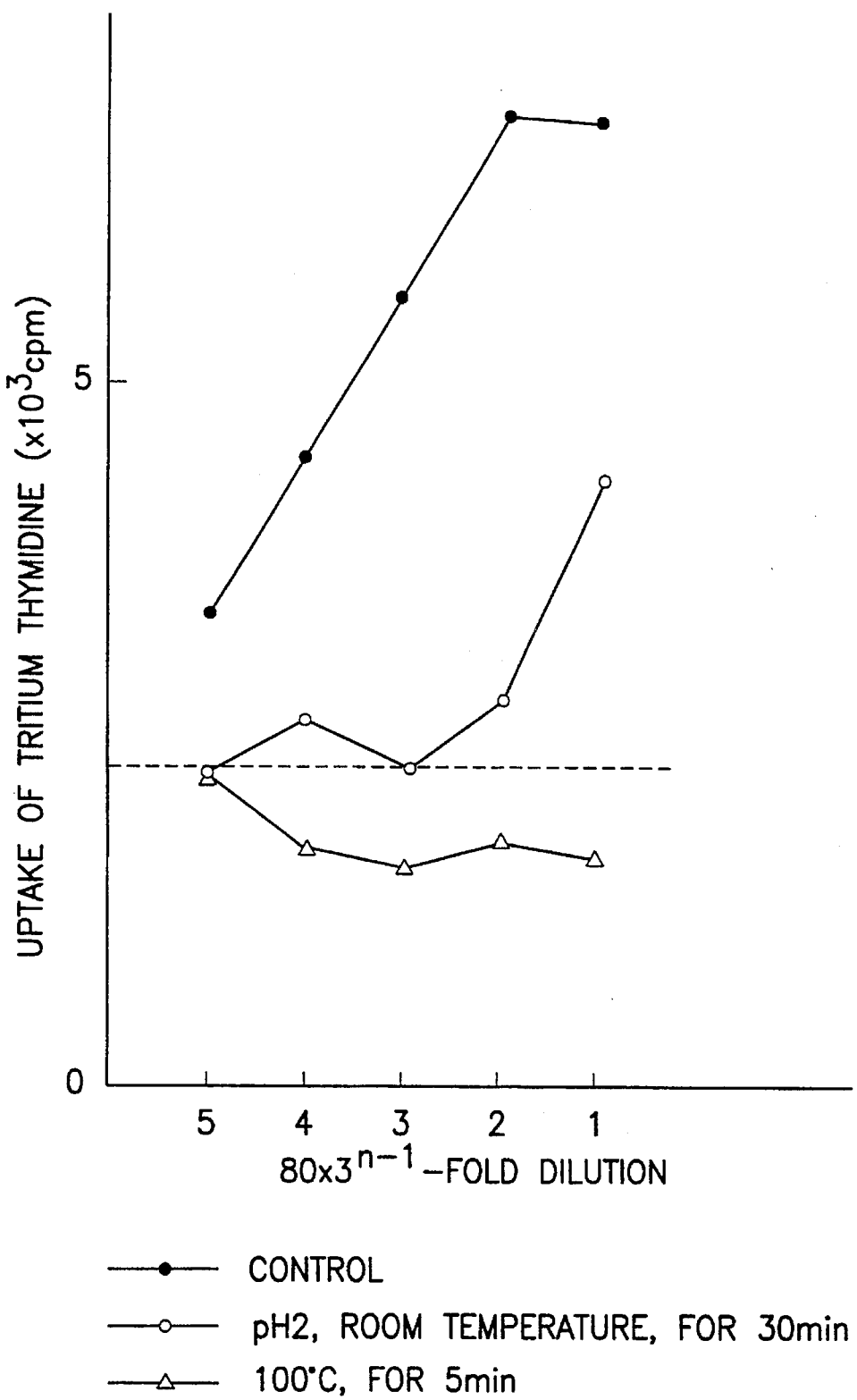
FIG. 15 is a graph showing heat and acid stabilities of glia activating factor (derived from NMC-G1)

When the 2M NaCl fractions eluted from a heparin-Sepharose (registered trade mark) CL-6B column (Example 1-(2), step 1) were heat treated at 100° C. for 5 minutes, the activity was completely lost. Further, when they were treated at pH 2 at room temperature for 30 minutes, the activity was partially lost. These phenomena are shown in FIG. 15. In the figure, the values on the abscissa indicate the dilution of GAF. Control means the untreated GAF. Dashed line indicates the tritium thymidin incorporation level without GAF.

(8) Antigenicity: Immunological Cross Reaction of GAF with aFGF and bFGF

Figure 16:
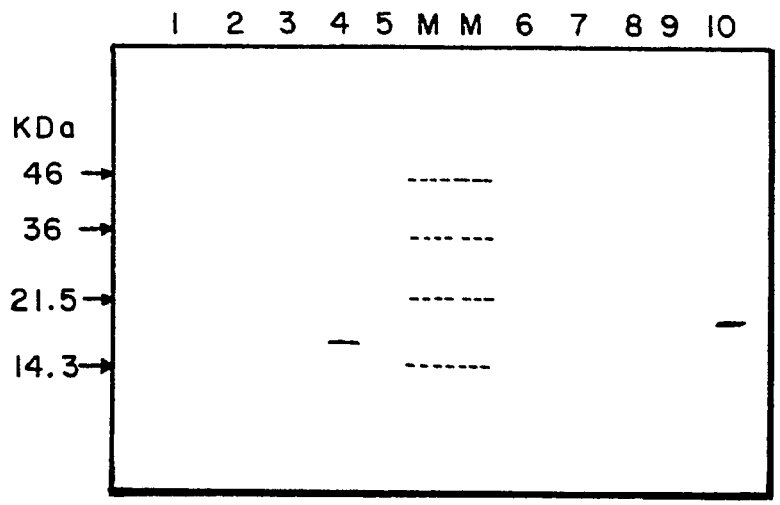
FIG. 16 is a diagram showing the immunological cross reaction of the glia activating factor (derived from NMC-G1) with aFGF and bFGF.

A sample purified according to the method described in Example 1, Steps 1–6, was subjected to Western Blotting using rabbit anti-aFGF polyclonal anti-serum and rabbit anti-bFGF IgG. As seen from FIG. 16, the GAF did not cross react either aFGF or bFGF.

Example 3

Property of GAF Protein Produced by NMC-G1 Cells 30 ug of 25 kDa GAF, 30 ug of 29 kDa GAF and 60 ug of 30 kDa GAF as obtained in Example 1 were subjected to SDS-polyacrylamide gel electrophoresis, and then transferred onto a ProBlott membrane (Applied Biosystems, California, U.S.A.) by use of a dry-type blotting apparatus (ATTO, Tokyo, Japan). The membrane was immersed in a phosphate buffer-NaCl solution (8 g/l NaCl, 0.2 g/l KCl, 1.15 g/l $Na_2HPO_4$, 0.2 g/l $KH_2PO_4$, pH 7.4) supplemented with a 2% PVP- 360 solution (2% polyvinylpyrrolizone-360, Sigma, U.S.A.) for 45 minutes with shaking, and then, transferred into a 2% PVP-360 solution containing biotinyl concanavalin A (Vector Lab, U.S.A.) at a concentration of 10 μg/ml, followed by shaking for 1 hour. Then, the membrane was washed with TNT buffer [25 mM Tris-HCl buffer (pH 7.5) containing 0.5M NaCl and 0.1% Triton X-100] for 10 minutes, for three (3) times. Further, the membrane was immersed for 45 minutes in phosphate buffer-NaCl solution containing a complex of avidin and biotinylated horse radish peroxidase [Standard Vactostain (registered trade mark) ABC kit, Vector Lab], and was washed with TNT buffer (10 minutes, 3 times).

Figure 17:
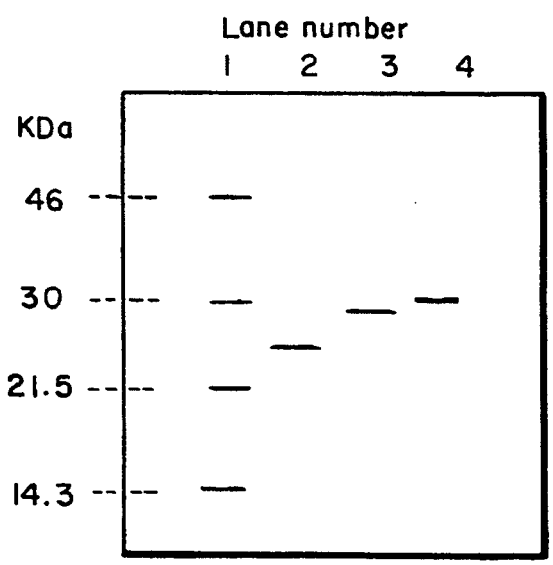
FIG. 17 is a diagram showing stained GAF (derived from NMC-G1) using biotinyl concanavalin A, avidin and biotinyl peroxidase.

A mixture of 20 ml of TN buffer [25 mM Tris-HCl buffer (pH 7.5) containing 0.5M NaCl] and 13.2 μl of aqueous hydrogen peroxide was added to a solution of 12 mg of 4-chloro-1-naphthol in 4 ml of methanol, and the membrane was immersed therein to develop color. Results thereof are shown in FIG. 17. FIG. 17 is a diagram showing stained GAF using biotinyl concanavalin A, avidin and biotinyl peroxidase.

Three molecular species of GAF were all stained and it indicates that these molecules can bind to concanavalin A by their carbohydrate chains.

Figure 18:
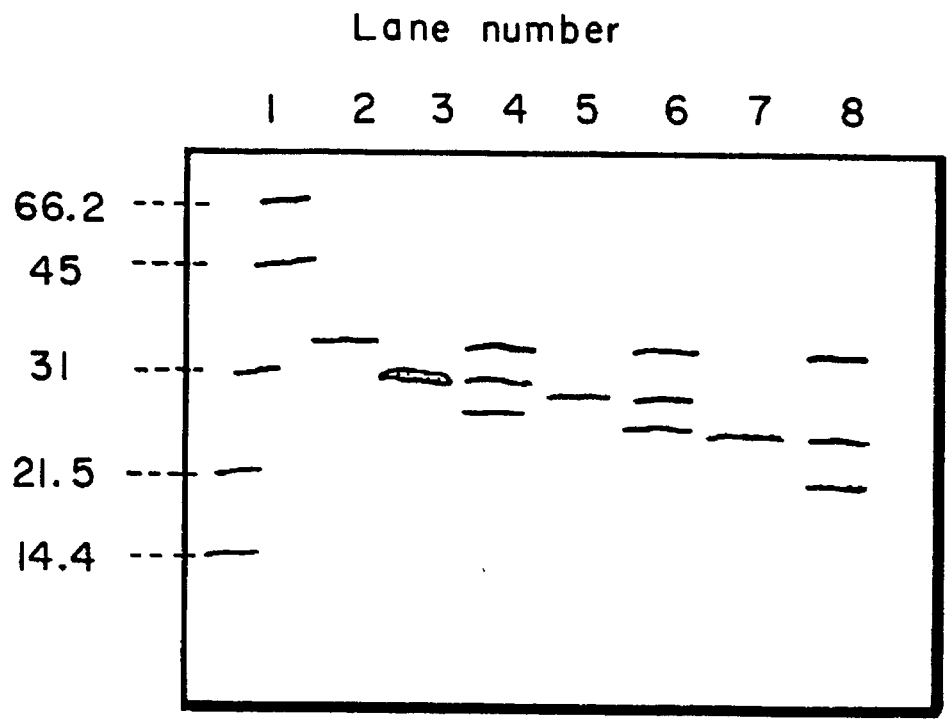
FIG. 18 is a diagram showing results of N-glycanase treatment of GAF (derived from NMC-G1)

Enzymatic deglycosylation using N-glycanase was carried out according to the protocol of Genzyme (Boston, U.S.A.). After N-glycanase treatment of GAF, SDS-polyacrylamide gel electrophoresis was performed, and the gel was silver-stained. Results thereof are shown in FIG. 18. The band of each of 25 kDa, 29 kDa and 30 kDa GAFs was decreased in molecular weight by 3 to 4 kDa after the treatment although it appeared that the deglycosylation was only partially completed. This showed the GAF had 3 to 4 kDa sugar chain of N-glycosylated type.

From the above two experiments, it was confirmed that each of the 25 kDa, 29 kDa and 30 kDa GAFs has an N-linked carbohydrate glycosido type sugar chain attached to its glycosylation site.

Example 4

Analysis of N-Terminal Amino Acid Sequence

Three kinds of GAFs (25 kDa, 29 kDa and 30 kDa) were adsorbed in ProBlott (registered trade mark) (Applied Biosystems, California, U.S.A.), a polyvinylidene difluoride type membrane, and their amino acid sequences were analyzed using a protein sequencer (Model 473A system, Applied Biosystems). About 60 pmol of 25 kDa GAF, about 5 pmol of 29 kDa GAF and about 55 pmol of 30 kDa GAF were so analyzed. The resulting sequences are shown below:

```
                 1             5                    10
25 kDa Ala—Asp—Z₁—Leu—Gly—Gln—Ser—Glu—Ala—Gly—Gly—Leu—Pro—
           15  16              20    21
           X—Gly—Pro—Ala—Val—Thr—Asp—Leu— (SEQ ID NO:16)

1          5    6   7          10
29 kDa X—Gln—Asp—Ala—Val—Pro—Phe—Gly—Asn—Val—Pro—(Ser)—
       13
       Leu— (SEQ ID NO:17)

1             5                    10
30 kDa Z₂—Gly—Glu—Val—Gly—Asn—Tyr—Phe—Gly—Val—Gln—Asp—Ala—
          15  16              20    23
          Val—Pro—Phe—Gly—Asn—Val—(Pro)—X—Leu—Leu— (SEQ ID NO:18)
```

$Z_1$=His or Pro
$Z_2$=Leu or Ala
X=Unidentified amino acid
( ): Amino acid undetermined, but deduced

Example 5

Cloning of GAF cDNA and Analysis of Nucleotide Sequence Thereof

Based on the amino acid sequence of 30 kDa GAF obtained in Example 4, the following two oligonucleotide primers (primers 1 and 2) which corresponded to this sequence and to which a recognition sequence of a restriction enzyme was added were synthesized.

```
                  1            5                10
30 kDa GAF Z₂ Gly Glu Val Gly Asn Tyr Phe Gly Val—
```

Primer 1: 5'-AAGGATCCGTIGGIAAYTAYTTYGG-3' (SEQ ID NO:19)

```
           11         15             20      23
Gln Asp Ala Val Pro Phe Gly Asn Val (Pro) X Leu Leu
```

Primer 2: 5'-AAGAATTCACRTTICCRAAIGGIAC-3' (SEQ ID NO:20)

Z₂=Leu or Ala, I=Inosine, Y=T/C, R=A/G

Using these primers, the polymerase chain reaction (PCR) [K. B. Mullis and F. A. Fuloora, *Methods in Enzymology*, 155, 335 (1987)] was conducted by use of human genome-derived DNA as a template (GeneAmp (registered trade mark) DNA Amplification Reagent Kit (Ceatas, U.S.A.)). Each of primers 1 and 2 was added in an amount of 560 ng per μg of genome DNA, and 2.5 units of Ampli Taq (registered trade mark) (Ceatas, U.S.A.) was added to 100 μl of the reaction solution. Then, a cycle of DNA synthesis at 94° C. for 1 minute, at 50° C. for 2 minutes and at 72° C. for 3 minutes was repeated 25 times. This reaction product was subjected to acrylamide gel electrophoresis, and fragments having a desired length of about 63 bp were recovered. As a result of the analysis of the nucleotide sequence thereof, the following sequence was obtained:

5'-GGATCCGTGGGGAACTATTTCGGGGTGCAGGATGCGGTCCCCTTCGGCAA
CGTGAATCC-3' (SEQ ID NO:21)

Based on this sequence, the following two probes (probes 1 and 2) were chemically synthesized.

Probe 1 5'-TGGGGAACTATTTCGGGGTGCAGGATGCGG-3' (SEQ ID NO:22)
Probe 2 5'-ACGTTGCCGAAGGGGACCGCATCCTGCACC-3' (SEQ ID NO:23)

Separately, a cDNA library using *E. coli* x1776 as a host was prepared by introducing cDNA synthesized from mRNA of human foreskin-derived primary culture cells into the pCD vector [see Okayama et al., *Molecular Cell Biology*, 3, 280 (1983)] which was supplied from Dr. Okayama, National Institute of Child Health and Human Development, Bethesda, U.S.A. Plasmid DNA was extracted from this cDNA library by the alkali method [H. C. Birnboim and J. Doly, *Nucleic Acids Research*, 1, 1513 (1979)], and *E. coli* DH1 was infected with this DNA to prepare a cDNA library containing about 2×10⁵ clones of *E. coli* DH1 as host cells.

Ten nitrocellulose filters (HATF filter, Millipore) were plated with the above-mentioned cDNA library using *E. coli* DH1 to about 1×10⁵ clones/filter. Ten pairs of replica filters consisting of 2 filters were prepared from the above 10 master filters. Plasmid DNA exposed for denaturation by lysing *E. coli* on the replica filters with 0.5N NaOH solution was fixed on the filters [M. Crunstein and D. S. Hogness, *Proc. Natl. Acad. Sci. U.S.A.*, 72, 8961 (1975)].

³²P was introduced into the 5'-terminus of probes 1 and 2 by using T4 polynucleotide kinase and [γ-³²P]-ATP. Each of these probes was hybridized with each of the replica filters on which the DNA was fixed. The hybridization reaction was carried out at 55° C. for 16 hours in 10 ml of a solution of 5 X SSPE (180 mM NaCl; 10 mM NaH₂PO₄, 1 mM EDTA, pH 7.4) supplemented with 10 μCi probe, 5 X Denhardt's, 0.1% SDS and 100 μg/ml of denatured salmon sperm DNA. After completion of the reaction, the filters were washed 3 times with a solution of 5 X SSC (0.15M NaCl, 0.015M sodium citrate) and 0.1% SDS at room temperature, and twice further at 60° C. for 30 minutes [T. Maniatis et al. *Molecular Cloning*, p.309, Cold Spring Harbor Laboratory (1982)].

Radioautograms were taken from the washed filters and the radioautograms of the replica filters in sets of two filters were superposed on each other to search the cells reactive to both the two kinds of probes. By this method, 2 clones reactive to the two kinds of probes were obtained from 1×10⁶ clones.

The plasmid DNAs of the two clones were extracted and purified by the alkali method (described above). When the cDNA portions of the plasmid DNAs were cut out with restriction enzyme BamHI and fractionated by agarose gel electrophoresis, both the cDNAs derived from the two clones showed the same chain length of about 1.55 kb. These two strains were considered to be identical with each other.

The nucleotide sequence of the cDNA portion of the plasmid contained in one (*E. coli* K12 DH1/pGAF1) of these two strains contained was determined by the dideoxynucleotide synthetic chain termination method [J. Messing et al., *Nucleic Acids Research*, 9, 309 (1981)]. The nucleotide sequence (SEQ ID NO: 24) thus determined and the amino acid sequence (SEQ ID NO: 25) deduced from this nucleotide sequence are shown in FIG. 19. The cDNA portion contained in the sequence determined *E. coli* K12DH1/pGAF1 ("pGAF1") had a chain length of 1493 b, and contained a 5'-terminal non-translated region, an all amino acid coding region, a 3'-terminal non-translated region and a poly A chain. The coded amino acid sequence had 208 amino acids, and contained all the partial amino acid sequences of 30 kDa, 29 kDa and 25 kDa disclosed by the N-terminal sequence analysis as discussed in Example 4. The coded amino acid sequence was partially different from the sequences obtained in Example 4 (the 1-position of 25 kDa, Ala; the 12-position of 29 kDa, Ser; and the 23-position of 30 kDa, Leu). However, these differences were observed in the N-terminus and portions identified exceeding 10 residues, all of which were liable to give uncertain results in amino acid analysis. Therefore, the sequence deduced from the cDNA is considered to be correct.

Example 6 Expression of Genes Coding for GAF in Mammalian Cells (1) Expression of GAF in COS-7 Cells Monkey Cos-7 cells in IMDM medium supplemented with 10% NU-Serum (Colaborative Research) were plated in Falcon plastic dishes having a diameter of 60 mm at 6×10⁵ cells/dish. The next day, after washing with serum-free IMDM medium, reaction solutions containing 2 μg and 10 μg of plasmid pGAF-1 DNA and 400 μg/ml of DEAE-dextran were prepared according to the method known in the art [B. Seed et al., *Proc. Natl. Acad. Sci. U.S.A.*, 52, 3365 (1987)], and one or the other of the above solutions was added to every dish. After incubation at 37° C. for 4 hours, DMSO treatment was carried out. Then, cell culturing was continued in a medium (3 ml/dish) containing 10% Nu-Serum, and the medium was collected after 70 to 72 hours. The cells were recovered from the dish by rabber policeman and suspended in 1.5 ml of phosphate buffered saline.

Figure 20:
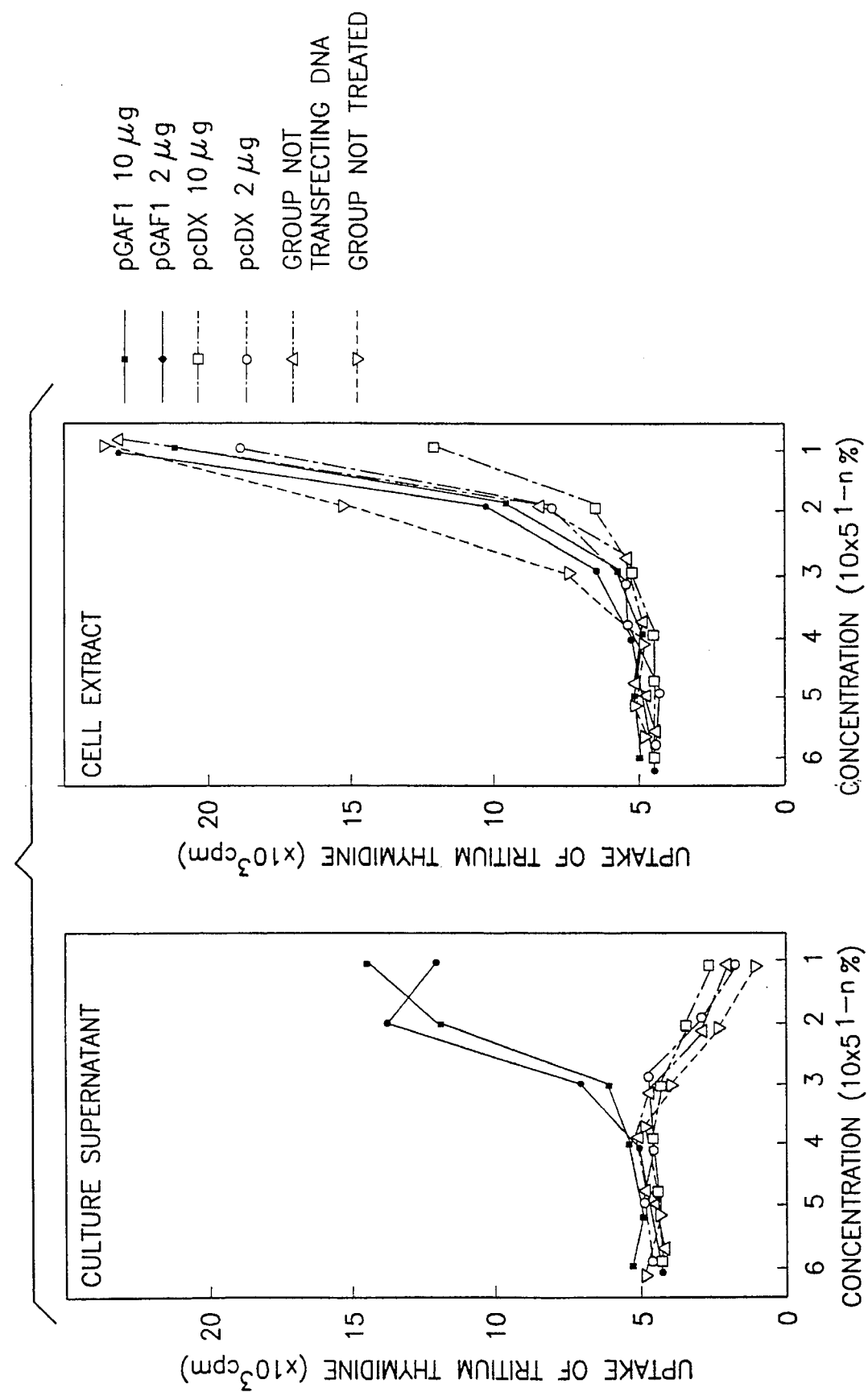
FIG. 20 is graphs showing results obtained by expressing pGAF1 in COS-7 cells and assaying growth promoting activity thereof upon the glial cells.

Glial cell growth promoting activity was detected in a culture supernatant of the COS-7 cells transfected with pGAF1. The activity was not detected in culture supernatants of the COS-7 cells which were transfected with plasmid pCDX having no GAF cDNA nore of the COS-7 cells which were not transfected as shown in FIG. 20. Also according to FIG. 20, extracts from pGAF1 transfected cells obtained by two cycles of freeze-thawing and sonication did not show significant activity, compared to that from the control transfectant. From these results, it was confirmed that the cDNA of pGAF1 was correctly coded for GAF protein, and it was revealed that, when the cDNA was expressed with the COS cells, the product was secreted into the culture solution.

(2) Expression of GAF in CHO Cells (a) Construction of Expression Plasmid pDGAF1

Figure 21:
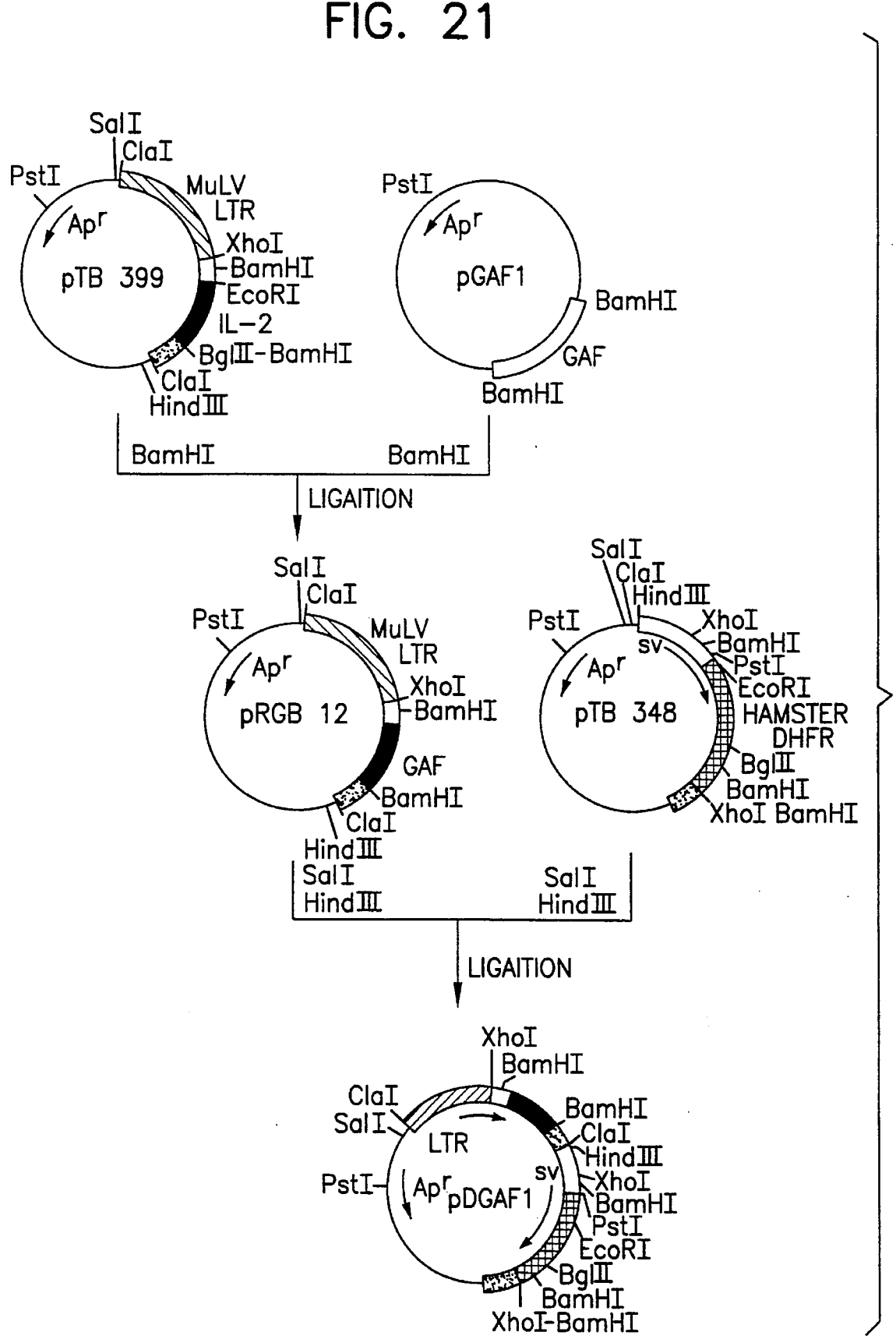
FIG. 21 is a schematic representation showing the construction of plasmid pDGAF1.

Plasmid pGAF1 obtained in Example 5 was cleaved with restriction enzyme BamHI, and a 1.55-kb GAF cDNA fragment was isolated. Similarly, vector pTB399 for mammalian cells [*Cell Struct. Funct.*, 12, 205 (1987)] was cleaved with restriction enzyme BamHI, and the IL-2 cDNA region was removed, followed by insertion of the above-mentioned 1.55-kb fragment of the GAF cDNA to construct expression plasmid pRGB12 which could express GAF cDNA in mammalian cells under the control of Abelson murine leukemia virus (MuLV) LTR. Further, this plasmid was cleaved with restriction enzyme SalI-HindIII, and an expression unit portion (promoter gene-poly(A) signal) was inserted into the SalI-HindIII site located upstream from the SV40 promoter of hamster dihydrofolate reductase (DHFR) expression plasmid pTB348 [*Cell Struct. Funct.*, 12, 205 (1987)] to construct plasmid pDGAF1. FIG. 21 is a schematic representation showing the construction of plasmid pDGAF1.

(b) Expression in CHO Cells

Figure 22:
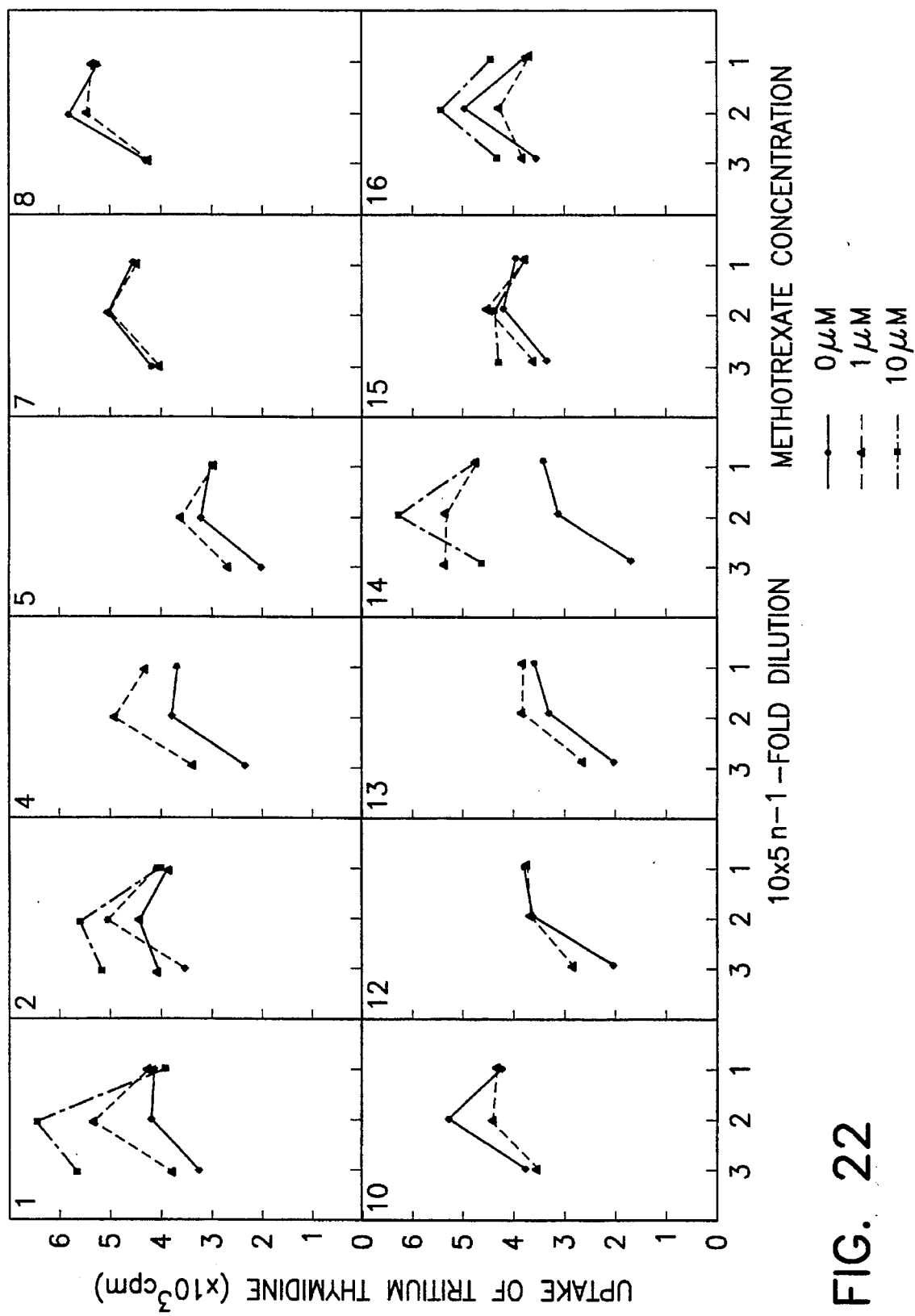
FIG. 22 is graphs showing GAF activity contained in a culture supernatant of methotrexate-resistant CHO cells.

CHO dhfr⁻ cells were plated in a dish of diameter of 6 cm with HamF12 medium supplemented with 10% fetal calf serum. The next day, the medium was replaced with the same fresh medium. After 2 hours, 10 μg of plasmid pDGAF1 DNA was transfected by the calcium phosphate method [Graham et al., *Virology*, 52, 456 (1973)]. After being cultured in a growth medium for 2 days, the cells were plated again in a 96-well microtiter plate (Nunc) with DMEM medium supplemented with 35 μg ml proline and 10% dialysis FCS. The medium change was carried out every 3 to 4 days, and some dhfr⁺ transformants were selected. These transformants were transferred to a 24-well microtiter plate (Linbro, Flow) in DMEM medium supplemented with 35 μg/ml proline and 5% FCS to culture each clone. Thereafter, DMEM medium supplemented with 35 μg/ml proline and 5% FCS was used for culture. 16 of these clones which produced GAF protein were transferred to a 6 cm diameter dish, and were cultured with an increasing concentration of the methotrexate (MTX) by three steps (0.1, 1 and 10 μM) to get 10 μM MTX resistant clones which might have amplified DHFR and GAF gene. The GAF activity in the culture supernatant of each clone is shown in FIG. 22. The values of abscissa in the Figure indicate the dilution rate of the added supernatant. Clones having high GAF activity were selected, and used for natural-type GAF producing cells to which sugar chains were attached.

Example 7

Transformation of Mouse BALB/3T3 Cells by Introduction of GAF Genes (1) Construction of GAF Expression Plasmid pRGB12

Plasmid pRGB12 described in Example 6 was used as a GAF expression plasmid. Plasmid pTB1055 into which the GAF cDNA was not inserted was used as a control plasmid.

(2) Transformation of BALB/c 3T3 Cells

About $10^5$ cells of mouse BALB/3T3 clone A31 [subclone A31-1-1 (Kakunaga et al., *Science*, 209, 505 (1980)), supplied from Dr. Kakunaga] were plated in a 6 cm dish in DMEM medium supplemented with 10% bovine serum. The next day, the medium was replaced with a new volume of the same medium. After 3 hours, 1, 2, 5 or 10 μg of plasmid pRGB12 or pTB1055 were tranfected by the calcium phosphate method [Graham et al., *Virology*, 52, 456 (1973)]. After incubation at 37° C. for 4 hours, stimulation of transfection was carried out with a PBS solution supplemented with 15% glycerol. Cell culturing was continued for 4 weeks, replacing half of the medium for DMEM medium containing 5% calf serum for every 3 to 4 days. After termination of the culture, the medium was discarded and ice-cooled methanol was added thereto to fix the cells for 15 minutes. After washing with water, the cells were stained with the Giemza solution for 20 minutes. The dishes were washed with water and dried in air, followed by the counting of stained foci. Results thereof are shown in Table 2. These results clearly revealed that the GAF genes had a transforming property.

TABLE 2

Focus Formation of A31 Cells by Introduction of GAF Genes

| Plasmid | Amount of transfected DNA (μg) | | | | |
|---|---|---|---|---|---|
| | 0 | 1 | 2 | 5 | 10 |
| pTB1055 | 0* | N.T. | 0 | N.T. | 0 |
| pRGB12 | 0 | 3 | 28 | 25 | 33 |

*The number of focuses per dish
N.T.: Not tried

Example 8

(1) Expression of GAF in *E. coli*

(a) Construction of GAF Expression Plasmid pETGAF1

Figure 23:
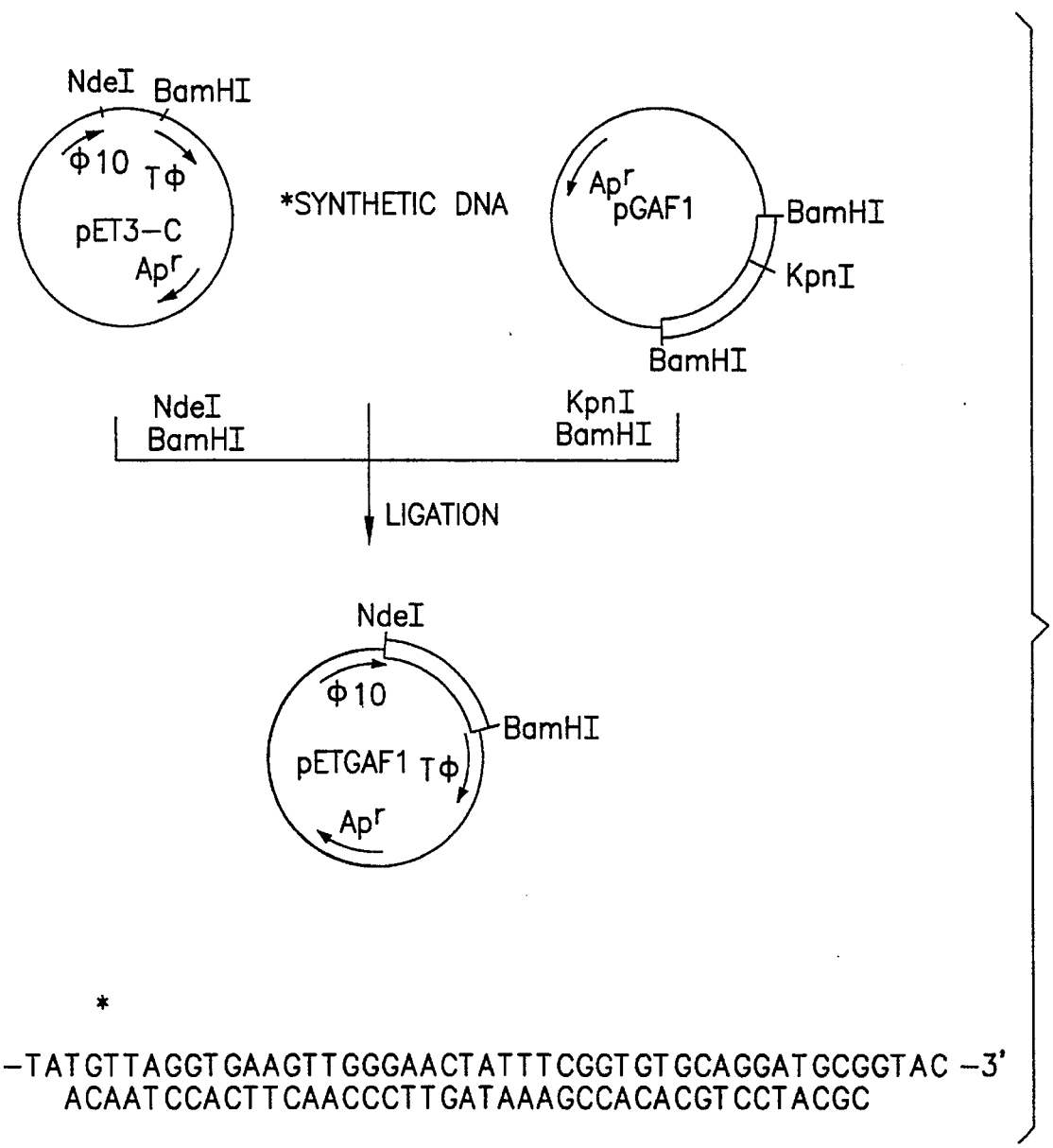
FIG. 23 is a schematic representation showing the construction of plasmid pETGAF1.

Plasmid pGAF1 containing all the structure genes of GAF obtained in Example 5 was cleaved with restriction for enzyme KpnI-BamHI, and a 1.25-kb DNA fragment was isolated. Similarly, plasmid pET3-c containing a T7 promoter was cleaved with restriction enzyme NdeI-BamHI, and a 4.6 kb DNA was isolated, followed by insertion therein of the above-mentioned 1.25-kb fragment of the GAF cDNA and synthesized DNA fragments (NdeI-KpnI) [(SEQ ID NO:26) and (SEQ ID NO:27)] which code Met just ahead of Leu, the N-terminus of the purified 30 kda GAF protein. In this manner, expression plasmid pETGAF1, which could express the GAF cDNA under the control of the T7-promoter, was constructed. FIG. 23 is a schematic representation showing the construction of plasmid pETGAF1. Using this plasmid, *E. coli* MM294 (DE3)/pLysS was transformed to produce GAF expression plasmid *E. coli* MM294(DE3)/pLysS,pETGAF1.

Figure 24:
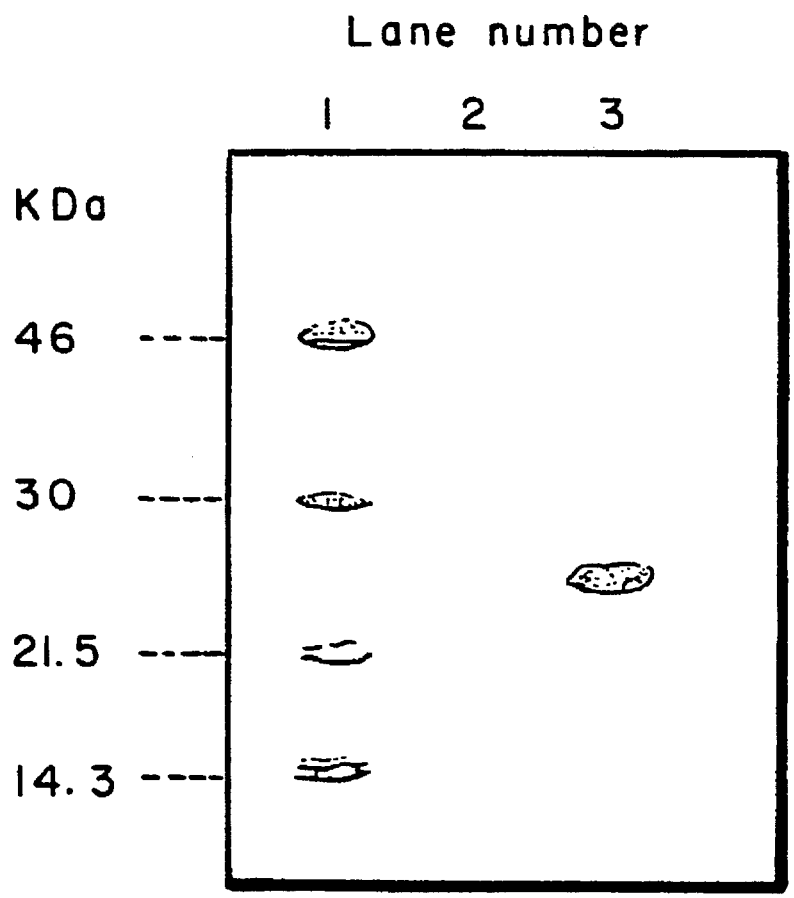
FIG. 24 is a diagram showing rhGAF contained in an extract of MM294(DE3)/pLysS,pETGAF1 which is stained by Western Blotting method.

MM294(DE3)/pLysS,pETGAF1 thus obtained was cultivated in LB medium, and expression of GAF was induced by isopropyl-β-D(−)-thiogalactoside(Wako Pure Chemical industries, Ltd., Japan). Then, extracted proteins from the cells corresponding to 200 μl of the culture solution were examined by Western Blotting method using rabbit anti-GAF polyclonal anti-serum (500-fold dilution) recognizing the N-terminal portion of GAF protein. As a result, a specific band was observed as shown in FIG. 24. The transformant MM294(DE3)/pLysS, pET3-c which was transformed with plasmid pET3-c having no GAF cDNA did not produce the band.

(2) Extraction of Human GAF (rhGAF) Produced in *E. coli*

*E. coli* MM294(DE3)/pLysS, pETGAF1 was cultivated with shaking at 37° C. in LB medium supplemented with 50 μg/ml ampicillin and 10 μg/ml chloramphenicol. When the Klett value of the culture solution reached 120, isopropyl-β-D(-thiogalactoside was added to a final concentration of 0.4 mM, and the culture was further cultivated with shaking at 37° C. for 3.5 hours. The cells collected from 1 liter of the culture solution by centrifugation (6,000 rpm, for 10 minutes) were suspended on ice in 80 ml of 20 mM Tris-HCl buffer supplemented with 2 mM (p-amidinophenyl) methanesulfonyl fluoride hydrofluoride (Wako Pure Chemical Industries, Japan), 100 μg/ml egg white lysozyme (Seikagaku Kogyo K. K., Tokyo, Japan) and 0.1M NaCl, and the resulting suspension was allowed to stand at 4° C. for 1 hour, followed by incubation at 37° C. for 3 minutes. The suspension thus obtained was cooled with ice and subjected to ultrasonic treatment [Sonifier Cell Disruptor of 800 (registered trade mark), Branson, U.S.A., at an output of 8 for 2 minutes]. An *E. coli* extract was obtained by centrifugation at 17,000 rpm for 40 minutes.

(3) Purification of Human GAF (rhGAF) Produced in *E. coli*

Step 1: Ammonium sulfate precipitation

To 80 ml of the *E. coli* extract obtained from 1 liter of the above solution, 27 ml of saturated ammonium sulfate solution was added, followed by mixing. Then, the mixture was allowed to stand at 4° C. for overnight. Subsequently, the mixture was centrifuged at 17,000 rpm for 40 minutes to obtain a supernatant.

Figure 25:
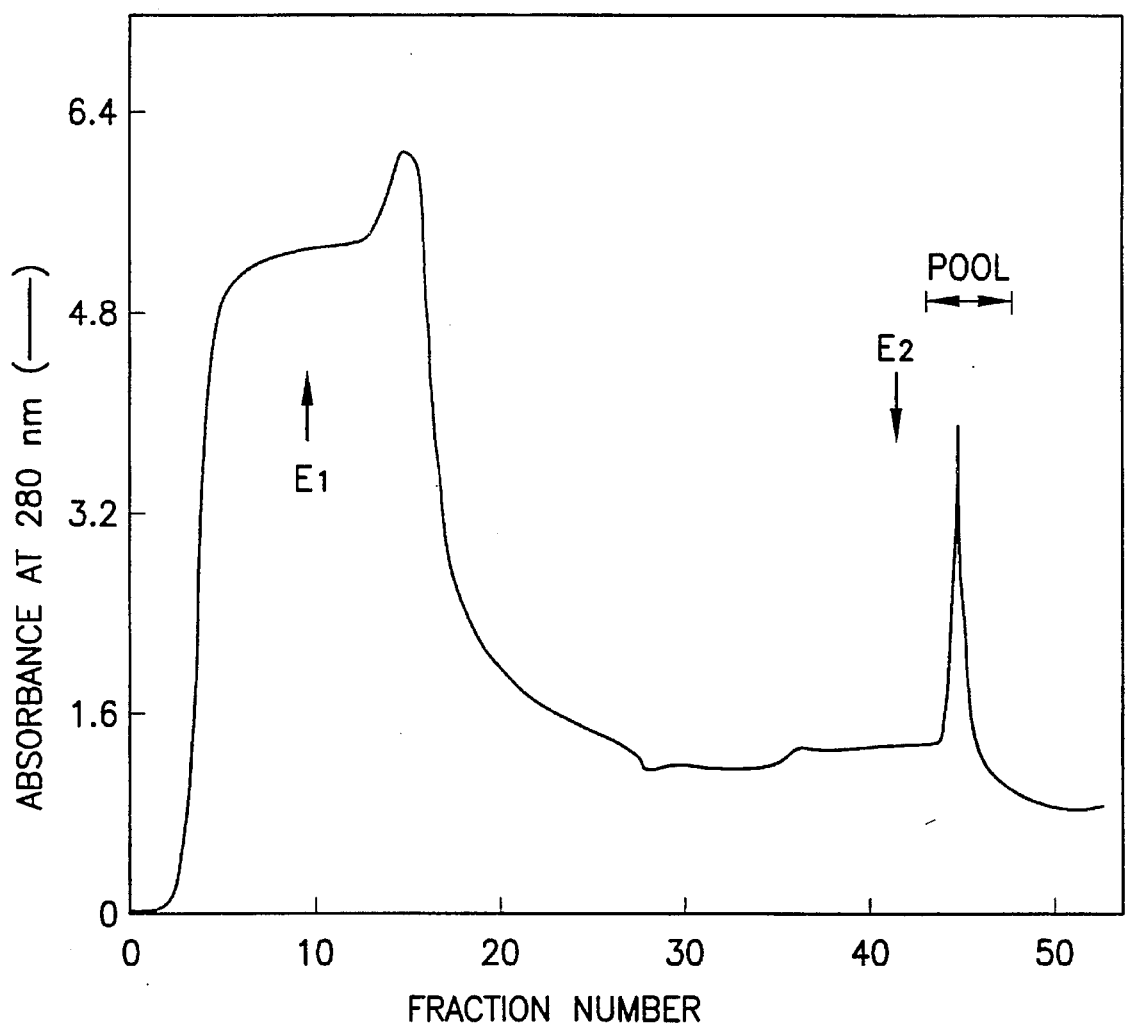
FIG. 25 shows a protein elution pattern on hydrophobic column (Example 7-(3), step 2)

Step 2: Hydrophobic column chromatography 100 ml of the centrifuged supernatant obtained in step 1 was passed through a Butyl-Toyopearl column 650M (bed volume: 50 ml, 2.5 cm in internal diameter×10 cm in length, Tosoh Corp. Tokyo, Japan) equilibrated with 20 mM Tris-HCl buffer (pH 7.6) supplemented with 25% saturated ammonium sulfate solution, at a flow rate of 80 ml/hour at 4° C. The resin was thoroughly washed with 20 mM Tris-HCl buffer (pH 7.6) supplemented with 12.5% saturated ammonium sulfate solution and 2 mM aPMSF, and then, rhGAF protein-containing fractions (assayed by Western-blotting technique, data not shown) were obtained by elution with 20 mM Tris-HCl buffer (pH 7.6) supplemented with 15% glycerin, 0.1% CHAPS and 2 mM aPMSF ($E_2$, 80 ml/hour, 10 ml/fraction, 4° C.), the results of which are shown in FIG. 25.

Step 3: Heparin affinity high performance liquid column chromatography

Figure 26:
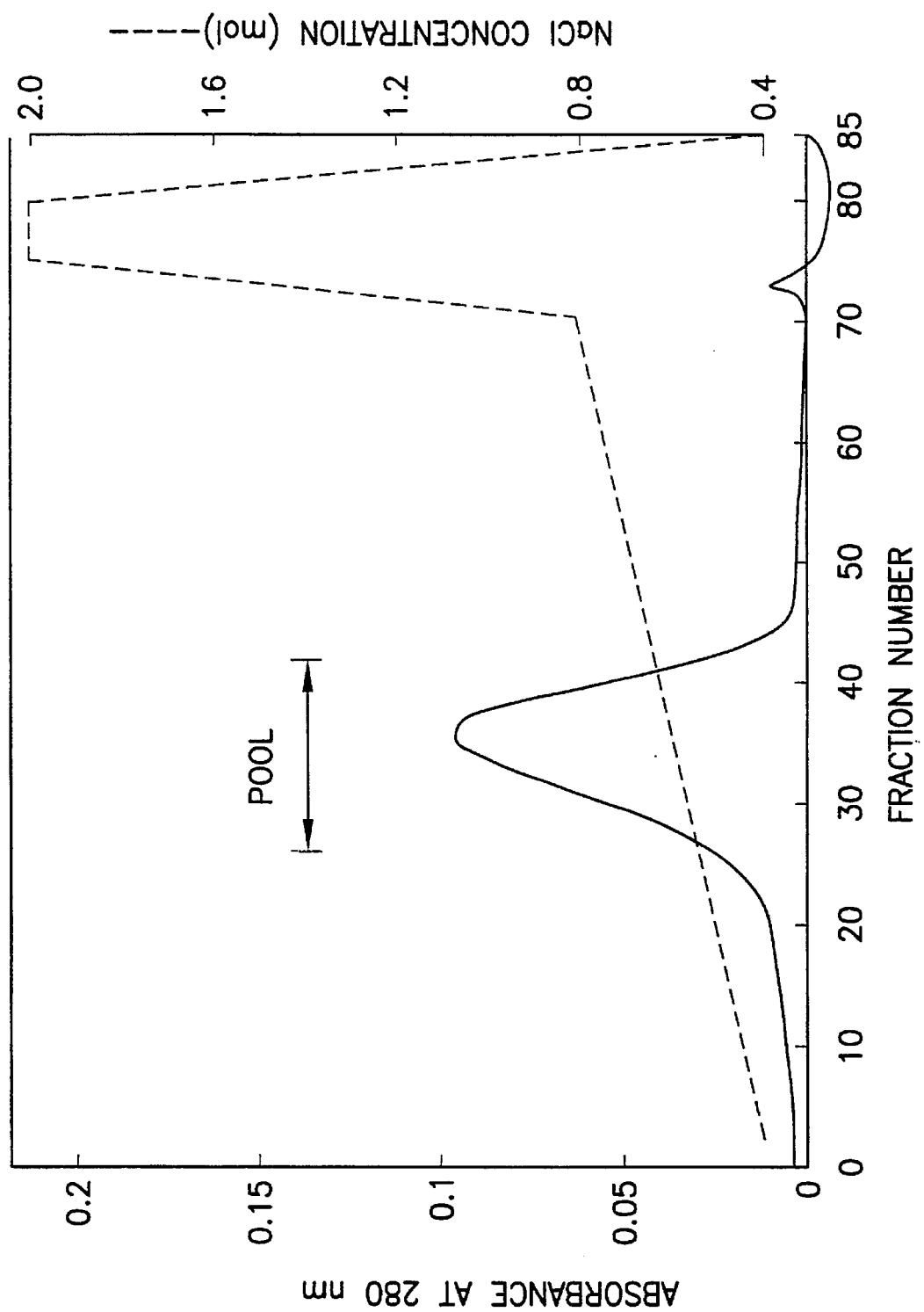
FIG. 26 shows a protein elution pattern on heparin affinity high performance liquid chromatography (Example 8-(3), step 3)

The rhGAF protein-containing fractions (fractions 44 to 47) obtained in step 2 were pooled (40 ml). Of 40 ml of this solution, 36 ml was applied to high performance liquid column chromatography (Gilson Medical Electronics, France) equipped with an HR-894 column (8 mm in diameter×50 mm in length, Showa Denko K. K., Japan). The protein adsorbed by the resin was eluted at a flow rate of 2 ml/minute by linearly increasing the concentration of NaCl and fractionated (2 ml/fraction). Buffer A used was 10 mM Tris-HCl buffer (pH 7.6) containing 0.4M NaCl, 0.1% CHAPS and 15% glycerin, and buffer B was 10 mM Tris-HCl buffer (pH 7.6) containing 2M NaCl, 0.1% CHAPS and 15% glycerin. The program of elution was as follows:

0 minute (100% A) - 70 minutes (75% A+25% B) - 75 minutes (100% B) - 80 minutes (100% B) - 85 minutes (100% A). The results of this elution are shown in FIG. 26. The column temperature was room temperature.

Figure 27:
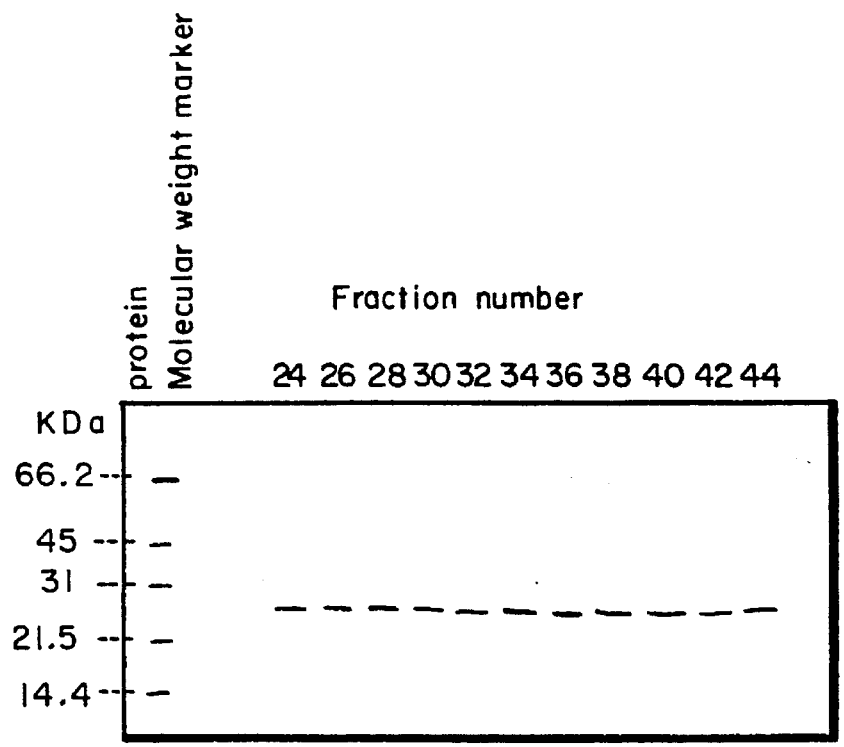
FIG. 27 shows an SDS polyacrylamide gel electrophoresis diagram of a purified rhGAF.
Figure 28:
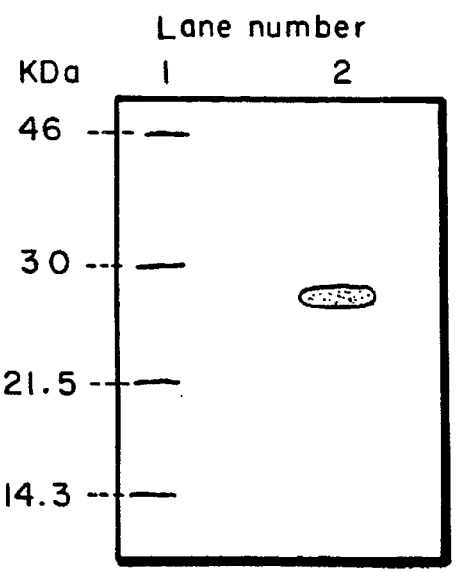
FIG. 28 is a diagram showing the purified rhGAF stained by Western Blotting method.

One microliter of each of eluted fractions 24, 26, 28, 30, 32, 34, 36, 38, 40, 42 and 44 was subjected to SDS-polyacrylamide gel electrophoresis (gel concentration: 2.5%) in the presence of 2-mercaptoethanol, followed by silver staining. Results thereof are shown in FIG. 27. Fractions eluted by increasing the concentration of NaCl gives a single band at 27 kDa. This 27 kDa protein was also recognized by rabbit anti-GAF polyclonal anti-serum which binds to the N-terminal portion of GAF as shown in FIG. 28. Fractions 27 to 42 were pooled.

(4) Summary of Purification

The summary of purification of rhGAF obtained from 1 liter culture of the *E. coli* MM294(DE3)/pLysS, pETGAF1 is shown in Table 3.

TABLE 3

| Sample | Total protein amount (mg) | Total activity (U) | Specific activity (U/mg) | Activity Recovery (%) | Purification |
|---|---|---|---|---|---|
| *E. coli* extract | 672 | $4.16 \times 10^7$ | $6.19 \times 10^4$ | 100 | 1 |
| 25% saturated ammonium sulfate supernatant | 210 | $4.35 \times 10^7$ | $2.07 \times 10^5$ | 105 | 3.3 |
| Butyl Toyopearl | 37.6 | $4.10 \times 10^6$ | $1.09 \times 10^5$ | 10 | 1.8 |
| Heparin HPLC | 4.5 | $3.3 \times 10^6$ | $7.35 \times 10^5$ | 8.0 | 12 |

The biological activity was assayed by the method described in Reference Example 1. Total activity (U) is expressed as the reciprocal of the dilution ratio of the sample having a 50% uptake value of tritium thymidine, wherein a 100% uptake value of tritium thymidine is defined as the uptake of tritium thymidine in a-medium of 10% fetal calf serum. The amount of the protein was determined by a MicroBCA kit (Pierce, U.S.A.) using bovine serum albumin as a standard.

Example 9

Activity of GAF to Various Culture Cells (2)

(1) Growth Promoting Activity to Glial Cells

Figure 29:
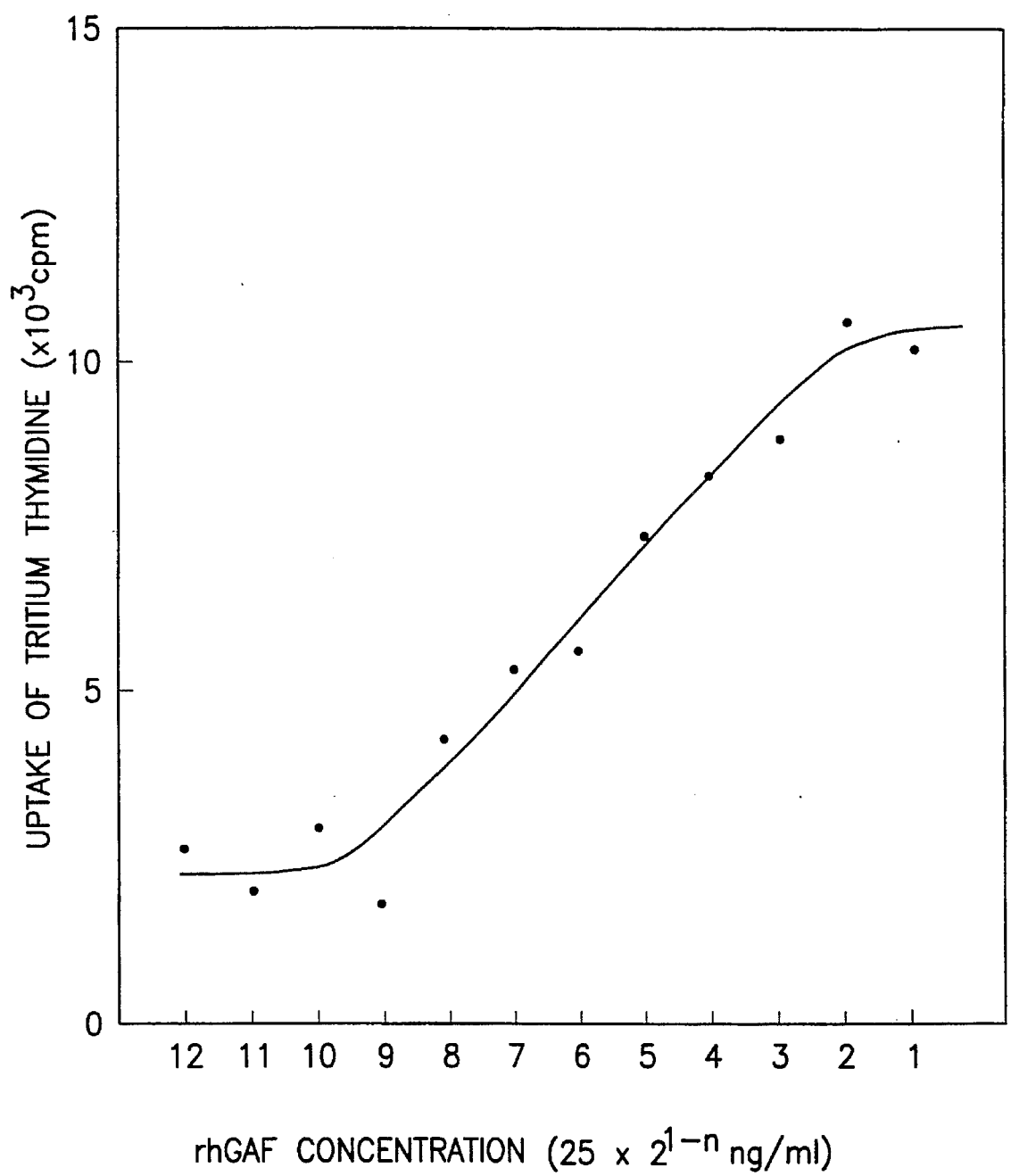
FIG. 29 is a graph showing growth promoting activity of the purified rhGAF upon the glial cells.

As indicated in FIG. 29, the rhGAF obtained by the method described in Example 8-(3) has growth promoting activity to glial cell. In the figure, the values on the abscissa indicate the GAF concentration. GAF's growth promoting activity upon glial cells was assayed according to the method described in Reference Example 1.

(2) Growth Promoting Activity to Fibroblasts

Figure 30:
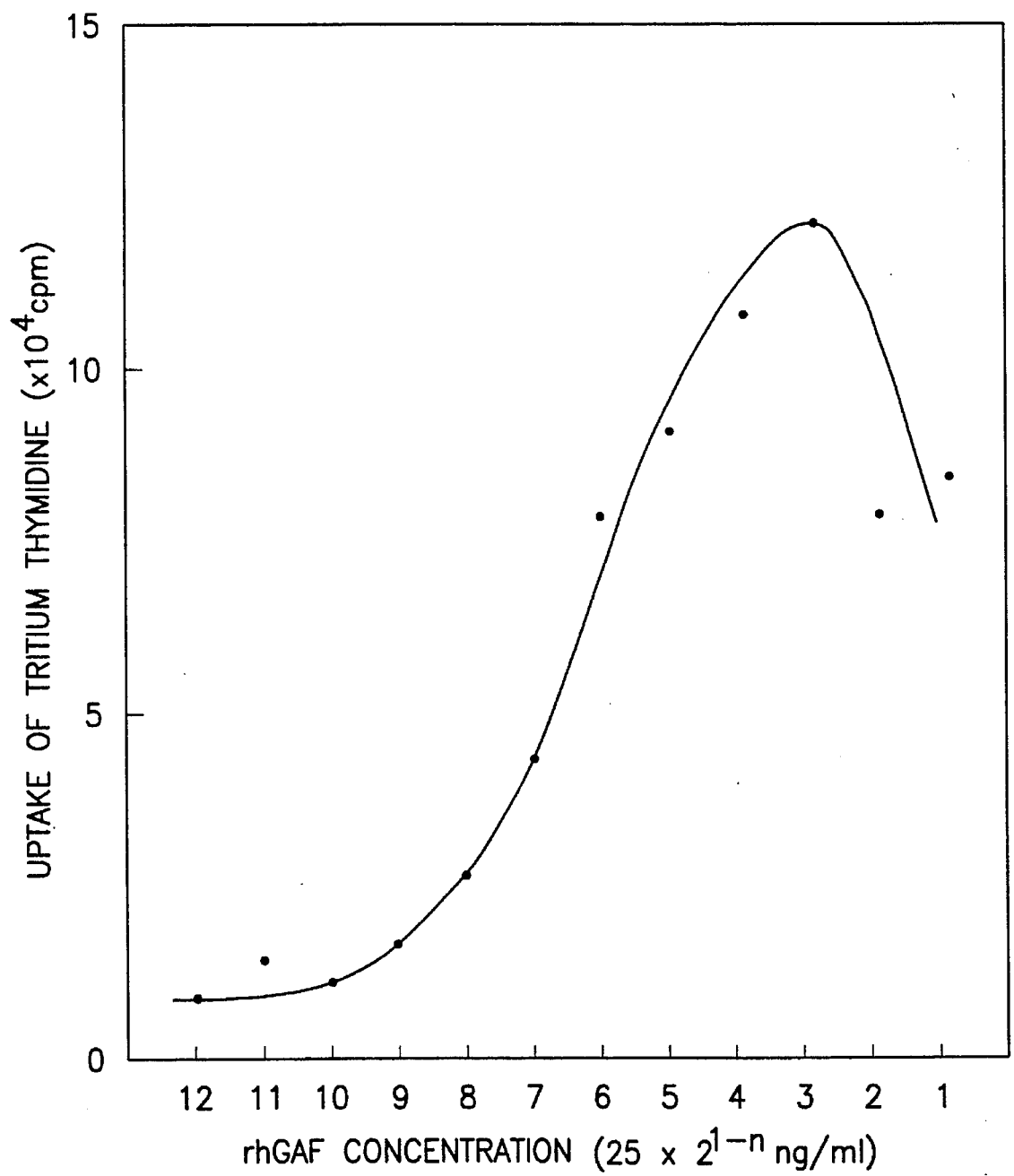
FIG. 30 is a graph showing growth promoting activity of the purified rhGAF upon mouse BALB/3T3 clone A31 cells.

As indicated in FIG. 30, the rhGAF obtained by the method described in Example 8-(3) has growth promoting activity to fibroblast mouse BALB/3T3 clone A31 cells. In the figure, the values on the abscissa indicate the GAF concentration. GAF's growth promoting activity upon A31 cells was assayed according to the method described in Example 2-(4).

(3) Growth Promoting Activity to Rat Vascular Smooth Muscle Cells

Figure 31:
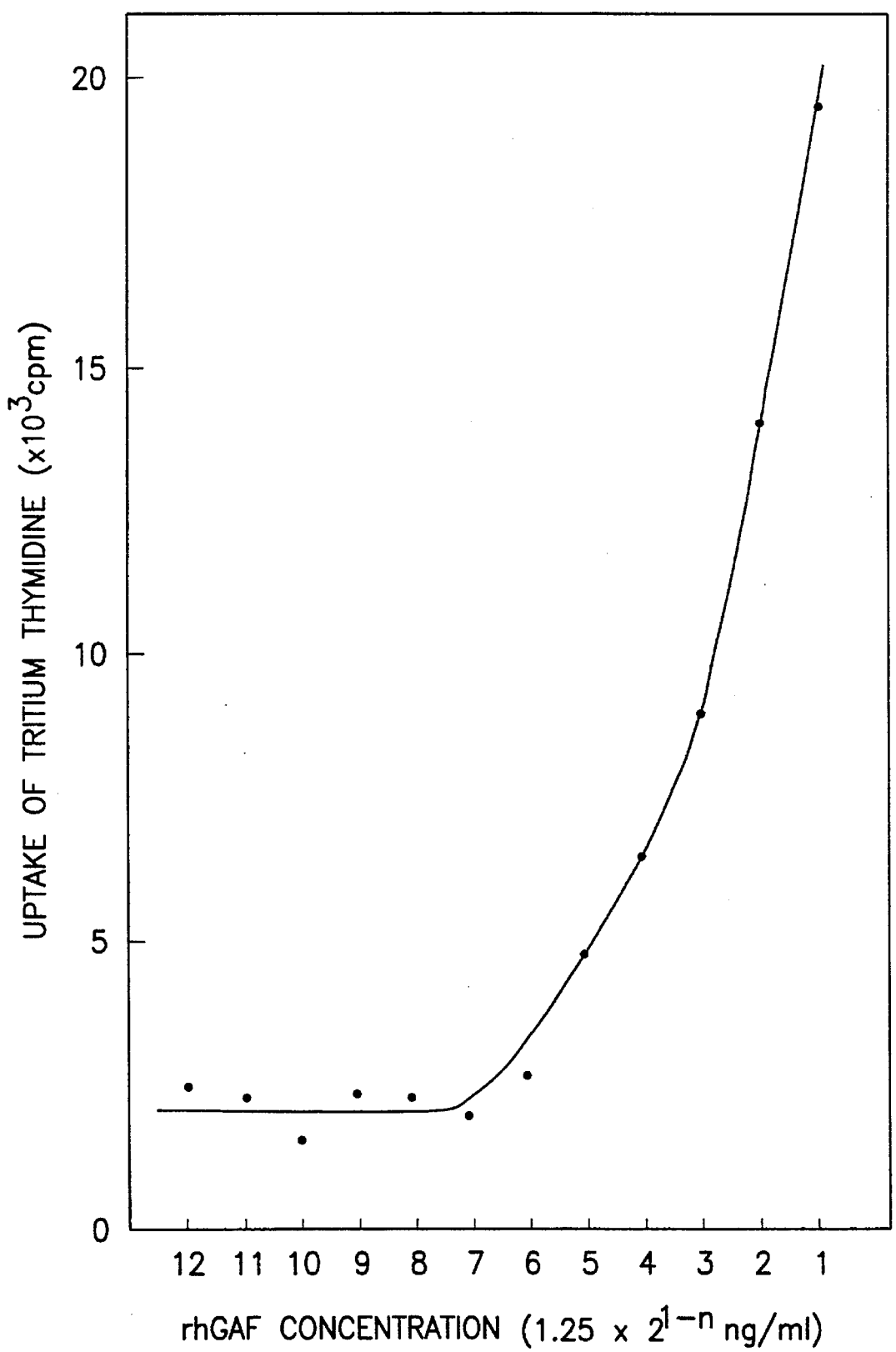
FIG. 31 is a graph showing growth promoting activity of the purified rhGAF upon rat vascular smooth muscle cells.

As indicated in FIG. 31, the rhGAF obtained by the method described in Example 8-(3) has growth promoting activity to rat vascular smooth muscle cells (FIG. 31). In the figure, the values on the abscissa indicate the GAF concentration.

GAF's growth promoting activity upon the rat vascular smooth muscle cells was assayed according to the following method. Rat primary culture vascular smooth muscle cells were plated in each well of a Nunc 96-well microtiter plate (flat-bottomed) in an amount of $3 \times 10^3$/well in 100 μl of Eagle's MEM medium supplemented with 10% calf serum, and cultured. The next day, 80 μl of the medium was discarded from each well, and 180 μl of serum-free Eagle's MEM medium was added to each well. After culturing for 2 days, 20 μl of the medium was discarded from each well. Then, 20 μl of the test sample appropriately diluted with DMEM medium supplemented with 0.1% bovine serum albumin was added to each well, followed by culturing overnight. The next morning, 1 μCi of tritium thymidine (5 Ci/mmol, 1 mCi/ml, RCC Amersham) was added to each well, followed by culturing for further 5 hours. After culturing, the medium was discarded from each well, and 100 μl of PBS containing 0.5% trypsin and 0.01% EDTA was added to each well, followed by standing at room temperature for several minutes. After the detachment of the cells was confirmed under a microscope, the detached cells were collected on a glass fiber filter (Dainippon Pharmaceutical Co., Ltd., Japan) by using a Tiretrek Cell Harvester (Flow Laboratries, Virginia, U.S.A.), and washed with water. Then, the amount of tritium thymidine taken into the cells was measured by a liquid scintillation counter.

(4) Activity to Human Umbilical Vascular Endothelial Cells

Figure 32:
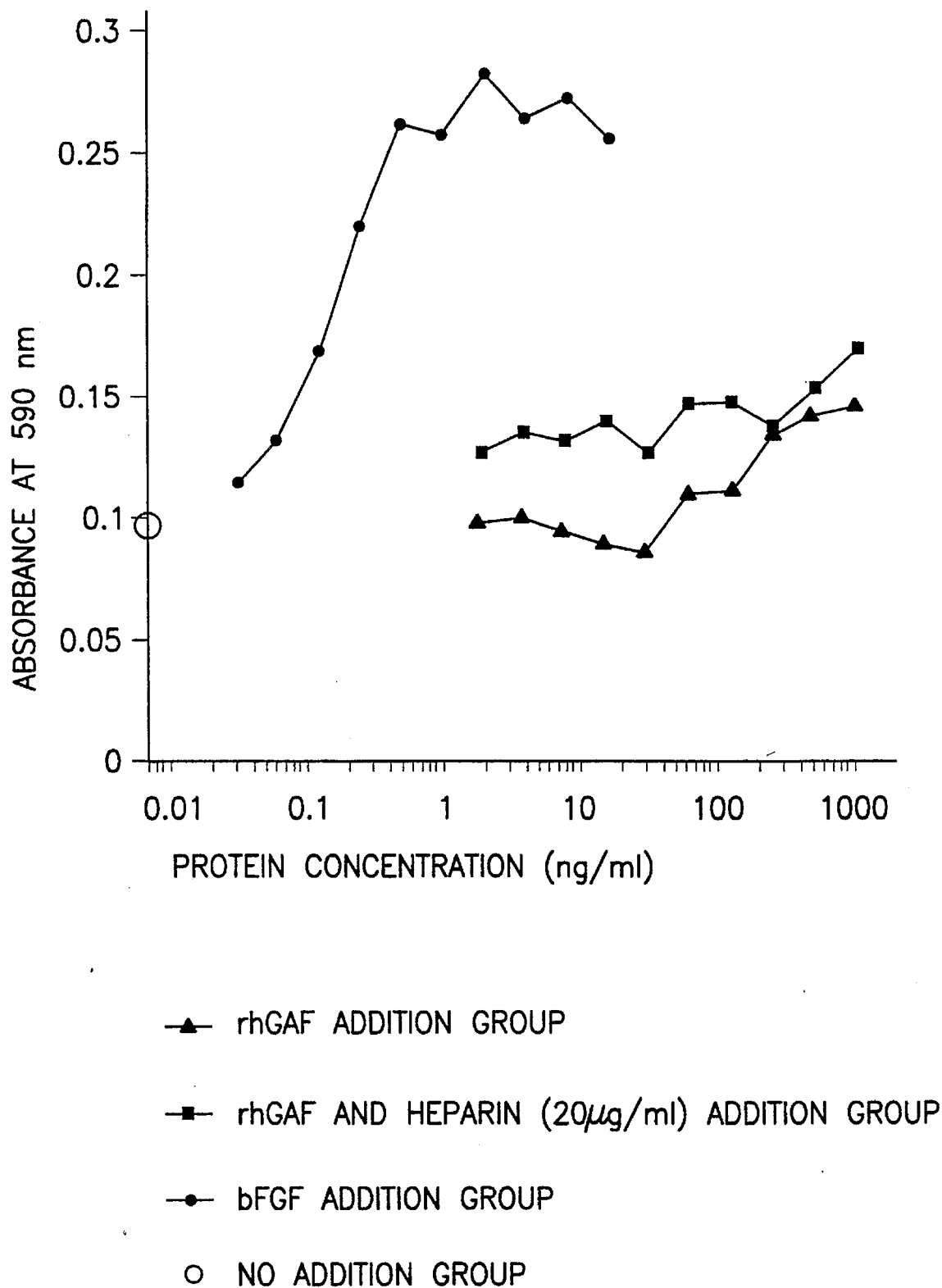
FIG. 32 is a graph showing activity of the purified rhGAF upon the proliferation of human umbilical vascular endothelial cells.

The rhGAF obtained by the method described in Example 8-(3) does not have growth promoting activity to human umbilical vascular endothelial cells, as indicated in FIG. 32, which compares rhGAF and bFGF activity. In the figure, the values on the abscissa indicate the protein concentration of rhGAF or bFGF. The growth promoting activity to the human umbilical vascular endothelial cells was assayed according to the method described in Example 2-(5).

(5) Megakaryocyte Colony Stimulating Factor Activity of rhGAF

Figure 33:
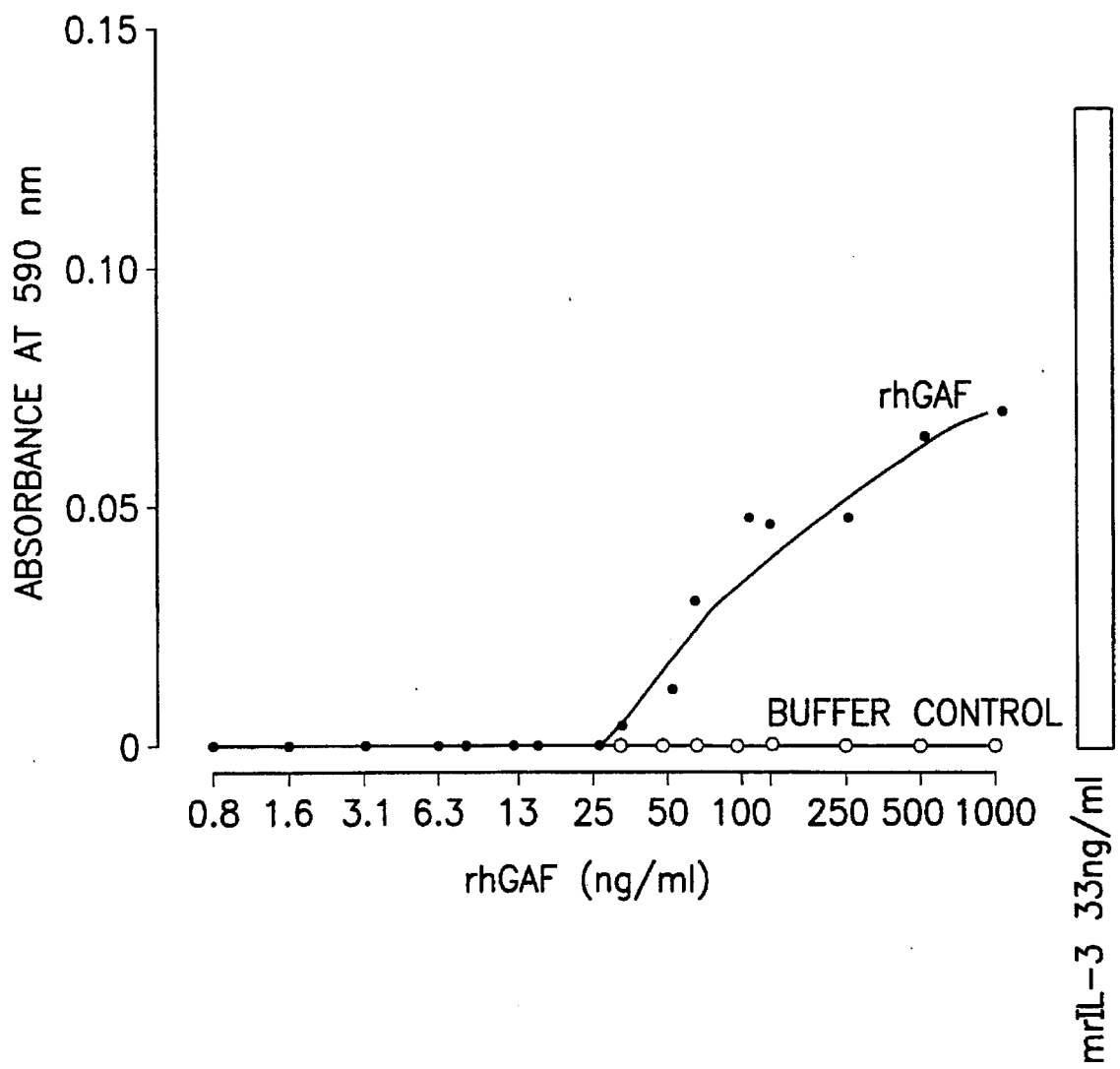
FIG. 33 is a graph showing activity of the purified rhGAF upon the proliferation of mouse bone marrow cells.

BALB/c female mouse bone marrow cells were suspended in Iscove modified Dulbecco's medium (IMDM) supplemented with 20% fetal calf serum(FCS) to give $2 \times 10^7$ cells/ml, and incubated at 37° C. for 1 hour in a plastic culture dish coated with fetal calf serum to remove adherent cells. After washing with IMDM 3 times, the resulting non-adherent bone marrow cells were used for the experiment. The cells were suspended in IMDM supplemented with 1% Neutridoma SP (Boehringer Mannheim), and each well of a 96-well flat-bottomed plate was inoculated with $1 \times 10^5$ cells, together with human recombinant GAF (rhGAF). A 125 μg/ml solution of rhGAF in 0.6M NaCl, 15% glycerin, 0.1% CHAPS, 10-mM Tris-HCl (pH 7.6) was diluted with IMDM, and a GAF-free buffer was similarly diluted, and they were added to the experiment system, respectively. Further, mouse recombinant IL-3 (mrIL-3) (Genzyme) was used as the positive control. Cell culturing was conducted at 37° C. for 4 days in the presence of air containing 5% $CO_2$. Then, 20 μl of PBS solution supplemented with 5 mg/ml MTT (Sigma) was added, followed by culturing at 37° C. for 5 hours. 100 μl of 10% SDS, 0.01N HCl solution was added thereto, and the resulting solution was further incubated overnight at 37° C. Then, the absorbance at 590 nm was measured and the proliferation of the bone marrow cells was examined. Results thereof are shown in FIG. 33.

Figure 34:
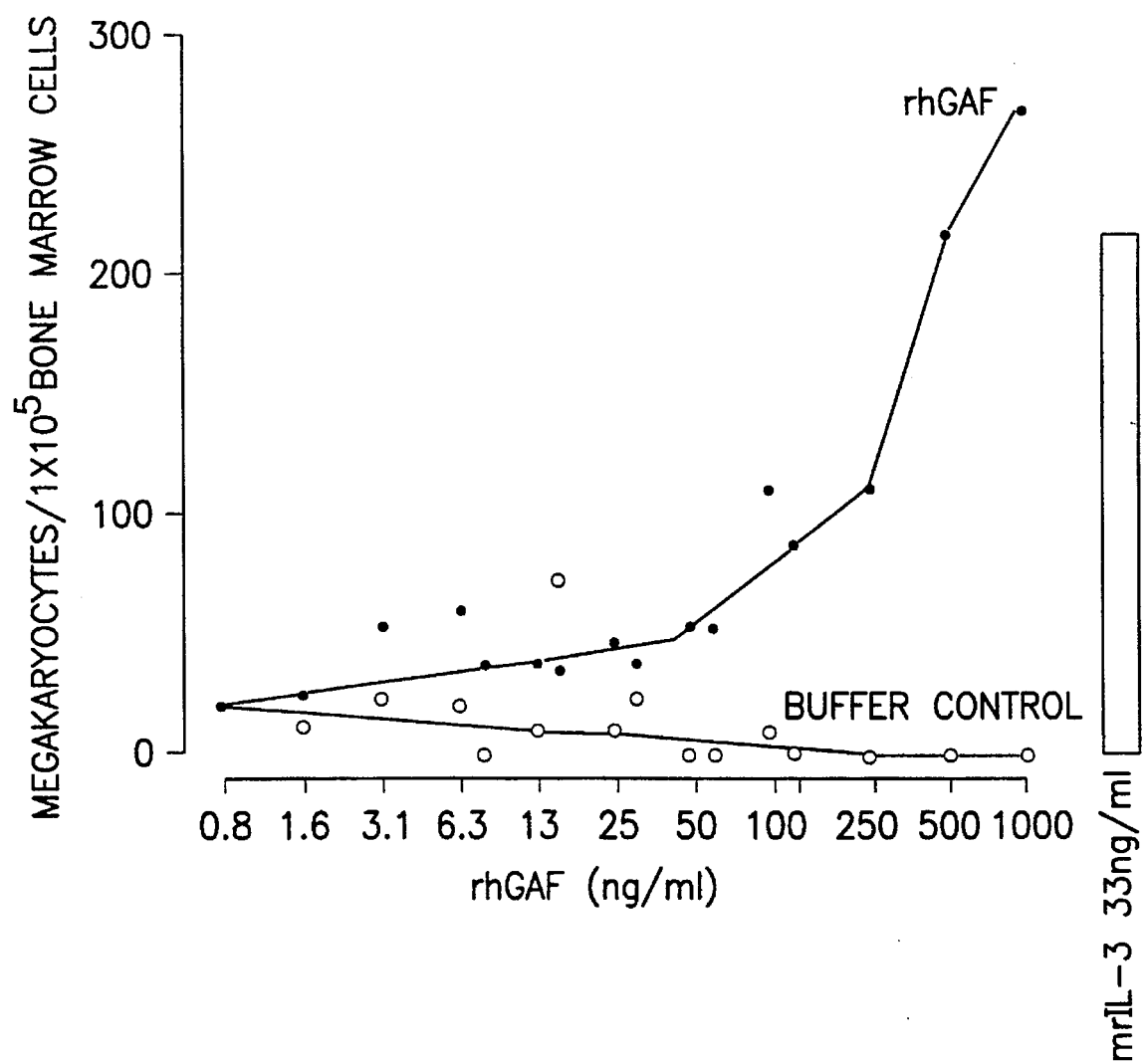
FIG. 34 is a graph showing activity of the purified rhGAF upon the proliferation of megakaryocytes in the mouse bone marrow cells.

Similarly, cells similarly prepared were cultured at 37° C. for 7 days in the presence of air containing 5% $CO_2$.50 μl of PBS solution supplemented with 5% glutaraldehyde was added, followed by centrifugation at 2,000 rpm for 5 minutes to fix the cells. After washing with 0.1M phosphate buffer (pH 6.0) once, megakaryocytes were stained by acetylcholinesterase staining (see Biochemical Experimental Courser second series, 8, Bloods, first volume, page 149), and the number of megakaryocytes per well was counted under an inverted microscope. Results thereof are shown in FIG. 34.

These results revealed that the rhGAF had the activity to support the growth of mouse bone marrow cells and further had the activity to megakaryocytes acting on their growth and maturation in the bone marrow cells.

What is claimed is:

1. A glia activating factor (GAF) which is a protein obtained from a glioma cell culture solution and has glial growth promoting activity, said GAF having the amino acid sequence of SEQ ID NO:1 or a fragment thereof possessing GAF activity.

2. A pharmaceutical composition comprising a therapeutically effective amount of glia activating factor as claimed in claim 1 and a pharmaceutically-acceptable carrier.

3. The pharmaceutical composition as claimed in claim 2, wherein said composition is a composition for promoting an increase in the number of platelets.

4. The pharmaceutical composition as claimed in claim 2, wherein said composition is used for a treatment or an improvement of cerebral lesion.

5. A glia activating factor (GAF) which is a protein obtained from a glioma cell culture solution and has glial growth promoting activity, said GAF having an amino acid sequence of SEQ ID NO:2 or SEQ ID NO:3, or a fragment thereof possessing GAF activity.

6. A pharmaceutical composition comprising a therapeutically effective amount of glia activating factor as claimed in claim 5 and a pharmaceutically-acceptable carrier.

7. The pharmaceutical composition as claimed in claim 6, wherein said composition is a composition for promoting an increase in the number of platelets.

8. The pharmaceutical composition as claimed in claim 6, wherein said composition is used for a treatment or an improvement of cerebral lesion.

9. A glia activating factor (GAF) which is a protein obtained from a glioma cell culture solution and has glial growth promoting activity, said GAF having an amino acid sequence selected from the group consisting of SEQ ID NO:4, SEQ ID NO:5, SEQ ID NO:6 and SEQ ID NO:7, or a fragment thereof possessing GAF activity.

10. A pharmaceutical composition comprising a therapeutically effective amount of glia activating factor as claimed in claim 9 and a pharmaceutically-acceptable carrier.

11. The pharmaceutical composition as claimed in claim 10, wherein said composition is a composition for promoting an increase in the number of platelets.

12. The pharmaceutical composition as claimed in claim 10, wherein said composition is used for a treatment or an improvement of cerebral lesion.

* * * * *

UNITED STATES PATENT AND TRADEMARK OFFICE
CERTIFICATE OF CORRECTION

PATENT NO.   : 5,622,928
DATED        : April 22, 1997
INVENTOR(S)  : Naruo, et al.

It is certified that error appears in the above-indentified patent and that said Letters Patent is hereby corrected as shown below:

On title page, item

[30]   Foreign Application Priority Data

Feb. 14, 1991   [JP] ....................3-20860
Sep.  4, 1991   [JP] ....................3-224454
Jan. 10, 1992   [JP] ....................4-3399

Signed and Sealed this

Twelfth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Leu  Asp  His  Leu  Lys  Gly  Ile  Leu  Arg  Arg  Arg  Gln  Leu  Tyr  Cys  Arg
 1              5                        10                       15

Thr  Gly  Phe  His  Leu  Glu  Ile  Phe  Pro  Asn  Gly  Thr  Ile  Gln  Gly  Thr
              20                        25                       30
```

| | | | | | | | | | | | | | | |
|---|---|---|---|---|---|---|---|---|---|---|---|---|---|---|
|Arg|Lys|Asp|His|Ser|Arg|Phe|Gly|Ile|Leu|Glu|Phe|Ile|Ser|Ile|Ala|
| |   |35 |   |   |   |40 |   |   |   |   |   |45 |   |   |   |

Val Gly Leu Val Ser Ile Arg Gly Val Asp Ser Gly Leu Tyr Leu Gly
    50              55              60

Met Asn Glu Lys Gly Glu Leu Tyr Gly Ser Glu Lys Leu Thr Gln Glu
65              70              75                          80

Cys Val Phe Arg Glu Gln Phe Glu Glu Asn Trp Tyr Asn Thr Tyr Ser
            85              90                      95

Ser Asn Leu Tyr Lys His Val Asp Thr Gly Arg Arg Tyr Tyr Val Ala
            100             105                 110

Leu Asn Lys Asp Gly Thr Pro Arg Glu Gly Thr Arg Thr Lys Arg His
            115             120             125

Gln Lys Phe Thr His Phe Leu Pro Arg Pro Val Asp Pro Asp
    130             135             140

(2) INFORMATION FOR SEQ ID NO:2:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO:2:

Ala Pro Leu Gly Glu Val Gly Asn Tyr Phe Gly Val Gln Asp Ala Val
1               5               10                  15

Pro Phe Gly Asn Val Pro Val Leu Pro Val Asp Ser Pro Val Leu Leu
            20              25              30

Ser Asp His Leu Gly Gln Ser Glu Ala Gly Gly Leu Pro Arg Gly Pro
            35              40              45

Ala Val Thr Asp Leu Asp His Leu Lys Gly Ile Leu Arg Arg Arg Gln
    50              55              60

Leu Tyr Cys Arg Thr Gly Phe His Leu Glu Ile Phe Pro Asn Gly Thr
65              70              75                          80

Ile Gln Gly Thr Arg Lys Asp His Ser Arg Phe Gly Ile Leu Glu Phe
                85              90                  95

Ile Ser Ile Ala Val Gly Leu Val Ser Ile Arg Gly Val Asp Ser Gly
            100             105             110

Leu Tyr Leu Gly Met Asn Glu Lys Gly Glu Leu Tyr Gly Ser Glu Lys
        115             120             125

Leu Thr Gln Glu Cys Val Phe Arg Glu Gln Phe Glu Glu Asn Trp Tyr
    130             135             140

Asn Thr Tyr Ser Ser Asn Leu Tyr Lys His Val Asp Thr Gly Arg Arg
145             150             155                         160

Tyr Tyr Val Ala Leu Asn Lys Asp Gly Thr Pro Arg Glu Gly Thr Arg
                165             170             175

Thr Lys Arg His Gln Lys Phe Thr His Phe Leu Pro Arg Pro Val Asp
        180             185             190

Pro Asp Lys Val Pro Glu Leu Tyr Lys Asp Ile Leu Ser Gln Ser
    195             200             205

(2) INFORMATION FOR SEQ ID NO:3:

(i) SEQUENCE CHARACTERISTICS:
        (A) LENGTH: 208 amino acids
        (B) TYPE: amino acid
        (D) TOPOLOGY: linear ( i i ) MOLECULE TYPE: protein ( x i ) SEQUENCE DESCRIPTION: SEQ ID NO:3:

| Met | Ala | Pro | Leu | Gly | Glu | Val | Gly | Asn | Tyr | Phe | Gly | Val | Gln | Asp | Ala |
|---|---|---|---|---|---|---|---|---|---|---|---|---|---|---|---|
| 1 | | | | 5 | | | | | 10 | | | | | 15 | |
| Val | Pro | Phe | Gly | Asn | Val | Pro | Val | Leu | Pro | Val | Asp | Ser | Pro | Val | Leu |
| | | | 20 | | | | 25 | | | | | 30 | | | |
| Leu | Ser | Asp | His | Leu | Gly | Gln | Ser | Glu | Ala | Gly | Gly | Leu | Pro | Arg | Gly |
| | | 35 | | | | 40 | | | | | | 45 | | | |
| Pro | Ala | Val | Thr | Asp | Leu | Asp | His | Leu | Lys | Gly | Ile | Leu | Arg | Arg | Arg |
| | 50 | | | | 55 | | | | | 60 | | | | | |
| Gln | Leu | Tyr | Cys | Arg | Thr | Gly | Phe | His | Leu | Glu | Ile | Phe | Pro | Asn | Gly |
| 65 | | | | | 70 | | | | 75 | | | | | 80 | |
| Thr | Ile | Gln | Gly | Thr | Arg | Lys | Asp | His | Ser | Arg | Phe | Gly | Ile | Leu | Glu |
| | | | | 85 | | | | | 90 | | | | | 95 | |
| Phe | Ile | Ser | Ile | Ala | Val | Gly | Leu | Val | Ser | Ile | Arg | Gly | Val | Asp | Ser |
| | | | 100 | | | | | 105 | | | | | 110 | | |
| Gly | Leu | Tyr | Leu | Gly | Met | Asn | Glu | Lys | Gly | Glu | Leu | Tyr | Gly | Ser | Glu |
| | | 115 | | | | | 120 | | | | | 125 | | | |
| Lys | Leu | Thr | Gln | Glu | Cys | Val | Phe | Arg | Glu | Gln | Phe | Glu | Glu | Asn | Trp |
| | 130 | | | | | 135 | | | | | 140 | | | | |
| Tyr | Asn | Thr | Tyr | Ser | Ser | Asn | Leu | Tyr | Lys | His | Val | Asp | Thr | Gly | Arg |
| 145 | | | | | 150 | | | | | 155 | | | | | 160 |
| Arg | Tyr | Tyr | Val | Ala | Leu | Asn | Lys | Asp | Gly | Thr | Pro | Arg | Glu | Gly | Thr |
| | | | | 165 | | | | | 170 | | | | | 175 | |
| Arg | Thr | Lys | Arg | His | Gln | Lys | Phe | Thr | His | Phe | Leu | Pro | Arg | Pro | Val |
| | | | 180 | | | | | 185 | | | | | 190 | | |
| Asp | Pro | Asp | Lys | Val | Pro | Glu | Leu | Tyr | Lys | Asp | Ile | Leu | Ser | Gln | Ser |
| | | 195 | | | | | 200 | | | | | 205 | | | |

( 2 ) INFORMATION FOR SEQ ID NO:4:

( i ) SEQUENCE CHARACTERISTICS:
        ( A ) LENGTH: 177 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Pro | Ser | Asp | His | Leu | Gly | Gln | Ser | Glu | Ala | Gly | Gly | Leu | Pro | Arg |
|---|---|---|---|---|---|---|---|---|---|---|---|---|---|---|---|
| 1 | | | | 5 | | | | | 10 | | | | | 15 | |
| Gly | Pro | Ala | Val | Thr | Asp | Leu | Asp | His | Leu | Lys | Gly | Ile | Leu | Arg | Arg |
| | | | 20 | | | | | 25 | | | | | 30 | | |
| Arg | Gln | Leu | Tyr | Cys | Arg | Thr | Gly | Phe | His | Leu | Glu | Ile | Phe | Pro | Asn |
| | | | 35 | | | | | 40 | | | | | 45 | | |
| Gly | Thr | Ile | Gln | Gly | Thr | Arg | Lys | Asp | His | Ser | Arg | Phe | Gly | Ile | Leu |
| | 50 | | | | | 55 | | | | | 60 | | | | |
| Glu | Phe | Ile | Ser | Ile | Ala | Val | Gly | Leu | Val | Ser | Ile | Arg | Gly | Val | Asp |
| 65 | | | | | 70 | | | | | 75 | | | | | 80 |
| Ser | Gly | Leu | Tyr | Leu | Gly | Met | Asn | Glu | Lys | Gly | Glu | Leu | Tyr | Gly | Ser |
| | | | | 85 | | | | | 90 | | | | | 95 | |
| Glu | Lys | Leu | Thr | Gln | Glu | Cys | Val | Phe | Arg | Glu | Gln | Phe | Glu | Glu | Asn |
| | | | 100 | | | | | 105 | | | | | 110 | | |
| Trp | Tyr | Asn | Thr | Tyr | Ser | Ser | Asn | Leu | Tyr | Lys | His | Val | Asp | Thr | Gly |
| | | | 115 | | | | | 120 | | | | | 125 | | |
| Arg | Arg | Tyr | Tyr | Val | Ala | Leu | Asn | Lys | Asp | Gly | Thr | Pro | Arg | Glu | Gly |

|   |   |   | 130 |   |   |   |   | 135 |   |   |   |   | 140 |   |   |   |
|---|---|---|---|---|---|---|---|---|---|---|---|---|---|---|---|---|

Thr Arg Thr Lys Arg His Gln Lys Phe Thr His Phe Leu Pro Arg Pro
145                     150                 155                 160

Val Asp Pro Asp Lys Val Pro Glu Leu Tyr Lys Asp Ile Leu Ser Gln
                165                 170                 175

Ser ( 2 ) INFORMATION FOR SEQ ID NO:5:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Leu Gly Glu Val Gly Asn Tyr Phe Gly Val Gln Asp Ala Val Pro Phe
1               5                   10                  15

Gly Asn Val Pro Val Leu Pro Val Asp Ser Pro Val Leu Leu Ser Asp
                20                  25                  30

His Leu Gly Gln Ser Glu Ala Gly Gly Leu Pro Arg Gly Pro Ala Val
            35                  40                  45

Thr Asp Leu Asp His Leu Lys Gly Ile Leu Arg Arg Arg Gln Leu Tyr
50                      55                  60

Cys Arg Thr Gly Phe His Leu Glu Ile Phe Pro Asn Gly Thr Ile Gln
65                  70                  75                  80

Gly Thr Arg Lys Asp His Ser Arg Phe Gly Ile Leu Glu Phe Ile Ser
                85                  90                  95

Ile Ala Val Gly Leu Val Ser Ile Arg Gly Val Asp Ser Gly Leu Tyr
                100                 105                 110

Leu Gly Met Asn Glu Lys Gly Glu Leu Tyr Gly Ser Glu Lys Leu Thr
            115                 120                 125

Gln Glu Cys Val Phe Arg Glu Gln Phe Glu Glu Asn Trp Tyr Asn Thr
130                 135                 140

Tyr Ser Ser Asn Leu Tyr Lys His Val Asp Thr Gly Arg Arg Tyr Tyr
145                 150                 155                 160

Val Ala Leu Asn Lys Asp Gly Thr Pro Arg Glu Gly Thr Arg Thr Lys
                165                 170                 175

Arg His Gln Lys Phe Thr His Phe Leu Pro Arg Pro Val Asp Pro Asp
                180                 185                 190

Lys Val Pro Glu Leu Tyr Lys Asp Ile Leu Ser Gln Ser
                195                 200                 205

( 2 ) INFORMATION FOR SEQ ID NO:6:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Ala Pro Ser Asp His Leu Gly Gln Ser Glu Ala Gly Gly Leu Pro
1               5                   10                  15

Arg Gly Pro Ala Val Thr Asp Leu Asp His Leu Lys Gly Ile Leu Arg
                20                  25                  30

Arg Arg Gln Leu Tyr Cys Arg Thr Gly Phe His Leu Glu Ile Phe Pro

```
                    35                          40                          45

Asn  Gly  Thr  Ile  Gln  Gly  Thr  Arg  Lys  Asp  His  Ser  Arg  Phe  Gly  Ile
     50                       55                      60

Leu  Glu  Phe  Ile  Ser  Ile  Ala  Val  Gly  Leu  Val  Ser  Ile  Arg  Gly  Val
65                            70                      75                      80

Asp  Ser  Gly  Leu  Tyr  Leu  Gly  Met  Asn  Glu  Lys  Gly  Glu  Leu  Tyr  Gly
                    85                       90                      95

Ser  Glu  Lys  Leu  Thr  Gln  Glu  Cys  Val  Phe  Arg  Glu  Gln  Phe  Glu  Glu
               100                      105                     110

Asn  Trp  Tyr  Asn  Thr  Tyr  Ser  Ser  Asn  Leu  Tyr  Lys  His  Val  Asp  Thr
          115                      120                     125

Gly  Arg  Arg  Tyr  Tyr  Val  Ala  Leu  Asn  Lys  Asp  Gly  Thr  Pro  Arg  Glu
     130                      135                     140

Gly  Thr  Arg  Thr  Lys  Arg  His  Gln  Lys  Phe  Thr  His  Phe  Leu  Pro  Arg
145                           150                     155                     160

Pro  Val  Asp  Pro  Asp  Lys  Val  Pro  Glu  Leu  Tyr  Lys  Asp  Ile  Leu  Ser
                    165                     170                     175

Gln  Ser
```

( 2 ) INFORMATION FOR SEQ ID NO:7:

( i ) SEQUENCE CHARACTERISTICS:
        ( A ) LENGTH: 206 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Leu  Gly  Glu  Val  Gly  Asn  Tyr  Phe  Gly  Val  Gln  Asp  Ala  Val  Pro
1              5                        10                      15

Phe  Gly  Asn  Val  Pro  Val  Leu  Pro  Val  Asp  Ser  Pro  Val  Leu  Leu  Ser
               20                       25                      30

Asp  His  Leu  Gly  Gln  Ser  Glu  Ala  Gly  Gly  Leu  Pro  Arg  Gly  Pro  Ala
          35                       40                      45

Val  Thr  Asp  Leu  Asp  His  Leu  Lys  Gly  Ile  Leu  Arg  Arg  Arg  Gln  Leu
     50                       55                      60

Tyr  Cys  Arg  Thr  Gly  Phe  His  Leu  Glu  Ile  Phe  Pro  Asn  Gly  Thr  Ile
65                       70                      75                      80

Gln  Gly  Thr  Arg  Lys  Asp  His  Ser  Arg  Phe  Gly  Ile  Leu  Glu  Phe  Ile
               85                       90                      95

Ser  Ile  Ala  Val  Gly  Leu  Val  Ser  Ile  Arg  Gly  Val  Asp  Ser  Gly  Leu
               100                      105                     110

Tyr  Leu  Gly  Met  Asn  Glu  Lys  Gly  Glu  Leu  Tyr  Gly  Ser  Glu  Lys  Leu
          115                      120                     125

Thr  Gln  Glu  Cys  Val  Phe  Arg  Glu  Gln  Phe  Glu  Glu  Asn  Trp  Tyr  Asn
     130                      135                     140

Thr  Tyr  Ser  Ser  Asn  Leu  Tyr  Lys  His  Val  Asp  Thr  Gly  Arg  Arg  Tyr
145                      150                     155                     160

Tyr  Val  Ala  Leu  Asn  Lys  Asp  Gly  Thr  Pro  Arg  Glu  Gly  Thr  Arg  Thr
                    165                     170                     175

Lys  Arg  His  Gln  Lys  Phe  Thr  His  Phe  Leu  Pro  Arg  Pro  Val  Asp  Pro
               180                      185                     190

Asp  Lys  Val  Pro  Glu  Leu  Tyr  Lys  Asp  Ile  Leu  Ser  Gln  Ser
          195                      200                     205
```

(2) INFORMATION FOR SEQ ID NO:8:

(i) SEQUENCE CHARACTERISTICS:
        (A) LENGTH: 206 amino acids
        (B) TYPE: amino acid
        (D) TOPOLOGY: linear (ii) MOLECULE TYPE: protein (xi) SEQUENCE DESCRIPTION: SEQ ID NO:8:

```
Met Leu Gly Glu Val Gly Asn Tyr Phe Gly Val Gln Asp Ala Val Pro
 1               5                  10                  15
Phe Gly Asn Val Pro Val Leu Pro Val Asp Ser Pro Val Leu Leu Ser
                20                  25                  30
Asp His Leu Gly Gln Ser Glu Ala Gly Gly Leu Pro Arg Gly Pro Ala
            35                  40                  45
Val Thr Asp Leu Asp His Leu Lys Gly Ile Leu Arg Arg Arg Gln Leu
    50                  55                  60
Tyr Cys Arg Thr Gly Phe His Leu Glu Ile Phe Pro Asn Gly Thr Ile
 65                 70                  75                  80
Gln Gly Thr Arg Lys Asp His Ser Arg Phe Gly Ile Leu Glu Phe Ile
                85                  90                  95
Ser Ile Ala Val Gly Leu Val Ser Ile Arg Gly Val Asp Ser Gly Leu
                100                 105                 110
Tyr Leu Gly Met Asn Glu Lys Gly Glu Leu Tyr Gly Ser Glu Lys Leu
            115                 120                 125
Thr Gln Glu Cys Val Phe Arg Glu Gln Phe Glu Glu Asn Trp Tyr Asn
    130                 135                 140
Thr Tyr Ser Ser Asn Leu Tyr Lys His Val Asp Thr Gly Arg Arg Tyr
145                 150                 155                 160
Tyr Val Ala Leu Asn Lys Asp Gly Thr Pro Arg Glu Gly Thr Arg Thr
                165                 170                 175
Lys Arg His Gln Lys Phe Thr His Phe Leu Pro Arg Pro Val Asp Pro
                180                 185                 190
Asp Lys Val Pro Glu Leu Tyr Lys Asp Ile Leu Ser Gln Ser
                195                 200                 205
```

(2) INFORMATION FOR SEQ ID NO:9:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:9:

```
Met Ala Pro Leu Gly Glu Val Gly Asn Tyr Phe Gly Val Gln Asp Ala
 1               5                  10                  15
Val Pro Phe Gly Asn Val Pro Val Leu Pro Val Asp Ser Pro Val Leu
                20                  25                  30
Leu Ser Asp His Leu Gly Gln Ser Glu Ala Gly Gly Leu Pro Arg Gly
            35                  40                  45
Pro Ala Val Thr Asp Leu Asp His Leu Lys Gly Ile Leu Arg Arg Arg
    50                  55                  60
Gln Leu Tyr Cys Arg Thr Gly Phe His Leu Glu Ile Phe Pro Asn Gly
 65                 70                  75                  80
Thr Ile Gln Gly Thr Arg Lys Asp His Ser Arg Phe Gly Ile Leu Glu
                85                  90                  95
```

| Phe | Ile | Ser | Ile | Ala | Val | Gly | Leu | Val | Ser | Ile | Arg | Gly | Val | Asp | Ser |
|---|---|---|---|---|---|---|---|---|---|---|---|---|---|---|---|
| | | | 100 | | | | | 105 | | | | | 110 | | |

| Gly | Leu | Tyr | Leu | Gly | Met | Asn | Glu | Lys | Gly | Glu | Leu | Tyr | Gly | Ser | Glu |
|---|---|---|---|---|---|---|---|---|---|---|---|---|---|---|---|
| | | | 115 | | | | 120 | | | | | 125 | | | |

| Lys | Leu | Thr | Gln | Glu | Cys | Val | Phe | Arg | Glu | Gln | Phe | Glu | Glu | Asn | Trp |
|---|---|---|---|---|---|---|---|---|---|---|---|---|---|---|---|
| | | 130 | | | | 135 | | | | 140 | | | | | |

| Tyr | Asn | Thr | Tyr | Ser | Ser | Asn | Leu | Tyr | Lys | His | Val | Asp | Thr | Gly | Arg |
|---|---|---|---|---|---|---|---|---|---|---|---|---|---|---|---|
| 145 | | | | | 150 | | | | | 155 | | | | | 160 |

| Arg | Tyr | Tyr | Val | Ala | Leu | Asn | Lys | Asp | Gly | Thr | Pro | Arg | Glu | Gly | Thr |
|---|---|---|---|---|---|---|---|---|---|---|---|---|---|---|---|
| | | | | 165 | | | | | 170 | | | | | 175 | |

| Arg | Thr | Lys | Arg | His | Gln | Lys | Phe | Thr | His | Phe | Leu | Pro | Arg | Pro | Val |
|---|---|---|---|---|---|---|---|---|---|---|---|---|---|---|---|
| | | | 180 | | | | | 185 | | | | | 190 | | |

| Asp | Pro | Asp | Lys | Val | Pro | Glu | Leu | Tyr | Lys | Asp | Ile | Leu | Ser | Gln | Ser |
|---|---|---|---|---|---|---|---|---|---|---|---|---|---|---|---|
| | | | 195 | | | | | 200 | | | | | 205 | | |

( 2 ) INFORMATION FOR SEQ ID NO:10:

( i ) SEQUENCE CHARACTERISTICS:
        ( A ) LENGTH: 426 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:10:

```
TTGGATCATT TAAAGGGGAT TCTCAGGCGG AGGCAGCTAT ACTGCAGGAC TGGATTTCAC      60
TTAGAAATCT TCCCCAATGG TACTATCCAG GGAACCAGGA AGACCACAG CCGATTTGGC      120
ATTCTGGAAT TTATCAGTAT AGCAGTGGGC CTGGTCAGCA TTCGAGGCGT GGACAGTGGA     180
CTCTACCTCG GGATGAATGA AAGGGGGAG CTGTATGGAT CAGAAAAACT AACCCAAGAG      240
TGTGTATTCA GAGAACAGTT CGAAGAAAAC TGGTATAATA CGTACTCGTC AAACCTATAT     300
AAGCACGTGG ACACTGGAAG GCGATACTAT GTTGCATTAA ATAAAGATGG GACCCCGAGA     360
GAAGGGACTA GGACTAAACG GCACCAGAAA TTCACACATT TTTTACCTAG ACCAGTGGAC     420
CCCGAC                                                                426
```

( 2 ) INFORMATION FOR SEQ ID NO:11:

( i ) SEQUENCE CHARACTERISTICS:
        ( A ) LENGTH: 621 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:11:

```
GCTCCCTTAG GTGAAGTTGG GAACTATTTC GGTGTGCAGG ATGCGGTACC GTTTGGGAAT     60
GTGCCCGTGT TGCCGGTGGA CAGCCCGGTT TTGTTAAGTG ACCACCTGGG TCAGTCCGAA     120
GCAGGGGGGC TCCCCAGGGG ACCCGCAGTC ACGGACTTGG ATCATTTAAA GGGGATTCTC     180
AGGCGGAGGC AGCTATACTG CAGGACTGGA TTTCACTTAG AAATCTTCCC CAATGGTACT     240
ATCCAGGGAA CCAGGAAAGA CCACAGCCGA TTTGGCATTC TGGAATTTAT CAGTATAGCA     300
```

| GTGGGCCTGG | TCAGCATTCG | AGGCGTGGAC | AGTGGACTCT | ACCTCGGGAT | GAATGAGAAG | 360 |
| GGGGAGCTGT | ATGGATCAGA | AAAACTAACC | CAAGAGTGTG | TATTCAGAGA | ACAGTTCGAA | 420 |
| GAAAACTGGT | ATAATACGTA | CTCGTCAAAC | CTATATAAGC | ACGTGGACAC | TGGAAGGCGA | 480 |
| TACTATGTTG | CATTAAATAA | AGATGGGACC | CCGAGAGAAG | GGACTAGGAC | TAAACGGCAC | 540 |
| CAGAAATTCA | CACATTTTTT | ACCTAGACCA | GTGGACCCCG | ACAAGTACC | TGAACTGTAT | 600 |
| AAGGATATTC | TAAGCCAAAG | T | | | | 621 |

( 2 ) INFORMATION FOR SEQ ID NO:12:

( i ) SEQUENCE CHARACTERISTICS:
        ( A ) LENGTH: 624 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:12:

| ATGGCTCCCT | TAGGTGAAGT | TGGGAACTAT | TTCGGTGTGC | AGGATGCGGT | ACCGTTTGGG | 60 |
| AATGTGCCCG | TGTTGCCGGT | GGACAGCCCG | GTTTGTTAA | GTGACCACCT | GGGTCAGTCC | 120 |
| GAAGCAGGGG | GGCTCCCCAG | GGGACCCGCA | GTCACGGACT | TGGATCATTT | AAAGGGGATT | 180 |
| CTCAGGCGGA | GGCAGCTATA | CTGCAGGACT | GGATTTCACT | TAGAAATCTT | CCCCAATGGT | 240 |
| ACTATCCAGG | GAACCAGGAA | AGACCACAGC | CGATTTGGCA | TTCTGGAATT | TATCAGTATA | 300 |
| GCAGTGGGCC | TGGTCAGCAT | TCGAGGCGTG | GACAGTGGAC | TCTACCTCGG | GATGAATGAG | 360 |
| AAGGGGGAGC | TGTATGGATC | AGAAAAACTA | ACCCAAGAGT | GTGTATTCAG | AACAGTTC | 420 |
| GAAGAAAACT | GGTATAATAC | GTACTCGTCA | AACCTATATA | AGCACGTGGA | CACTGGAAGG | 480 |
| CGATACTATG | TTGCATTAAA | TAAAGATGGG | ACCCCGAGAG | AAGGGACTAG | GACTAAACGG | 540 |
| CACCAGAAAT | TCACACATTT | TTTACCTAGA | CCAGTGGACC | CCGACAAAGT | ACCTGAACTG | 600 |
| TATAAGGATA | TTCTAAGCCA | AAGT | | | | 624 |

( 2 ) INFORMATION FOR SEQ ID NO:13:

( i ) SEQUENCE CHARACTERISTICS:
        ( A ) LENGTH: 621 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:13:

| GCTCCCTTAG | GTGAAGTTGG | GAACTATTTC | GGTGTGCAGG | ATGCGGTACC | GTTTGGGAAT | 60 |
| GTGCCCGTGT | TGCCGGTGGA | CAGCCCGGTT | TGTTAAGTG | ACCACCTGGG | TCAGTCCGAA | 120 |
| GCAGGGGGGC | TCCCCAGGGG | ACCCGCAGTC | ACGGACTTGG | ATCATTTAAA | GGGGATTCTC | 180 |
| AGGCGGAGGC | AGCTATACTG | CAGGACTGGA | TTTCACTTAG | AAATCTTCCC | CAATGGTACT | 240 |
| ATCCAGGGAA | CCAGGAAAGA | CCACAGCCGA | TTTGGCATTC | TGGAATTTAT | CAGTATAGCA | 300 |
| GTGGGCCTGG | TCAGCATTCG | AGGCGTGGAC | AGTGGACTCT | ACCTCGGGAT | GAATGAGAAG | 360 |

-continued

| GGGGAGCTGT | ATGGATCAGA | AAAACTAACC | CAAGAGTGTG | TATTCAGAGA | ACAGTTCGAA | 420 |
| GAAAACTGGT | ATAATACGTA | CTCGTCAAAC | CTATATAAGC | ACGTGGACAC | TGGAAGGCGA | 480 |
| TACTATGTTG | CATTAAATAA | AGATGGGACC | CCGAGAGAAG | GGACTAGGAC | TAAACGGCAC | 540 |
| CAGAAATTCA | CACATTTTTT | ACCTAGACCA | GTGGACCCCG | ACAAAGTACC | TGAACTGTAT | 600 |
| AAGGATATTC | TAAGCCAAAG | T | | | | 621 |

( 2 ) INFORMATION FOR SEQ ID NO:14:

( i ) SEQUENCE CHARACTERISTICS:
        ( A ) LENGTH: 621 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:14:

| GCTCCCTTAG | GTGAAGTTGG | GAACTATTTC | GGTGTGCAGG | ATGCGGTACC | GTTTGGGAAT | 60 |
| GTGCCCGTGT | TGCCGGTGGA | CAGCCCGGTT | TTGTTAAGTG | ACCACCTGGG | TCAGTCCGAA | 120 |
| GCAGGGGGGC | TCCCCAGGGG | ACCCGCAGTC | ACGGACTTGG | ATCATTTAAA | GGGGATTCTC | 180 |
| AGGCGGAGGC | AGCTATACTG | CAGGACTGGA | TTTCACTTAG | AAATCTTCCC | CAATGGTACT | 240 |
| ATCCAGGGAA | CCAGGAAAGA | CCACAGCCGA | TTTGGCATTC | TGGAATTTAT | CAGTATAGCA | 300 |
| GTGGGCCTGG | TCAGCATTCG | AGGCGTGGAC | AGTGGACTCT | ACCTCGGGAT | GAATGAGAAG | 360 |
| GGGGAGCTGT | ATGGATCAGA | AAAACTAACC | CAAGAGTGTG | TATTCAGAGA | ACAGTTCGAA | 420 |
| GAAAACTGGT | ATAATACGTA | CTCGTCAAAC | CTATATAAGC | ACGTGGACAC | TGGAAGGCGA | 480 |
| TACTATGTTG | CATTAAATAA | AGATGGGACC | CCGAGAGAAG | GGACTAGGAC | TAAACGGCAC | 540 |
| CAGAAATTCA | CACATTTTTT | ACCTAGACCA | GTGGACCCCG | ACAAAGTACC | TGAACTGTAT | 600 |
| AAGGATATTC | TAAGCCAAAG | T | | | | 621 |

( 2 ) INFORMATION FOR SEQ ID NO:15:

( i ) SEQUENCE CHARACTERISTICS:
        ( A ) LENGTH: 624 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:15:

| ATGGCTCCCT | TAGGTGAAGT | TGGGAACTAT | TTCGGTGTGC | AGGATGCGGT | ACCGTTTGGG | 60 |
| AATGTGCCCG | TGTTGCCGGT | GGACAGCCCG | GTTTTGTTAA | GTGACCACCT | GGGTCAGTCC | 120 |
| GAAGCAGGGG | GGCTCCCCAG | GGGACCCGCA | GTCACGGACT | TGGATCATTT | AAAGGGGATT | 180 |
| CTCAGGCGGA | GGCAGCTATA | CTGCAGGACT | GGATTTCACT | TAGAAATCTT | CCCCAATGGT | 240 |
| ACTATCCAGG | GAACCAGGAA | AGACCACAGC | CGATTTGGCA | TTCTGGAATT | TATCAGTATA | 300 |
| GCAGTGGGCC | TGGTCAGCAT | TCGAGGCGTG | GACAGTGGAC | TCTACCTCGG | GATGAATGAG | 360 |
| AAGGGGGAGC | TGTATGGATC | AGAAAAACTA | ACCCAAGAGT | GTGTATTCAG | AGAACAGTTC | 420 |
| GAAGAAAACT | GGTATAATAC | GTACTCGTCA | AACCTATATA | AGCACGTGGA | CACTGGAAGG | 480 |
| CGATACTATG | TTGCATTAAA | TAAAGATGGG | ACCCCGAGAG | AAGGGACTAG | GACTAAACGG | 540 |

```
CACCAGAAAT  TCACACATTT  TTTACCTAGA  CCAGTGGACC  CCGACAAAGT  ACCTGAACTG     600

TATAAGGATA  TTCTAAGCCA  AAGT                                              624
```

( 2 ) INFORMATION FOR SEQ ID NO:16:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens
        ( E ) HAPLOTYPE: 2n
        ( F ) TISSUE TYPE: brain
        ( G ) CELL TYPE: glioma
        ( H ) CELL LINE: NMC-G1

( i x ) FEATURE:
        ( B ) LOCATION: 3 Xaa= His or Pro, 14 Xaa= undetermined
        ( C ) IDENTIFICATION METHOD: E ( x i ) SEQUENCE DESCRIPTION: SEQ ID NO:16:

```
Ala  Asp  Xaa  Leu  Gly  Gln  Ser  Glu  Ala  Gly  Gly  Leu  Pro  Xaa  Gly  Pro
1                  5                        10                       15
Ala  Val  Thr  Asp  Leu
                20
```

( 2 ) INFORMATION FOR SEQ ID NO:17:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens
        ( E ) HAPLOTYPE: 2n
        ( F ) TISSUE TYPE: brain
        ( G ) CELL TYPE: glioma
        ( H ) CELL LINE: NMC-G1

( i x ) FEATURE:
        ( B ) LOCATION: 1 Xaa=undetermined, 12 (Ser)= predicted
        ( C ) IDENTIFICATION METHOD: E ( x i ) SEQUENCE DESCRIPTION: SEQ ID NO:17:

```
Xaa  Gln  Asp  Ala  Val  Pro  Phe  Gly  Asn  Val  Pro  Ser  Leu
1                  5                        10
```

( 2 ) INFORMATION FOR SEQ ID NO:18:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
                 ( A ) ORGANISM: Homo sapiens
                 ( E ) HAPLOTYPE: 2n
                 ( F ) TISSUE TYPE: brain
                 ( G ) CELL TYPE: glioma
                 ( H ) CELL LINE: NMC-G1

( i x ) FEATURE:
                 ( B ) LOCATION: 1 Xaa= Leu or Ala, 20 (Pro)= predicted,
                       21 Xaa=undetermined
                 ( C ) IDENTIFICATION METHOD: E ( x i ) SEQUENCE DESCRIPTION: SEQ ID NO:18:

Xaa  Gly  Glu  Val  Gly  Asn  Tyr  Phe  Gly  Val  Gln  Asp  Ala  Val  Pro  Phe
1                  5                            10                           15

Gly  Asn  Val  Pro  Xaa  Leu  Leu
                20

( 2 ) INFORMATION FOR SEQ ID NO:19:

( i ) SEQUENCE CHARACTERISTICS:
                 ( A ) LENGTH: 25 base pairs
                 ( B ) TYPE: nucleic acid
                 ( C ) STRANDEDNESS: single
                 ( D ) TOPOLOGY: linear ( i i ) MOLECULE TYPE: other nucleic acid, synthesizing DNA ( i i i ) HYPOTHETICAL: YES ( i v ) ANTI-SENSE: NO ( v i ) ORIGINAL SOURCE:
                 ( A ) ORGANISM: Homo sapiens ( i x ) FEATURE:
                 ( A ) NAME/KEY: 11, 14

( x i ) SEQUENCE DESCRIPTION: SEQ ID NO:19:

AAGGATCCGT  NGGNAAYTAY  TTYGG                                                25

( 2 ) INFORMATION FOR SEQ ID NO:20:

( i ) SEQUENCE CHARACTERISTICS:
                 ( A ) LENGTH: 25 base pairs
                 ( B ) TYPE: nucleic acid
                 ( C ) STRANDEDNESS: single
                 ( D ) TOPOLOGY: linear ( i i ) MOLECULE TYPE: other nucleic acid, synthesizing DNA ( i i i ) HYPOTHETICAL: YES ( i v ) ANTI-SENSE: YES ( i x ) FEATURE:
                 ( A ) NAME/KEY: 14, 20, 23

( x i ) SEQUENCE DESCRIPTION: SEQ ID NO:20:

AAGAATTCAC  RTTNCCRAAN  GGNAC                                                25

( 2 ) INFORMATION FOR SEQ ID NO:21:

( i ) SEQUENCE CHARACTERISTICS:
                 ( A ) LENGTH: 59 base pairs ( B ) TYPE: nucleic acid
( C ) STRANDEDNESS: double
( D ) TOPOLOGY: linear ( i i ) MOLECULE TYPE: other nucleic acid, PCR product from genomic DNA ( i i i ) HYPOTHETICAL: NO ( i v ) ANTI-SENSE: NO ( v i ) ORIGINAL SOURCE:
( A ) ORGANISM: Homo sapiens ( x i ) SEQUENCE DESCRIPTION: SEQ ID NO:21:

GGATCCGTGG GGAACTATTT CGGGGTGCAG GATGCGGTCC CCTTCGGCAA CGTGAATTC    59

( 2 ) INFORMATION FOR SEQ ID NO:22:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid, synthetic DNA ( i i i ) HYPOTHETICAL: YES ( i v ) ANTI-SENSE: NO ( x i ) SEQUENCE DESCRIPTION: SEQ ID NO:22:

TGGGGAACTA TTTCGGGGTG CAGGATGCGG    30

( 2 ) INFORMATION FOR SEQ ID NO:23:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid, synthetic DNA ( i i i ) HYPOTHETICAL: YES ( i v ) ANTI-SENSE: YES ( x i ) SEQUENCE DESCRIPTION: SEQ ID NO:23:

ACGTTGCCGA AGGGGACCGC ATCCTGCACC    30

( 2 ) INFORMATION FOR SEQ ID NO:24:

( i ) SEQUENCE CHARACTERISTICS:
( A ) LENGTH: 1493 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v ) ORIGINAL SOURCE:
( A ) ORGANISM: Homo sapiens
( E ) HAPLOTYPE: 2n
( F ) TISSUE TYPE: skin
( G ) CELL TYPE: fibroblast ( v i i ) IMMEDIATE SOURCE:
( A ) LIBRARY: Human foreskin cDNA library
( B ) CLONE: pGAF1

( x i ) SEQUENCE DESCRIPTION: SEQ ID NO:24:

| | | | | | |
|---|---|---|---|---|---|
| TGAAACAGCA | GATTACTTTT | ATTTATGCAT | TTAATGGATT | GAAGAAAAGA | ACCTTTTTTT | 60 |
| TTCTCTCTCT | CTCTGCAACT | GCAGTAAGGG | AGGGGAGTTG | GATATACCTC | GCCTAATATC | 120 |
| TCCTGGGTTG | ACACCATCAT | TATTGTTTAT | TCTTGTGCTC | CAAAAGCCGA | GTCCTCTGAT | 180 |
| GGCTCCCTTA | GGTGAAGTTG | GGAACTATTT | CGGTGTGCAG | GATGCGGTAC | CGTTTGGGAA | 240 |
| TGTGCCCGTG | TTGCCGGTGG | ACAGCCCGGT | TTTGTTAAGT | GACCACCTGG | GTCAGTCCGA | 300 |
| AGCAGGGGGG | CTCCCCAGGG | GACCCGCAGT | CACGGACTTG | GATCATTTAA | AGGGGATTCT | 360 |
| CAGGCGGAGG | CAGCTATACT | GCAGGACTGG | ATTTCACTTA | GAAATCTTCC | CCAATGGTAC | 420 |
| TATCCAGGGA | ACCAGGAAAG | ACCACAGCCG | ATTTGGCATT | CTGGAATTTA | TCAGTATAGC | 480 |
| AGTGGGCCTG | GTCAGCATTC | GAGGCGTGGA | CAGTGGACTC | TACCTCGGGA | TGAATGAGAA | 540 |
| GGGGGAGCTG | TATGGATCAG | AAAAACTAAC | CCAAGAGTGT | GTATTCAGAG | AACAGTTCGA | 600 |
| AGAAAACTGG | TATAATACGT | ACTCGTCAAA | CCTATATAAG | CACGTGGACA | CTGGAAGGCG | 660 |
| ATACTATGTT | GCATTAAATA | AGATGGGAC | CCCGAGAGAA | GGGACTAGGA | CTAAACGGCA | 720 |
| CCAGAAATTC | ACACATTTTT | TACCTAGACC | AGTGGACCCC | GACAAAGTAC | CTGAACTGTA | 780 |
| TAAGGATATT | CTAAGCCAAA | GTTGACAAAG | ACAATTTCTT | CACTTGAGCC | CTTAAAAAAG | 840 |
| TAACCACTAT | AAAGGTTTCA | CGCGGTGGGT | TCTTATTGAT | TCGCTGTGTC | ATCACATCAG | 900 |
| CTCCACTGTT | GCCAAACTTT | GTCGCATGCA | TAATGTATGA | TGGAGGCTTG | GATGGGAATA | 960 |
| TGCTGATTTT | GTTCTGCACT | TAAAGGCTTC | TCCTCCTGGA | GGGCTGCCTA | GGGCCACTTG | 1020 |
| CTTGATTTAT | CATGAGAGAA | GAGGAGAGAG | AGAGAGACTG | AGCGCTAGGA | GTGTGTGTAT | 1080 |
| GTGTGTGTGT | GTGTGTGTGT | GTGTGTGTGT | ATGTGTGTAG | CGGGAGATGT | GGGCGGAGCG | 1140 |
| AGAGCAAAAG | GACTGCGGCC | TGATGCATGC | TGGAAAAAGA | CACGCTTTTC | ATTTCTGATC | 1200 |
| AGTTGTACTT | CATCCTATAT | CAGCACAGCT | GCCATACTTC | GACTTATCAG | GATTCTGGCT | 1260 |
| GGTGGCCTGC | GCGAGGGTGC | AGTCTTACTT | AAAAGACTTT | CAGTTAATTC | TCACTGGTAT | 1320 |
| CATCGCAGTG | AACTTAAAGC | AAAGACCTCT | TAGTAAAAAA | TAAAAAAAAA | TAAAAAATAA | 1380 |
| AAATAAAAAA | AGTTAAATTT | ATTTATAGAA | ATTCCAAAAA | AAAAAAAAAA | AAAAAAAAAA | 1440 |
| AAAAAAAAAA | AAAAAAAAAA | AAAAAAAAAA | AAAAAAAAAA | AAAAAAAAA | AAA | 1493 |

( 2 ) INFORMATION FOR SEQ ID NO:25:

( i ) SEQUENCE CHARACTERISTICS:
        ( A ) LENGTH: 208 amino acids
        ( B ) TYPE: amino acid
        ( D ) TOPOLOGY: linear ( i i ) MOLECULE TYPE: protein ( i i i ) HYPOTHETICAL: NO ( i v ) ORIGINAL SOURCE:
        ( A ) ORGANISM: Homo sapiens
        ( E ) HAPLOTYPE: 2n
        ( F ) TISSUE TYPE: skin
        ( G ) CELL TYPE: fibroblast ( v i i ) IMMEDIATE SOURCE:
        ( A ) LIBRARY: Human foreskin cDNA library
        ( B ) CLONE: pGAF1

( x i ) SEQUENCE DESCRIPTION: SEQ ID NO:25:

| Met | Ala | Pro | Leu | Gly | Glu | Val | Gly | Asn | Tyr | Phe | Gly | Val | Gln | Asp | Ala |
|---|---|---|---|---|---|---|---|---|---|---|---|---|---|---|---|
| 1 | | | | 5 | | | | | 10 | | | | | 15 | |

| Val | Pro | Phe | Gly | Asn | Val | Pro | Val | Leu | Pro | Val | Asp | Ser | Pro | Val | Leu |

|   |   |   | 20 |   |   |   | 25 |   |   |   | 30 |   |   |
|---|---|---|---|---|---|---|---|---|---|---|---|---|---|
| Leu | Ser | Asp 35 | His | Leu | Gly | Gln | Ser 40 | Glu | Ala | Gly | Gly | Leu 45 | Pro | Arg | Gly |
| Pro | Ala 50 | Val | Thr | Asp | Leu 55 | Asp | His | Leu | Lys | Gly | Ile 60 | Leu | Arg | Arg | Arg |
| Gln 65 | Leu | Tyr | Cys | Arg | Thr 70 | Gly | Phe | His | Leu | Glu 75 | Ile | Phe | Pro | Asn | Gly 80 |
| Thr | Ile | Gln | Gly | Thr 85 | Arg | Lys | Asp | His | Ser 90 | Arg | Phe | Gly | Ile | Leu 95 | Glu |
| Phe | Ile | Ser | Ile 100 | Ala | Val | Gly | Leu | Val 105 | Ser | Ile | Arg | Gly | Val 110 | Asp | Ser |
| Gly | Leu | Tyr 115 | Leu | Gly | Met | Asn | Glu 120 | Lys | Gly | Glu | Leu | Tyr 125 | Gly | Ser | Glu |
| Lys | Leu 130 | Thr | Gln | Glu | Cys | Val 135 | Phe | Arg | Glu | Gln | Phe 140 | Glu | Glu | Asn | Trp |
| Tyr 145 | Asn | Thr | Tyr | Ser | Ser 150 | Asn | Leu | Tyr | Lys | His 155 | Val | Asp | Thr | Gly | Arg 160 |
| Arg | Tyr | Tyr | Val | Ala 165 | Leu | Asn | Lys | Asp | Gly 170 | Thr | Pro | Arg | Glu | Gly 175 | Thr |
| Arg | Thr | Lys | Arg 180 | His | Gln | Lys | Phe | Thr 185 | His | Phe | Leu | Pro | Arg 190 | Pro | Val |
| Asp | Pro | Asp 195 | Lys | Val | Pro | Glu | Leu 200 | Tyr | Lys | Asp | Ile | Leu 205 | Ser | Gln | Ser |

( 2 ) INFORMATION FOR SEQ ID NO:26:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i i i ) HYPOTHETICAL: NO ( i v ) ANTI-SENSE: NO ( x i ) SEQUENCE DESCRIPTION: SEQ ID NO:26:

```
TATGTTAGGT GAAGTTGGGA ACTATTTCGG TGTGCAGGAT GCGGTAC                    47
```

( 2 ) INFORMATION FOR SEQ ID NO:27:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i i i ) HYPOTHETICAL: NO ( i v ) ANTI-SENSE: YES ( x i ) SEQUENCE DESCRIPTION: SEQ ID NO:27:

```
CGCATCCTGC ACACCGAAAT AGTTCCCAAC TTCACCTAAC A                          41
```